Figure 1:
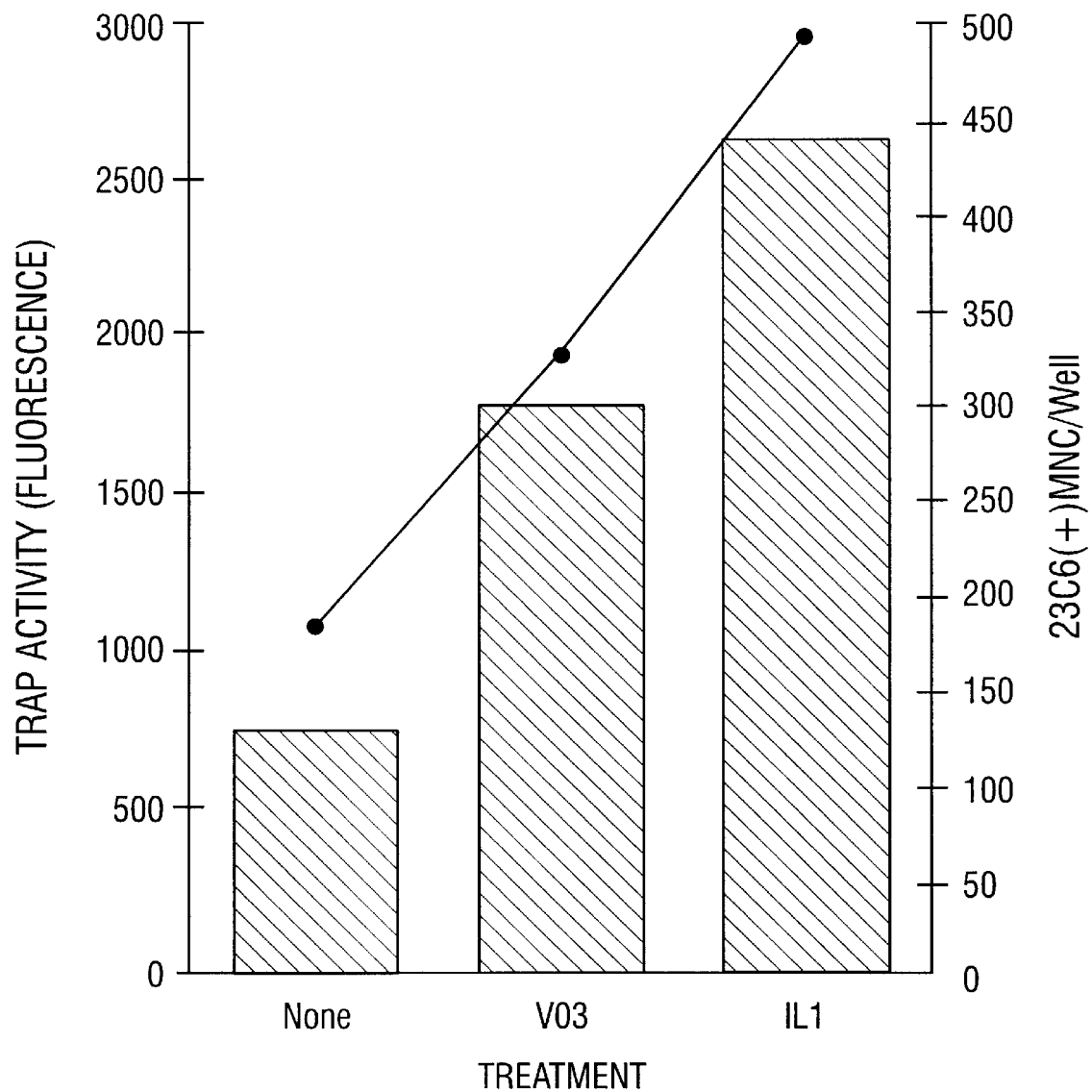

US005985832A

United States Patent [19]
Roodman et al.

[11] Patent Number: 5,985,832
[45] Date of Patent: Nov. 16, 1999

[54] COMPOSITIONS AND METHODS OF USE FOR OSTEOCLAST INHIBITOR FACTORS

[75] Inventors: G. David Roodman; Sakamuri V. Reddy; Sun-Jin Choi, all of San Antonio, Tex.

[73] Assignee: Board of Regents, The University of Texas System, Austin, Tex.

[21] Appl. No.: 09/139,424

[22] Filed: Aug. 25, 1998

Related U.S. Application Data

[62] Division of application No. 08/772,441, Dec. 20, 1996.
[51] Int. Cl.$^6$ ................................................... A61K 38/00
[52] U.S. Cl. .................................................. 514/12; 514/2
[58] Field of Search ..................................... 514/2, 9, 12

[56] References Cited

PUBLICATIONS

Akatsu et al., "Preparation and characterization of a mouse osteoclast–like multinucleated cell population," *J. Bone Miner. Res.* 7(11):1297–1306, 1992.

Abdulkarim et al., "Interleukin–6 does not stimulate bone resorption in neonatal mouse calvariae," *J. Bone Miner. Res.* 6(1):3–8, 1991.

Alcantara et al., "Transcriptional regulation of the tartrate–resistant acid phosphatase (TRAP) gene by iron," *Biochem. J.*, 298:421–425, 1994.

Bartkiewicz et al., "Characterization of the osteoclast vacuolar H$^+$–ATPase B–subunit," *Gene* 160:157–164, 1995.

Blake et al., "Ly–6 in kidney is widely expressed on Tubular epithelium and vascular endothelium and is up–regulated by interferon gamma," *J. Am. Soc. Nephrol.*, 4:(5):1140–1150), 1993.

Boyce et al., "Targeting simian virus 40 T antigen to the osteoclast in transgenic mice causes osteoclast tumors and transformation and apoptosis of osteoclasts," *Endo.*, 136(12):5751–5759, 1995.

Brakenhoff et al., "The human E48 antigen, highly homologous to the murine Ly–6 antigen ThB, is a GPI–anchored molecule apparently involved in keratinocyte cell–cell adhesion," *J. Cell. Biol.*, 129:1677–1689, 1995.

Brandi et al., "Bidirectional regulation of osteoclast function by nitric oxide synthase isoforms," *Proc. Natl. Acad. Sci. USA*, 92:2954–2958, 1995.

Chenu et al., "Prostaglandin E$_2$ inhibits formation of osteoclastlike cells in long–term human marrow cultures but is not a mediator of the inhibitory effects of transforming growth factor β," *J. Bone Miner. Res.*, 5(7):677–681, 1990.

Chenu et al., "Transforming growth factor β inhibits formation of osteoclast–like cells in long–term human marrow cultures," *Proc. Natl. Acad. Sci. USA* 85:5683–5687, 1988.

Classon et al., "Mouse stem cell antigen Sca–2 is a member of the Ly–6 family of cell surface proteins," *Proc. Natl. Acad. Sci. USA*, 91:5296–5300, 1994.

Coleman et al., "Osteoclast inhibition for the treatment of bone metastases," *Cancer Treatment Reviews*, 19:79–103, 1993.

Davies et al., "The osteoclast functional antigen, implicated in the regulation of bone resorption, is biochemically related to the vitronectin receptor," *J. Cell Biol.*, 109:1817–1826, 1989.

De La Mata et al., Interleukin–6 enhances hypercalcemia and bone resorption mediated by parathyroid hormone–related protein in vivo, *J. Clin. Invest.*, 95:2846–2852, 1995.

Devlin, et al., "Interleukin–6: A potential mediator of the massive osteolysis in patients with Gorham–Stout disease," *J. Clin. Endo. and Metabolism*, 81(5):1893–1897, 1996.

Devlin et al., "Annexin II increases osteoclast (OCL) formation by stimulating the proliferation of osteoclast precursors in human marrow cultures," *J. Bone Miner. Res.*, 10:S323, (Suppl. 1), ISSN 0884–0431, Abstract No. M283, 1995.

Fisher et al., "Inhibition of osteoclastic bone resorption in vivo by echistatin, an 'Arginyl–Glycly–Asparty' (RGD)–containing protein," *Endo.*, 132(3):1411–1413, 1993.

Fleming et al., "Multiple glycosylphosphatidylinositol–Anchored Ly–6 molecules and transmembrane Ly–6E mediate inhibition of IL–2 production," *J. Immunol*, 153:1955–1962, 1994.

Gallwitz et al., "5–Lipoxygenase metabolites of arachidonic acid stimulate isolated osteoclasts to resorb calcified matrices," *J. Biol. Chem.*, 268(14):10087–10094, 1993.

Jilka et al., "Increased osteoclast development after estrogen loss: Mediation by Interleukin–6," *Science*, 257:88–91, 1992.

Kurihara, et al., "IL–6 stimulates osteoclast–like multinucleated cell formation in long term human marrow cultures by inducing IL–1 release," *J. Immunol.*, 144(11):4226–4230, 1990.

Kurihara et al., "Identification of committed mononuclear precursors for osteoclast–like cells formed in long term human marrow cultures," *Endo.*, 126(5):2733–2741, 1990.

Horowitz et al., "Expression and regulation of Ly–6 differentiation antigens by murine osteoblasts," *Endo.*, 135(3):1032–1043, 1994.

MacDonald et al., "Formation of multinucleated cells that respond to osteotropic hormones in long term human bone marrow cultures," *Endo.*, 120(6):2326–2333, 1987.

Oursler, Merry Jo, "Osteoclast synthesis and secretion and activation of latent transforming growth factor β," *J. Bone Miner. Res.*, 9(4):443–452, 1994.

Reddy et al., "Cloning and characterization of a novel autocrine osteoclast (OCL) stimulating factor (OSF)," *J. Bone Miner. Res.*, 10:S325, (Suppl. 1), ISSN 0884–0431, Abstract No. M292, 1995.

Reddy et al., "Inhibition of tartrate–resistant acid phosphatase gene expression by hemin and protoporphyrin IX. Identification of a hemin–responsive inhibitor of transcription," *Blood*, 88(6):2288–2297, 1996.

Reddy et al., "Characterization of the mouse tartrate–resistant acid phosphatase (TRAP) gene promoter," *J. Bone Miner. Res.*, 10(4):601–606, 1995.

Reddy et al., "Interleukin–6 antisense deoxyoligonucleotides inhibit bone resorption by giant cells from human giant cell tumors of bone," *J. Bone Miner. Res.*, 9(5):753–757, 1994.

Reddy et al., Tartrate–Resistant acid phosphatase gene expression as a facile reporter gene for screening transfection efficiency in mammalian cell cultures, *Bio Techniques* 15(3):444–447, 1993.

Roodman, G.D., "Application of bone marrow cultures to the study of osteoclast formation and osteoclast precursors in man," *Calcif Tissue Int.,* 56(Suppl. 1):S22–S23, 1995.

Simonet et al., "Osteoprotegerin: A novel secreted protein involved in the regulation of bond density," *Cell,* 89:309–319, 1997.

Takahashi et al., "Osteoclast–like cell formation and its regulation by osteotropic hormones in mouse bone marrow cultures." *Endo.,* 122(4):1373–1382, 1988.

Takahashi et al., "Cloning and identification of annexin II as an autocrine/paracrine factor that increases formation and bond resorption," *J. Biol. Chem.,* 269(46):28696–28701, 1994.

Takahashi et al., "Downregulation of calcitonin receptor mRNA expression by calcitonin during human osteoclast–like cell differentiation," *J. Clin. Invest.,* 95:167–171, 1995.

Takahashi et al., "Development and characterization of a human marrow stromal cell line that enhances osteoclast–like cell formation," *Endo.,* 136(4):1441–1449, 1995.

Toshiyuki et al., "Suramin suppresses hypercalcemia and osteoclastic bone resorption in nude mice bearing a human squamous cancer," *Cancer Research,* 55:1989–1993, 1995.

Uy et al., "Use of an in vivo model to determine the effects of interleukin–1 on cells at different stages in the osteoclast lineage," *J. Bone Miner. Res.,* 10(2):295–301, 1995.

Uy et al., "Effects of parathyroid hormone (PTH)–related protein and PTH on osteoclasts and osteoclast precursors in vivo," *Endo.,* 136(8):3207–3212, 1995.

*Primary Examiner*—Sheela Huff
*Attorney, Agent, or Firm*—Arnold, White & Durkee

[57] ABSTRACT

It has been found that two proteins produced by human osteoclasts inhibit osteoclast formation in bone marrow cultures and inhibit bone resorption in a fetal long bone assay. One of the proteins is identical to an Ly6 gene family protein and homologous to the Sca2 antigen, Ly6A. The second, OIP-2, is a novel protein not previously identified. The discovery of the osteoclast inhibition property of the OIP proteins suggests the therapeutic potential for patients with disordered osteoclast activity in such conditions as osteoporosis.

7 Claims, 17 Drawing Sheets

```
GAATTCGGCGGCCGCGGGCCGCTGGTACCTGCCGTCCGGGCGGGGACAGGCTGCTTTGGTTTG      61

TGACCTCCAGGCAGGAGGACGCCATCCTCTCCAGAATGAAGATCTTCTTGCCAGTGCTGCTG     121
                                 MetLysIlePheLeuProValLeuLeu
                                  +95     Cleavable N-terminal GCTGCCCTTCTGGGTGTGGAGCCAGCTCGCTGATGTGCTTCCTGCTTGAACCAG             181
AlaAlaLeuLeuGlyValGluArgAlaSerLeuMetCysPheSerCysLeuAsnGln
   signal peptide (20 amino acids)

AAGAGCAATCTGTACTGCCTGAAGCCGACCATCTGCTCCGACCAGGACAACTACTGCGTG      241
LysSerAsnLeuTyrCysLeuLysProThrIleCysSerAspGlnAspAsnTyrCysVal

ACTGTGTCTGCTAGTGCCGGCATTGGGAATCTCGTGACATTTGGCCACAGCCTGAGCAAG      301
ThrValSerAlaSerAlaGlyIleGlyAsnLeuValThrPheGlyHisSerLeuSerLys

ACCTGTTCCCCGGCCTGCCCCATCCCAGAAGGCGTCAATGTTGGTGGCTTCCATGGGC         361
ThrCysSerProAlaCysProIleProGluGlyValAsnValGlyValAlaSerMetGly

ATCAGCTGCTGCCAGAGCTTTCTGTGCAATTTCAGTGCGGGGCTGCGGGCA                421
IleSerCysCysGlnSerPheLeuCysAsnPheSerAlaAlaAspGlyGlyLeuArgAla
```

FIG. 6A

```
AGCGTCACCCTGCTGGGTGCCGGGGCTGCTGCTGAGCCTGCTGCCGGCCCTGCTGCGGTTT 481
SerValThrLeuLeuGlyAlaGlyLeuLeuLeuSerLeuLeuProAlaLeuLeuArgPhe
                                                    cytoplasmic GGCCCCCTGACCGCGCCCAGACCCTGTCCCCCGATCCCCCAGCTCAGGAAGGAAAGCCCAGCC 541
GlyPro (SEQ ID NO:2)
tail +488

CTTTCTGGATCCCCACAGTGTATGGGAGCCCCTGACTCCTCACGTGCCTGATCTGTGCCCT 601
TGGTCCCAGGTCAGGCTGCCACCCCCAGCTCCACCTGCCCCAGCCCTGCCTCTGCCCC 661
AAGTGGGCCAGCTGCCCTCACTTCTGGGGTGGATGATGTGACCTTCCTTGGGGACTGCG 721
GAAGGGACGAGGGTTCCCCAGGAGTCTTACGGTCCAACATCAGGACCAAGTCCCATGGACA 781
TGCTGACAGGGTCCCCAGGAGAGACCGTGTCAGTAGGGATGTGTGCCTGGCTGTGTACGTG 841
GGTGTGCAGTGCACGTGAGAGAGCCTTCTGGGGCCTTCCTGTAGCCCCTGCCCTGGAGGGAGG 901
TGTGCCAGCAGCCTGGAGTCCCAGTCCCTGGGGTTTCTGCCACTTCCGGGTCTAGGCCCTGCC 961
CACTTCAAGGGCAGCCTTTGGGGTTGGGGTTTGGGGTTCCCTGCCACCCCCACATTGGAGCCCCTGCTTTGG 1021
CCAAATCCAGCCAGTCCTGCCCCCAGCCCCACCCCCACATTGGAGCCCCTGCTTTGG 1081
TGCCTCAAATAAAT (SEQ ID NO:1)
1095          Poly A signal
```

FIG. 6B

```
    ATGGTTTGGAAAGTAGCTGTATTCCTCAGTGTGGCCCTGGGCATTGTGCCGTTCCTATA     60
  1 MetValTrpLysValAlaValPheLeuSerValAlaLeuGlyIleValProIle

GATGATCCTGAAGATGGAGGCAAGCACTGGGTGGTGATCGTGTGGCAGTTCAAATGGCTGG   120
 21 AspAspProGluAspGlyGlyLysHisTrpValValIleValAlaGlySerAsnGlyTrp

TATAATTATAGGCACCAGGCAGACGCGTGCCATGCCTACCAGATCATTCACCGCAATGGG    180
 41 TyrAsnTyrArgHisGlnAlaAspAlaCysHisAlaTyrGlnIleIleHisArgAsnGly

ATTCCTGACGAACAGATCGTTGTGATGATGTACGATGACATTGCTTACTCTGAAGACAAT    240
 61 IleProAspGluGlnIleValValMetMetTyrAspAspIleAlaTyrSerGluAspAsn

CCCACTCCAGGAATTGTGATCAACAGGCCCAATGGCACAGATGTCTATCAGGGAGTCCCG    300
 81 ProThrProGlyIleValIleAsnArgProAsnGlyThrAspValTyrGlnGlyValPro

AAGGACTACACTGGGAGAGGATGTTACCCCACAAAATTCCTTGCTGTGTTGAGAGGCGAT   360
101 LysAspTyrThrGlyGluAspValThrProGlnAsnPheLeuAlaValLeuArgGlyAsp

GCAGAAGCAGTGAAGGGCATAGGATCCGGCAAAGTCCTGAAGAGTGGCCCCCAGGATCAC    420
121 AlaGluAlaValLysGlyIleGlySerGlyLysValLeuLysSerGlyProGlnAspHis

GTGTTCATTTACTTCACTGACCATGGATCTACTGGAATACTGGTTTTCCCAATGAAGAT    480
141 ValPheIleTyrPheThrAspHisGlySerThrGlyIleLeuValPheProAsnGluAsp

CTTCATGTAAAGGACCTGAATGAGACCATTCATTACATGTACAAACACAAAATGTACCGA    540
161 LeuHisValLysAspLeuAsnGluThrIleHisTyrMetTyrLysHisLysMetTyrArg
```

FIG. 15A

```
181  AAGATGGTGTTCTACATTGAAGCCTGTGAGTCTGGGTCCATGATGAACCACCTGCCGGAT  600
     LysMetValPheTyrIleGluAlaCysGluSerGlySerMetMetAsnHisLeuProAsp

201  AACATCAATGTTTATGCAACTACTGCTGCCAACCCAGAGAGTCGTCCTACGCCTGTTAC  660
     AsnIleAsnValTyrAlaThrThrAlaAlaAsnProArgGluSerSerTyrAlaCysTyr

221  TATGATGAGAAGAGGTCCACGTACCTGGGGACTGGTACAGCGTCAACTGGATGGAAGAC  720
     TyrAspGluLysArgSerThrTyrLeuGlyAspTrpTyrSerValAsnTrpMetGluAsp

241  TCGGACGTGGAAGATCTGACTAAAGAGACCCTGCACAAGCAGTACCACCTGGTAAAATCG  780
     SerAspValGluAspLeuThrLysGluThrLeuHisLysGlnTyrHisLeuValLysSer

261  CACACCAACACCAGCCACGTCATGCAGTATGGAAAACAAAACAATTCCACCATGAAAGTG  840
     HisThrAsnThrSerHisValMetGlnTyrGlyAsnLysThrIleSerThrMetLysVal

281  ATGCAGTTTCAGGGTATGAAACGCAAAGCCAGTTCTCCCGTCCTACCTCCAGTCACA  900
     MetGlnPheGlnGlyMetLysArgLysAlaSerSerProValProLeuProProValThr

301  CACCTTGACCTCACCCCAGCCCTGATGTGCCTCTCACCATCATGAAAAGGAAACTGATG  960
     HisLeuAspLeuThrProSerProAspValProLeuThrIleMetLysArgLysLeuMet

321  AACACCAATGATCTGGAGGAGTCCAGGCAGCTCACGGAGGAGATCGAGCTGGAT  1020
     AsnThrAsnAspLeuGluGluSerArgGlnLeuThrGluGluIleGluGlnArgHisLeuAsp
```

FIG. 15B

```
341  GCCAGGCACCTCATTGAGAAGTCAGTGCCTAAGATCGTTCCTTGCTGGCAGCGTCCGAG                1080
     AlaArgHisLeuIleGluLysSerValArgLysIleValSerLeuLeuAlaAlaSerGlu

361  GCTGAGGTGGAGCAGCTCCTGTCCGAGAGCCCCGCTCACGGGCACAGCTGCTACCCA                  1140
     AlaGluValGluGlnLeuLeuSerGluArgAlaProLeuThrGlyHisSerCysTyrPro

381  GAGGCCCTGCTGCACTTCCGACACCCACTGCTTCAACTGGCACTCCCCACGTAGAGTAT               1200
     GluAlaLeuLeuHisPheArgThrHisCysPheAsnTrpHisSerProThrTyrGluTyr

401  GCGTTGAGACATTTGTACGTGCTGGTCAACCTTTGTGAGAAGCCGTATCCGCTTCACAGG              1260
     AlaLeuArgHisLeuTyrValLeuValAsnLeuCysGluLysProTyrProLeuHisArg

421  ATAAAATTGTCCATGGACCACGTGTGCCTTGGTCACTACT    (136 TO 1434 OF SEQ ID NO:3)  1320
     IleLysLeuSerMetAspHisValCysLeuGlyHisTyr   SEQ ID NO:4
```

FIG. 15C though its regulation

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
  (A) LENGTH: 1095 base pairs
  (B) TYPE: nucleic acid
  (C) STRANDEDNESS: single
  (D) TOPOLOGY: linear (ix) FEATURE:
  (A) NAME/KEY: CDS
  (B) LOCATION: 95..487

(xi) SEQUENCE DESCRIPTION: SEQ ID NO:1:

```
GAATTCGCGG CCGCGGCTGC TGGTACCTGC GTCCGCCCGG CGGACAGGCT GCTTTGGTTT      60

GTGACCTCCA GGCAGGACGG CCATCCTCTC CAGA ATG AAG ATC TTC TTG CCA         112
                                     Met Lys Ile Phe Leu Pro
                                       1               5

GTG CTG CTG GCT GCC CTT CTG GGT GTG GAG CGA GCC AGC TCG CTG ATG       160
Val Leu Leu Ala Ala Leu Leu Gly Val Glu Arg Ala Ser Ser Leu Met
            10                  15                  20

TGC TTC TCC TGC TTG AAC CAG AAG AGC AAT CTG TAC TGC CTG AAG CCG       208
Cys Phe Ser Cys Leu Asn Gln Lys Ser Asn Leu Tyr Cys Leu Lys Pro
        25                  30                  35

ACC ATC TGC TCC GAC CAG GAC AAC TAC TGC GTG ACT GTG TCT GCT AGT       256
Thr Ile Cys Ser Asp Gln Asp Asn Tyr Cys Val Thr Val Ser Ala Ser
    40                  45                  50

GCC GGC ATT GGG AAT CTC GTG ACA TTT GGC CAC AGC CTG AGC AAG ACC       304
Ala Gly Ile Gly Asn Leu Val Thr Phe Gly His Ser Leu Ser Lys Thr
55                  60                  65                  70

TGT TCC CCG GCC TGC CCC ATC CCA GAA GGC GTC AAT GTT GGT GTG GCT       352
Cys Ser Pro Ala Cys Pro Ile Pro Glu Gly Val Asn Val Gly Val Ala
            75                  80                  85

TCC ATG GGC ATC AGC TGC TGC CAG AGC TTT CTG TGC AAT TTC AGT GCG       400
Ser Met Gly Ile Ser Cys Cys Gln Ser Phe Leu Cys Asn Phe Ser Ala
        90                  95                  100

GCC GAT GGC GGG CTG CGG GCA AGC GTC ACC CTG CTG GGT GCC GGG CTG       448
Ala Asp Gly Gly Leu Arg Ala Ser Val Thr Leu Leu Gly Ala Gly Leu
    105                 110                 115

CTG CTG AGC CTG CTG CCG GCC CTG CTG CGG TTT GGC CCC TGACCGCCCA        497
Leu Leu Ser Leu Leu Pro Ala Leu Leu Arg Phe Gly Pro
120                 125                 130

GACCCTGTCC CCCGATCCCC CAGCTCAGGA AGGAAAGCCC AGCCCTTTCT GGATCCCACA     557

GTGTATGGGA GCCCCTGACT CCTCACGTGC CTGATCTGTG CCCTTGGTCC CAGGTCAGGC     617

CCACCCCCTG CACCTCCACC TGCCCCAGCC CCTGCCTCTG CCCCAAGTGG GCCAGCTGCC     677

CTCACTTCTG GGGTGGATGA TGTGACCTTC CTTGGGGGAC TGCGGAAGGG ACGAGGGTTC     737

CCTGGAGTCT TACGGTCCAA CATCAGGACC AAGTCCCATG GACATGCTGA CAGGGTCCCC     797

AGGGAGACCG TGTCAGTAGG GATGTGTGCC TGGCTGTGTA CGTGGGTGTG CAGTGCACGT     857

GAGAGCACGT GGCGGCTTCT GGGGGCCATG TTTGGGGAGG GAGGTGTGCC AGCAGCCTGG     917

AGAGCCTCAG TCCCTGTAGC CCCCTGCCCT GGCACAGCTG CATGCACTTC AAGGGCAGCC     977

TTTGGGGGTT GGGGTTTCTG CCACTTCCGG GTCTAGGCCC TGCCCAAAT  CCAGCCAGTC    1037

CTGCCCCAGC CCACCCCCAC ATTGGAGCCC TCCTGCTGCT TTGGTGCCTC AAATAAAT     1095
```

(2) INFORMATION FOR SEQ ID NO:2:

(i) SEQUENCE CHARACTERISTICS:
    (A) LENGTH: 131 amino acids
    (B) TYPE: amino acid
    (D) TOPOLOGY: linear (ii) MOLECULE TYPE: protein (xi) SEQUENCE DESCRIPTION: SEQ ID NO:2:

```
Met Lys Ile Phe Leu Pro Val Leu Leu Ala Ala Leu Leu Gly Val Glu
  1               5                  10                  15

Arg Ala Ser Ser Leu Met Cys Phe Ser Cys Leu Asn Gln Lys Ser Asn
             20                  25                  30

Leu Tyr Cys Leu Lys Pro Thr Ile Cys Ser Asp Gln Asp Asn Tyr Cys
         35                  40                  45

Val Thr Val Ser Ala Ser Ala Gly Ile Gly Asn Leu Val Thr Phe Gly
     50                  55                  60

His Ser Leu Ser Lys Thr Cys Ser Pro Ala Cys Pro Ile Pro Glu Gly
 65                  70                  75                  80

Val Asn Val Gly Val Ala Ser Met Gly Ile Ser Cys Cys Gln Ser Phe
                 85                  90                  95

Leu Cys Asn Phe Ser Ala Ala Asp Gly Gly Leu Arg Ala Ser Val Thr
            100                 105                 110

Leu Leu Gly Ala Gly Leu Leu Leu Ser Leu Leu Pro Ala Leu Leu Arg
        115                 120                 125

Phe Gly Pro
    130
```

(2) INFORMATION FOR SEQ ID NO:3:

(i) SEQUENCE CHARACTERISTICS:
        (A) LENGTH: 1936 base pairs
        (B) TYPE: nucleic acid
        (C) STRANDEDNESS: single
        (D) TOPOLOGY: linear (ix) FEATURE:
        (A) NAME/KEY: CDS
        (B) LOCATION: 136..1434

(xi) SEQUENCE DESCRIPTION: SEQ ID NO:3:

```
TGTGAGGCTG CGAGCCGCCG CGAGTTCTCA CGGTCCCGCC GGCGCCACCA CCGCGGTCAC      60

TCACCGCCGC CGCCGCCACC ACTGCCACCA CGGTCGCCTG CCACAGGTGT CTGCAATTGA     120

ACTCCAAGGT GCAGA ATG GTT TGG AAA GTA GCT GTA TTC CTC AGT GTG GCC      171
               Met Val Trp Lys Val Ala Val Phe Leu Ser Val Ala
                 1               5                  10

CTG GGC ATT GGT GCC GTT CCT ATA GAT GAT CCT GAA GAT GGA GGC AAG      219
Leu Gly Ile Gly Ala Val Pro Ile Asp Asp Pro Glu Asp Gly Gly Lys
             15                  20                  25

CAC TGG GTG GTG ATC GTG GCA GGT TCA AAT GGC TGG TAT AAT TAT AGG      267
His Trp Val Val Ile Val Ala Gly Ser Asn Gly Trp Tyr Asn Tyr Arg
         30                  35                  40

CAC CAG GCA GAC GCG TGC CAT GCC TAC CAG ATC ATT CAC CGC AAT GGG      315
His Gln Ala Asp Ala Cys His Ala Tyr Gln Ile Ile His Arg Asn Gly
     45                  50                  55                  60

ATT CCT GAC GAA CAG ATC GTT GTG ATG ATG TAC GAT GAC ATT GCT TAC      363
Ile Pro Asp Glu Gln Ile Val Val Met Met Tyr Asp Asp Ile Ala Tyr
                 65                  70                  75

TCT GAA GAC AAT CCC ACT CCA GGA ATT GTG ATC AAC AGG CCC AAT GGC      411
Ser Glu Asp Asn Pro Thr Pro Gly Ile Val Ile Asn Arg Pro Asn Gly
             80                  85                  90

ACA GAT GTC TAT CAG GGA GTC CCG AAG GAC TAC ACT GGA GAG GAT GTT      459
Thr Asp Val Tyr Gln Gly Val Pro Lys Asp Tyr Thr Gly Glu Asp Val
         95                 100                 105

ACC CCA CAA AAT TTC CTT GCT GTG TTG AGA GGC GAT GCA GAA GCA GTG      507
Thr Pro Gln Asn Phe Leu Ala Val Leu Arg Gly Asp Ala Glu Ala Val
    110                 115                 120
```

```
AAG GGC ATA GGA TCC GGC AAA GTC CTG AAG AGT GGC CCC CAG GAT CAC        555
Lys Gly Ile Gly Ser Gly Lys Val Leu Lys Ser Gly Pro Gln Asp His
125                 130                 135                 140

GTG TTC ATT TAC TTC ACT GAC CAT GGA TCT ACT GGA ATA CTG GTT TTT        603
Val Phe Ile Tyr Phe Thr Asp His Gly Ser Thr Gly Ile Leu Val Phe
                145                 150                 155

CCC AAT GAA GAT CTT CAT GTA AAG GAC CTG AAT GAG ACC ATC CAT TAC        651
Pro Asn Glu Asp Leu His Val Lys Asp Leu Asn Glu Thr Ile His Tyr
            160                 165                 170

ATG TAC AAA CAC AAA ATG TAC CGA AAG ATG GTG TTC TAC ATT GAA GCC        699
Met Tyr Lys His Lys Met Tyr Arg Lys Met Val Phe Tyr Ile Glu Ala
                175                 180                 185

TGT GAG TCT GGG TCC ATG ATG AAC CAC CTG CCG GAT AAC ATC AAT GTT        747
Cys Glu Ser Gly Ser Met Met Asn His Leu Pro Asp Asn Ile Asn Val
190                 195                 200

TAT GCA ACT ACT GCT GCC AAC CCC AGA GAG TCG TCC TAC GCC TGT TAC        795
Tyr Ala Thr Thr Ala Ala Asn Pro Arg Glu Ser Ser Tyr Ala Cys Tyr
205                 210                 215                 220

TAT GAT GAG AAG AGG TCC ACG TAC CTG GGG GAC TGG TAC AGC GTC AAC        843
Tyr Asp Glu Lys Arg Ser Thr Tyr Leu Gly Asp Trp Tyr Ser Val Asn
                225                 230                 235

TGG ATG GAA GAC TCG GAC GTG GAA GAT CTG ACT AAA GAG ACC CTG CAC        891
Trp Met Glu Asp Ser Asp Val Glu Asp Leu Thr Lys Glu Thr Leu His
            240                 245                 250

AAG CAG TAC CAC CTG GTA AAA TCG CAC ACC AAC ACC AGC CAC GTC ATG        939
Lys Gln Tyr His Leu Val Lys Ser His Thr Asn Thr Ser His Val Met
                255                 260                 265

CAG TAT GGA AAC AAA ACA ATC TCC ACC ATG AAA GTG ATG CAG TTT CAG        987
Gln Tyr Gly Asn Lys Thr Ile Ser Thr Met Lys Val Met Gln Phe Gln
270                 275                 280

GGT ATG AAA CGC AAA GCC AGT TCT CCC GTC CCC CTA CCT CCA GTC ACA       1035
Gly Met Lys Arg Lys Ala Ser Ser Pro Val Pro Leu Pro Pro Val Thr
285                 290                 295                 300

CAC CTT GAC CTC ACC CCC AGC CCT GAT GTG CCT CTC ACC ATC ATG AAA       1083
His Leu Asp Leu Thr Pro Ser Pro Asp Val Pro Leu Thr Ile Met Lys
                305                 310                 315

AGG AAA CTG ATG AAC ACC AAT GAT CTG GAG GAG TCC AGG CAG CTC ACG       1131
Arg Lys Leu Met Asn Thr Asn Asp Leu Glu Glu Ser Arg Gln Leu Thr
            320                 325                 330

GAG GAG ATC CAG CGG CAT CTG GAT GCC AGG CAC CTC ATT GAG AAG TCA       1179
Glu Glu Ile Gln Arg His Leu Asp Ala Arg His Leu Ile Glu Lys Ser
                335                 340                 345

GTG CGT AAG ATC GTC TCC TTG CTG GCA GCG TCC GAG GCT GAG GTG GAG       1227
Val Arg Lys Ile Val Ser Leu Leu Ala Ala Ser Glu Ala Glu Val Glu
350                 355                 360

CAG CTC CTG TCC GAG AGA GCC CCG CTC ACG GGG CAC AGC TGC TAC CCA       1275
Gln Leu Leu Ser Glu Arg Ala Pro Leu Thr Gly His Ser Cys Tyr Pro
365                 370                 375                 380

GAG GCC CTG CTG CAC TTC CGG ACC CAC TGC TTC AAC TGG CAC TCC CCC       1323
Glu Ala Leu Leu His Phe Arg Thr His Cys Phe Asn Trp His Ser Pro
                385                 390                 395

ACG TAC GAG TAT GCG TTG AGA CAT TTG TAC GTG CTG GTC AAC CTT TGT       1371
Thr Tyr Glu Tyr Ala Leu Arg His Leu Tyr Val Leu Val Asn Leu Cys
            400                 405                 410

GAG AAG CCG TAT CCG CTT CAC AGG ATA AAA TTG TCC ATG GAC CAC GTG       1419
Glu Lys Pro Tyr Pro Leu His Arg Ile Lys Leu Ser Met Asp His Val
                415                 420                 425

TGC CTT GGT CAC TAC TGAAGAGCTG CCTCCTGGAA GCTTTTCCAA GTGTGAGCGC       1474
Cys Leu Gly His Tyr
            430
```

```
CCCACCGACT GTGTGCTGAT CAGAGACTGG AGAGGTGGAG TGAGAAGTCT CCGCTGCTCG    1534

GGCCCTCCTG GGGAGCCCCC GCTCCAGGGC TCGCTCCAGG ACCTTCTTCA CAAGATGACT    1594

TGCTCGCTGT TACCTGCTTC CCCAGTCTTT TCTGAAAAAC TACAAATTAG GGTGGGAAAA    1654

GCTCTGTATT GAGAAGGGTC ATATTTGCTT TCTAGGAGGT TTGTTGTTTT GCCTGTTAGT    1714

TTTGAGGAGC AGGAAGCTCA TGGGGGCTTC TGTAGCCCCT CTCAAAAGGA GTCTTTATTC    1774

TGAGAATTTG AAGCTGAAAC CTCTTTAAAT CTTCAGAATG ATTTTATTGA AGAGGCCGCA    1834

AGCCCCAAAT GGAAAACTGT TTTTAGAAAA TATGATGATT TTTGATTGCT TTTGTATTTA    1894

ATTCTGCAGG TGTTCAAGTC TTAAAAAATA AAGATTTATA AA                      1936
```

(2) INFORMATION FOR SEQ ID NO:4:

(i) SEQUENCE CHARACTERISTICS:
        (A) LENGTH: 433 amino acids
        (B) TYPE: amino acid
        (D) TOPOLOGY: linear (ii) MOLECULE TYPE: protein (xi) SEQUENCE DESCRIPTION: SEQ ID NO:4:

```
Met Val Trp Lys Val Ala Val Phe Leu Ser Val Ala Leu Gly Ile Gly
 1               5                  10                  15

Ala Val Pro Ile Asp Asp Pro Glu Asp Gly Lys His Trp Val Val
                20                  25                  30

Ile Val Ala Gly Ser Asn Gly Trp Tyr Asn Tyr Arg His Gln Ala Asp
                35                  40                  45

Ala Cys His Ala Tyr Gln Ile Ile His Arg Asn Gly Ile Pro Asp Glu
    50                  55                  60

Gln Ile Val Val Met Met Tyr Asp Asp Ile Ala Tyr Ser Glu Asp Asn
65                  70                  75                  80

Pro Thr Pro Gly Ile Val Ile Asn Arg Pro Asn Gly Thr Asp Val Tyr
                85                  90                  95

Gln Gly Val Pro Lys Asp Tyr Thr Gly Glu Asp Val Thr Pro Gln Asn
                100                 105                 110

Phe Leu Ala Val Leu Arg Gly Asp Ala Glu Ala Val Lys Gly Ile Gly
            115                 120                 125

Ser Gly Lys Val Leu Lys Ser Gly Pro Gln Asp His Val Phe Ile Tyr
    130                 135                 140

Phe Thr Asp His Gly Ser Thr Gly Ile Leu Val Phe Pro Asn Glu Asp
145                 150                 155                 160

Leu His Val Lys Asp Leu Asn Glu Thr Ile His Tyr Met Tyr Lys His
                165                 170                 175

Lys Met Tyr Arg Lys Met Val Phe Tyr Ile Glu Ala Cys Glu Ser Gly
                180                 185                 190

Ser Met Met Asn His Leu Pro Asp Asn Ile Asn Val Tyr Ala Thr Thr
    195                 200                 205

Ala Ala Asn Pro Arg Glu Ser Ser Tyr Ala Cys Tyr Tyr Asp Glu Lys
    210                 215                 220

Arg Ser Thr Tyr Leu Gly Asp Trp Tyr Ser Val Asn Trp Met Glu Asp
225                 230                 235                 240

Ser Asp Val Glu Asp Leu Thr Lys Glu Thr Leu His Lys Gln Tyr His
                245                 250                 255

Leu Val Lys Ser His Thr Asn Thr Ser His Val Met Gln Tyr Gly Asn
                260                 265                 270
```

```
Lys Thr Ile Ser Thr Met Lys Val Met Gln Phe Gln Gly Met Lys Arg
        275             280             285

Lys Ala Ser Ser Pro Val Pro Leu Pro Pro Val Thr His Leu Asp Leu
        290             295             300

Thr Pro Ser Pro Asp Val Pro Leu Thr Ile Met Lys Arg Lys Leu Met
305                 310             315                 320

Asn Thr Asn Asp Leu Glu Glu Ser Arg Gln Leu Thr Glu Glu Ile Gln
                325             330             335

Arg His Leu Asp Ala Arg His Leu Ile Glu Lys Ser Val Arg Lys Ile
                340             345             350

Val Ser Leu Leu Ala Ala Ser Glu Ala Glu Val Glu Gln Leu Leu Ser
        355             360             365

Glu Arg Ala Pro Leu Thr Gly His Ser Cys Tyr Pro Glu Ala Leu Leu
        370             375             380

His Phe Arg Thr His Cys Phe Asn Trp His Ser Pro Thr Tyr Glu Tyr
385                 390             395                 400

Ala Leu Arg His Leu Tyr Val Leu Val Asn Leu Cys Glu Lys Pro Tyr
                405             410             415

Pro Leu His Arg Ile Lys Leu Ser Met Asp His Val Cys Leu Gly His
                420             425             430

Tyr
```

COMPOSITIONS AND METHODS OF USE FOR OSTEOCLAST INHIBITOR FACTORS This is a divisional of co-pending application Ser. No. 08/772,441 filed Dec. 20, 1996.

The government owns rights in the present invention pursuant to grant number AG13625 from the National Institutes of Health.

1.0 BACKGROUND OF THE INVENTION

1.1 Field of the Invention

The invention relates to the field of hematology and medicine. In particular, the invention relates to novel methods of treatment and compositions that are useful in inhibiting osteoclast formation and bone resorption.

1.2 Description of the Related Art

Enhanced osteoclast (OCL) activity plays a major role in the pathogenesis of postmenopausal osteoporosis, Paget's disease of bone and hypercalcemia of malignancy. These important clinical problems are associated with significant morbidity or mortality and affect more than 10 million patients in the United States. However, only a limited number of agents that inhibit OCL formation or bone resorption are available and, for most, their mechanisms of action are unknown. Furthermore, many of these agents have significant side effects that limit their utility. Thus, there exists a need for the identification and characterization of inhibitors of osteoclast formation and bone resorption in the continuing search to provide major therapeutic benefits for these patients.

1.2.1 Regulation of osteoclast activity—The osteoclast (OCL) is the primary bone-resorbing cell whose activity is critical for maintaining normal bone turnover (Mundy and Roodman, 1987). Increased morbidity and mortality are seen in patients with diseases associated with increased OCL activity and/or formation. These include fractures in patients with postmenopausal osteoporosis, abnormal bone remodeling in Paget's disease of bone, and bone destruction and life-threatening hypercalcemia in patients with malignancies. These pathologic conditions affect more than 10 million patients in the U.S. at an annual cost of more than 10 billion dollars.

Although much has been learned about factors that regulate osteoclastic bone resorption and OCL formation from rodent bone marrow and organ cultures, it is unclear if all of these studies are directly applicable to man (Takahashi et al., 1988). For example, prostaglandin E2 is a potent stimulator of OCL formation and OCL-induced bone resorption in rodent systems, but inhibits OCL formation in human marrow culture systems (Chenu et al., 1990). Similarly, IL-6 has little or no effect on OCL formation in rodent systems, unless it is present at concentrations of at least 20 ng/ml (Al-Humidan et al., 1991). In contrast, low concentrations of IL-6 (10–100 pg/ml) significantly increase human OCL formation, and IL-6 plays a critical role in human osteoclastic bone resorption (Kurihara et al., 1990). Thus, studies using human systems are important to understanding both the regulation of OCL activity in man and for development of rational therapies to combat these important health problems in the United States.

1.2.2 Inhibition of Osteoclast Activity—The currently available substances that inhibit osteoclast formation and/or osteoclastic bone resorption have limited utility, and many of these have significant side effects. Calcitonin, a peptide hormone secreted by C cells of the thyroid in response to elevated serum calcium, is a well-characterized inhibitor of OCL formation and bone resorption (Friedman et al., 1965). However, chronic exposure to calcitonin leads to loss of its inhibitory effects on OCL through down regulation of the calcitonin receptor MRNA and calcitonin receptors on OCL surface resulting in an "escape phenomenon" (Takahashi et al., 1995).

Similarly, TGF-β and echistatin, a snake venom that contains an RGD sequence, blocks bone resorption in vitro (Fisher et al., 1993). However, TGF-β and echistatin lack specificity, and echistatin blocks platelet adhesion, thereby potentially resulting in life-threatening bleeding. Monoclonal antibodies, such as 23c6, 121f, or K20 which bind antigens expressed on the OCL surface, can also block OCL bone resorptive activity (Davies et al., 1989; Hentunen et al., 1991; Weber et al., 1990). However, these murine proteins may only have limited value, since they can induce an immune response in patients. Bisphosphonates also inhibit osteoclast activity (Coleman et al, 1993), but there are problems with absorption of oral bisphosphonates, and they frequently induce gastrointestinal discomfort. Since bisphosphonates remain in the bone for years, they have the potential of blocking the normal bone repair mechanisms if too much is taken for too long.

Immune cell products such as interferon-gamma (IFN-γ), interferon-α (IFN-α), oncostatin M, and chemotherapeutic agents such as taxol and suramine, and nitric oxide have been shown to inhibit OCL bone-resorbing activity (Hall et al., 1995; Brandi et al., 1995; Yoneda et al, 1995) and are inhibitors of osteoclastic bone resorption in vitro and in vivo (Yoneda et al, 1995). However, all of these agents have significant side effects which limit their utility Nitric oxide can induce vasodilation and low blood pressure while interferons may induce a flu-like illness. Chemotherapeutic agents frequently have severe toxicities associated with gastrointestinal or hematopoietic side effects.

17 β-Estradiol is also a well-known inhibitor of OCL bone resorption (Jilka et al., 1992), possibly through its regulation of IL-6, IL-1 or TNF-α production. Similarly, retinoic acid has also been shown to inhibit chick OCL bone resorptive activity (O'Neill et al., 1992). Unfortunately, these compounds all have systemic effects which make them less acceptable for use in patients. For example, long-term estrogen therapy in some individuals poses an increased risk of breast or uterine cancer. Thus, there remains a need to develop novel classes of specific inhibitors of OCL activity which will have important therapeutic potential for conditions associated with increased bone destruction.

1.2.3 Identification of the osteoclast as a secretory cell—It has recently been demonstrated that the OCL is a secretory cell that produces factors, such as IL-6, IL-1, and TGFβ, that regulate its formation and activity (Ohsaki et al., 1992; Ousler et al., 1994). Initially, IL-6 was the first factor found to be an autocrine factor produced by OCL, which enhances both OCL formation and bone resorption (Kurihara et al., 1990), a finding that opened a new area of research, autocrine regulation of OCL activity. IL-6 is also produced by OCL-like giant cells isolated from human giant cell tumors, and these cells express IL-6 receptors. The giant cells are not transformed and appear to be highly activated human OCL (Goldring et al., 1986). Furthermore, it has been demonstrated that blocking the activity of IL-6 with antisense deoxyoligonucleotide constructs to IL-6 markedly inhibits the bone-resorbing capacity of OCL-like giant cells (Reddy et al., 1994).

In addition to stimulators of OCL activity, OCLs have been reported to produce inhibitors of OCL activity. Ousler et al. (1994) have shown that latent TGF-β is produced by OCL, which is then activated in the bone microenvironment. Pfeilschifter et al. (1987) have shown that latent TGF-β is a potent inhibitor of all stages of OCL formation. However, little is known about OCL inhibitors or the points along the pathway they may be controlling.

1.2.4 Ly6 Gene Family—The Ly6 gene family represents a class of molecules thought to have particular importance in osteoclast-osteoblast interactions. Horowitz and coworkers (Horowitz et al., 1994) have shown that primary osteoblasts and MC3T3 cells constitutively both Ly6A (Sca1) and Ly6C antigens, both members of the Ly6 multigene family. Ly6C was less abundantly expressed than Ly6A. Ly6A expression was increased by pretreating the cells with interferons. These investigators suggested that the Ly6 molecule was a differentiation antigen restricted to mature osteoblasts.

The Ly6 gene family has been characterized predominantly in murine systems. The majority of these molecules are expressed on lymphocytes, but others have a much wider tissue distribution. Common features of the murine Ly6 gene family include phosphatidylinositol glycan-linkage to the plasma membrane, interferon inducibility and a predicted protein structure similar to α-bungarotoxin. These proteins have a characteristic pattern of 8–10 highly conserved cysteine residues and a β-pleated sheet structure. The murine Ly6 locus contains DNA sequences for at least four distinct genes, Ly6A, Ly6C, Ly6F, and Ly6G. Each gene is characterized by a unique pattern of tissue expression. The murine antigen, Sca1, is identical to the Ly6A.2 gene and is expressed on pluripotent murine hematopoietic stem cells. This antigen has been used to enrich hematopoietic stem cells for transplantation and cell biological studies.

Previously only one human Ly6 gene family was known, E48, which is identical to the mouse THB gene. It is a GPI-anchored molecule which is apparently involved in karytinocyte cell-to-cell adhesion (Brackenhoff et al., 1995). Recently, two other members of the human Ly6 family have been identified. One of these is the human TSA-1 gene which is the human homologue of the Sca2 which is expressed on murine hematopoietic stem cells, and another human homologue for the Sca2 gene which was recently patented by Cohen and Langrid (U.S. Pat. No. 5,468,612). No biologic function for either of these new human Ly6 family members was reported.

2.0 SUMMARY OF THE INVENTION

The present invention addresses the above and other deficiencies in the prior art and particularly the need for identification and characterization of inhibitors of osteoclast formation and bone resorption. As a result of identifying the osteoclastic inhibitory properties of a Ly6-related proteins, the present invention allows development of osteoclast inhibitory factors that have therapeutic potential for patients with a wide range of osteoclast activity disorders. In particular, it has been shown that the Osteoclast Inhibitory Proteins (OIPs) identified by the inventors have utility in inhibiting release of calcium from bone and in inhibiting osteoclast formation.

In particular, the inventors have cloned osteoclast inhibitory peptides, OIPs, from a human osteoblast library, one of which is homologous to human Sca2 antigen Ly6A which is a glycoinositol phospholipid (GPI)-anchored protein in the outer membrane of the cell. Using expression cloning techniques, it has been demonstrated that OIPs are potent inhibitors of human and murine osteoclast formation and osteoclastic bone resorption in organ cultures. This is the first demonstration of a biologic function for Ly6 gene family members in bone. The OIP proteins are factors that occur both in membrane-bound and soluble forms, like M-CSF or TGF-α, but in contrast to these stimulatory factors, inhibit osteoclast formation and/or bone resorption. OIPs thus represent a novel class of osteoclast inhibitors which appear to have important local actions in regulating osteoclast activity. The demonstration of Ly6A on the surface of the osteoblast indicates the important physiologic role in regulating normal bone remodeling played by this class of mole cules.

2.1 Methods of Treatment

An important aspect of the invention is the ability of OIP proteins to inhibit osteoclast production, as demonstrated by the inhibition of osteoclast formation in mammalian cell cultures. Thus there are various methods of treatment that are envisioned to be particularly applicable to such conditions as postmenopausal osteoporosis, Paget's disease of bone, bone metastases and destructive rheumatoid arthritis.

Another aspect of the invention is a method of preventing calcium release from bone. This is expected to be particularly useful for subjects at risk in the general populaton to develop osteoporosis. Prophylactic treatment is considered important in certain opulations at risk such as young females with a family history of osteoporosis, particularly those who are thin and small-boned and/or have a history of tobacco addiction. Other groups include elderly men and women who tend to be prone to bone fracture, particularly hip fractures.

OIP preparations may be administered in several ways, either locally or system ally in pharmaceutically acceptable formulations. Amounts appropriate for administration are determined on an individual basis depending on such factors as age and sex of the subject, as well as physical condition and weight. Such determinations are well within the skill of the practitioner in the medical field.

Other methods of administration may include transfection of OIP cDNAs into autologous marrow stromal cells driven by an appropriate promoter such as CMV. Such preparations could be injected directly into lesions or transplanted into patients for systemic therapy. Gene therapy techniques are currently well past the initial development stage and have shown promise as effective therapies.

It is further contemplated that compounds that specifically bind to OIP receptors will find use as therapeutic agents by blocking bone resorption. Such inhibitors are readily screened once OIP receptors have been identified This may be achieved using, for example, phage display libraries.

2.2 OIP Genes

As known to those of skill in the art, the original source of a recombinant gene or DNA segment to be used in a therapeutic regimen need not be of the same species as the animal to be treated. In this regard, it is contemplated that any recombinant OIP gene may be employed in the methods disclosed herein such as the identification of cells containing DNA encoding OIP or variants of OIP.

Particularly preferred genes are those isolated from humans. However, since the sequence homology for genes encoding OIP polypeptides is expected to be conserved across species lines, equine, murine, and bovine species may also be contemplated as sources, in that such genes and DNA segments are readily available, with the human or murine forms of the gene being most preferred for use in human treatment regimens. Recombinant proteins and polypeptides encoded by isolated DNA segments and genes are often referred to with the prefix "r" for recombinant and "rh" for recombinant human. As such, DNA segments encoding rOIPs, or rOIP-related genes, etc. are contemplated to be particularly useful in connection with this invention. Any recombinant OIP gene would likewise be very useful with the methods of the invention.

Isolation of the DNA encoding OIP polypeptides allows one to use methods well known to those of skill in the art and as herein described to make changes in the codons for specific amino acids such that the codons are "preferred usage" codons for a given species. Thus for example, preferred codons will vary significantly for bacterial species as compared with mammalian species; however, there are preferences even among related species. Shown below are preferred codon usage tables for rat and human. Isolation of rat DNA encoding OIP will allow substitutions for preferred human codons, although expressed polypeptide product from human DNA is expected to be highly homologous to mammalian OIP and so would be expected to be structurally and functionally equivalent to OIP isolated from rat.

TABLE 1

*Rattus rattus*

| Codon | $v^b$ | Total #$^a$ | Codon | $v^b$ | Total #$^a$ | Codon | $v^a$ | Total #$^a$ | Codon | $v^b$ | Total #$^a$ |
|---|---|---|---|---|---|---|---|---|---|---|---|
| UUU | 15.7 | 1972 | UCU | 14.5 | 1717 | UAU | 11.8 | 1393 | UGU | 9.9 | 1167 |
| UUC | 24.5 | 2989 | UCC | 18.7 | 2212 | UAC | 18.6 | 2198 | UGC | 13.0 | 1538 |
| UUA | 5.1 | 605 | UCA | 9.7 | 1150 | UAA | 0.8 | 92 | UGA | 1.0 | 122 |
| UUG | 12.1 | 1425 | UCG | 3.9 | 461 | UAG | 0.4 | 53 | UGG | 13.7 | 1612 |
| CUU | 11.5 | 1361 | CCU | 16.9 | 1995 | CAU | 8.7 | 1031 | CGU | 5.1 | 600 |
| CUC | 20.9 | 2462 | CCC | 19.0 | 2238 | CAC | 15.5 | 1827 | CGC | 10.6 | 1251 |
| CUA | 6.8 | 801 | CCA | 15.5 | 1833 | CAA | 9.9 | 1174 | CGA | 6.6 | 779 |
| CUG | 41.4 | 4890 | CCG | 6.4 | 754 | CAG | 32.2 | 3802 | CGG | 10.7 | 1264 |
| AUU | 15.7 | 1848 | ACU | 12.8 | 1515 | AAU | 14.6 | 1720 | AGU | 10.3 | 1221 |
| AUC | 28.2 | 3327 | ACC | 22.5 | 2660 | AAC | 22.5 | 2656 | AGC | 17.7 | 2094 |
| AUA | 5.8 | 686 | ACA | 14.3 | 1688 | AAA | 20.7 | 2441 | AGA | 9.9 | 1163 |
| AUG | 23.9 | 2822 | ACG | 6.5 | 763 | AAG | 37.0 | 4370 | AGG | 10.6 | 1247 |
| GUU | 10.0 | 1176 | GCU | 20.0 | 2363 | GAU | 20.4 | 2408 | GGU | 11.8 | 1396 |
| GUC | 16.9 | 2000 | GCC | 28.5 | 3368 | GAC | 29.0 | 3419 | GGC | 23.5 | 2779 |
| GUA | 6.6 | 777 | GCA | 13.8 | 1630 | GAA | 25.0 | 2946 | GGA | 15.5 | 1828 |
| GUG | 31.3 | 3692 | GCG | 6.4 | 753 | GAG | 41.1 | 4853 | GGG | 14.9 | 1762 |
| Coding GC 52.97% | | | 1st letter GC 55.24% | | | 2nd letter GC 41.44% | | | 3rd letter GC 62.22% | | |

$^a$Total 118048 codons
$^b$v = Frequency per 1000

TABLE 2

*Homo sapiens*

| Codon | $v^b$ | Total #$^a$ | Codon | $v^b$ | Total #$^a$ | Codon | $v^a$ | Total #$^a$ | Codon | $v^b$ | Total #$^a$ |
|---|---|---|---|---|---|---|---|---|---|---|---|
| UUU | 16.6 | 72711 | UCU | 14.0 | 62953 | UAU | 12.3 | 55039 | UGU | 9.5 | 42692 |
| UUC | 21.4 | 95962 | UCC | 17.7 | 79482 | UAC | 17.0 | 76480 | UGC | 12.8 | 57368 |
| UUA | 6.3 | 28202 | UCA | 10.7 | 48225 | UAA | 0.7 | 2955 | UGA | 1.2 | 5481 |
| UUG | 11.5 | 51496 | UCG | 4.4 | 19640 | UAG | 0.5 | 2181 | UGG | 13.5 | 59982 |
| CUU | 11.7 | 52401 | CCU | 16.7 | 74975 | CAU | 9.6 | 43193 | CGU | 4.6 | 20792 |
| CUC | 19.5 | 87696 | CCC | 20.0 | 89974 | CAC | 14.6 | 65533 | CGC | 11.0 | 49507 |
| CUA | 6.3 | 28474 | CCA | 16.2 | 72711 | CAA | 11.4 | 51146 | CGA | 5.9 | 26551 |
| CUG | 40.6 | 182139 | CCG | 6.9 | 30863 | CAG | 33.7 | 151070 | CGG | 11.3 | 50682 |
| AUU | 15.7 | 70652 | ACU | 12.8 | 57288 | AAU | 16.6 | 74401 | AGU | 11.1 | 49894 |
| AUC | 23.7 | 106390 | ACC | 21.1 | 94793 | AAC | 21.1 | 94725 | AGC | 19.1 | 85754 |
| AUA | 6.7 | 30139 | ACA | 14.7 | 66136 | AAA | 23.2 | 104221 | AGA | 10.8 | 48369 |
| AUG | 22.6 | 101326 | ACG | 6.7 | 30059 | AAG | 33.9 | 152179 | AGG | 10.9 | 48882 |
| GUU | 10.6 | 47805 | GCU | 18.7 | 83800 | GAU | 22.0 | 98712 | GCU | 11.2 | 50125 |
| GUC | 15.6 | 70189 | GCC | 29.2 | 130966 | GAC | 27.0 | 121005 | GGC | 24.0 | 107571 |
| GUA | 6.6 | 29659 | GCA | 15.3 | 68653 | GAA | 27.8 | 124852 | GGA | 16.9 | 75708 |
| GUG | 30.0 | 134750 | GCG | 7.5 | 33759 | GAG | 40.8 | 182943 | GGG | 16.7 | 74859 |
| Coding GC 52.96% | | | 1st letter GC 55.98% | | | 2nd letter GC 42.29% | | | 3rd letter GC 60.60% | | |

$^a$Total 4489120
$^b$v = Frequency per 1000

The definition of a "OIP gene", as used herein, is a gene that hybridizes, under relatively stringent hybridization conditions (see, e.g., Maniatis et al., 1982), to DNA sequences presently known to include related gene sequences.

To prepare an OIP gene segment or cDNA one may follow the teachings disclosed herein and also the teachings of any of patents or scientific documents specifically referenced herein. One may obtain a rOIP- or other related-encoding DNA segments using molecular biological techniques, such as polymerase chain reaction (PCR) or screening of a cDNA or genomic library, using primers or probes with sequences based on the above nucleotide sequence. Such fragments may be readily prepared by, for example, directly synthesizing the fragment by chemical means, by application of nucleic acid reproduction technology, such as the PCR technology of U.S. Pat. Nos. 4,683,195 and 4,683,202 (herein incorporated by reference). The practice of these techniques is a routine matter for those of skill in the art, as taught in various scientific texts (see e.g., Sambrook et al., 1989), incorporated herein by reference. Certain documents further particularly describe suitable mammalian expression vectors, e.g., U.S. Pat. No. 5,168,050, incorporated herein by reference. The OIP genes and DNA segments that are particularly preferred for use in certain aspects of the present methods are those encoding OIP and OIP-related polypeptides.

It is also contemplated that one may clone additional genes or cDNAs that encode a osteoclast inhibitory factor peptide, protein or polypeptide. The techniques for cloning DNA molecules, i.e., obtaining a specific coding sequence from a DNA library that is distinct from other portions of DNA, are well known in the art. This can be achieved by, for example, screening an appropriate DNA library which relates to the cloning of a chemokine gene such as OIP. The screening procedure may be based on the hybridization of oligonucleotide probes, designed from a consideration of portions of the amino acid sequence of known DNA sequences encoding related cytokine proteins. The operation of such screening protocols are well known to those of skill in the art and are described in detail in the scientific literature, for example, see Sambrook et al, 1989.

Techniques for introducing changes in nucleotide sequences that are designed to alter the functional properties of the encoded proteins or polypeptides are well known in the art, e.g., U.S. Pat. No. 4,518,584, incorporated herein by reference, which techniques are also described in further detail herein. Such modifications include the deletion, insertion or substitution of bases, and thus, changes in the amino acid sequence. Changes may be made to increase the osteoclast-inhibiting activity of a protein, to increase its biological stability or half-life, to change its glycosylation pattern, and the like. All such modifications to the nucleotide sequences are encompassed by this invention.

2.3 OIP-Encoding DNA Segments

The present invention, in a general and overall sense, also concerns the isolation and characterization of a novel gene, oip, which encodes the novel osteoclast inhibiting polypeptide, OIP-2. A preferred embodiment of the present invention is a purified nucleic acid segment that encodes a protein that has at least a partial amino acid sequence in accordance with SEQ ID NO:4. Another embodiment of the present invention is a purified nucleic acid segment, further defined as including a nucleotide sequence in accordance with SEQ ID NO:3.

In a more preferred embodiment the purified nucleic acid segment consists essentially of the nucleotide sequence of SEQ ID NO:3, its complement and the degenerate variants thereof. As used herein, the term "nucleic acid segment" and "DNA segment" are used interchangeably and refer to a DNA molecule which has been isolated free of total genomic DNA of a particular species. Therefore, a "purified" DNA or nucleic acid segment as used herein, refers to a DNA segment which contains an OIP coding sequence yet is isolated away from, or purified free from, total genomic DNA, for example, total cDNA or human genomic DNA. Included within the term "DNA segment", are DNA segments and smaller fragments of such segments, and also recombinant vectors, including, for example, plasmids, cosmids, phage, viruses, and the like.

Similarly, a DNA segment comprising an isolated or purified oip-2 gene refers to a DNA segment including OIP coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences, cDNA sequences or combinations thereof. "Isolated substantially away from other coding sequences" means that the gene of interest, in this case oip-2, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode an oip gene, that includes within its amino acid sequence an amino acid sequence in accordance with SEQ ID NO:4. Moreover, in other particular embodiments, the invention concerns isolated DNA segments and recombinant vectors incorporating DNA sequences which encode a gene that includes within its amino acid sequence the amino acid sequence of an oip-2 gene corresponding to murine oip.

Another preferred embodiment of the present invention is a purified nucleic acid segment that encodes a protein in accordance with SEQ ID NO:4, further defined as a recombinant vector. As used herein the term, "recombinant vector", refers to a vector that has been modified to contain a nucleic acid segment that encodes an OIP protein, or a fragment thereof. The recombinant vector may be further defined as an expression vector comprising a promoter operatively linked to said OIP-encoding nucleic acid segment.

A further preferred embodiment of the present invention is a host cell, made recombinant with a recombinant vector comprising an oip-2 gene. The recombinant host cell may be a prokaryotic cell. In a more preferred embodiment, the recombinant host cell is a eukaryotic cell. As used herein, the term "engineered" or "recombinant" cell is intended to refer to a cell into which a recombinant gene, such as a gene encoding OIP, has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (i.e., they will not contain introns), a copy of a genomic gene, or will include genes positioned adjacent to a promoter not naturally associated with the particular introduced gene.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

In certain embodiments, the invention concerns isolated DNA segments and recombinant vectors which encode a protein or peptide that includes within its amino acid sequence an amino acid sequence essentially as set forth in SEQ ID NO:4. Naturally, where the DNA segment or vector encodes a full length OIP protein, or is intended for use in expressing the OIP protein, the most preferred sequences are those which are essentially as set forth in SEQ ID NO:4. It is recognized that SEQ ID NO:4 represents the full length protein encoded by the oip gene and that contemplated embodiments include up to the full length sequence and functional variants as well.

The term "a sequence essentially as set forth in SEQ ID NO:4" means that the sequence substantially corresponds to a portion of SEQ ID NO:4 and has relatively few amino acids which are not identical to, or a biologically functional equivalent of, the amino acids of SEQ ID NO:4. The term "biologically functional equivalent" is well understood in the art and is further defined in detail herein, as a gene having a sequence essentially as set forth in SEQ ID NO:3 and that is associated with a constitutively-produced osteoclast-inhibiting factor in the OIP family. Accordingly, sequences which have between about 70% and about 80%; or more preferably, between about 81% and about 90%; or even more preferably, between about 91% and about 99%; of amino acids which are identical or functionally equivalent to the amino acids of SEQ ID NO:4 will be sequences which are "essentially as set forth in SEQ ID NO:4".

In certain other embodiments, the invention concerns isolated DNA segments and recombinant vectors that include within their sequence a nucleic acid sequence essentially as set forth in SEQ ID NO:3. The term "essentially as set forth in SEQ ID NO:3," is used in the same sense as described above and means that the nucleic acid sequence substantially corresponds to a portion of SEQ ID NO:3, and has relatively few codons which are not identical, or functionally equivalent, to the codons of SEQ ID NO:3. The term "functionally equivalent codon" is used herein to refer to codons that encode the same amino acid, such as the six codons for arginine or serine, as set forth in Table 1, and also refers to codons that encode biologically equivalent amino acids.

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

Excepting intronic or flanking regions, and allowing for the degeneracy of the genetic code, sequences which have between about 70% and about 80%; or more preferably, between about 80%, 85% and about 90%; or even more preferably, between about 90%, 95% and about 99%; of nucleotides which are identical to the nucleotides of SEQ ID NO:3 will be sequences which are "essentially as set forth in SEQ ID NO:3". Sequences which are essentially the same as those set forth in SEQ ID NO:3 may also be functionally defined as sequences which are capable of hybridizing to a nucleic acid segment containing the complement of SEQ ID NO:3 under relatively stringent conditions or conditions of high stringency. Suitable relatively stringent hybridization conditions will be well known to those of skill in the art and are clearly set forth herein, for example conditions for use with Southern and Northern blot analysis, and as described in the examples herein set forth.

Naturally, the present invention also encompasses DNA segments which are complementary, or essentially complementary, to the sequence set forth in SEQ ID NO:3. Nucleic acid sequences which are "complementary" are those which are capable of base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment of SEQ ID NO:3 under relatively stringent conditions, i.e., conditions of high stringency.

The nucleic acid segments of the present invention, regardless of the length of the coding sequence itself, may be combined with other DNA sequences, such as promoters, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to SEQ ID NO:3, such as about 10 to 15 or 20, 30, or 40 or so nucleotides, and which are up to 2000 or so base pairs in length. DNA segments with total lengths of about 1900, 1000, 500, 200, 100 and about 50 base pairs in length are also contemplated to be useful.

A preferred embodiment of the present invention is a nucleic acid segment which comprises at least a 14-nucleotide long stretch which corresponds to, or is complementary to, the nucleic acid sequence of SEQ ID NO:3. In a more preferred embodiment the nucleic acid is further defined as comprising at least a 20 nucleotide long stretch, a 30 nucleotide long stretch, 50 nucleotide long stretch, 100 nucleotide long stretch, or at least an 2000 nucleotide long stretch which corresponds to, or is complementary to, the nucleic acid sequence of SEQ ID NO:3. The nucleic acid segment may be further defined as having the nucleic acid sequence of SEQ ID NO:3.

A related embodiment of the present invention is a nucleic acid segment which comprises at least a 14-nucleotide long stretch which corresponds to, or is complementary to, the nucleic acid sequence of SEQ ID NO:3, further defined as comprising a nucleic acid fragment of up to 10,000 basepairs in length. A more preferred embodiment if a nucleic acid fragment comprising from 14 nucleotides of SEQ ID NO:3 up to 5,000 basepairs in length, 3,000 basepairs in length, 2,000 basepairs in length, 1,000 basepairs in length, 500 basepairs in length, or 100 basepairs in length.

Naturally, it will also be understood that this invention is not limited to the particular nucleic acid and amino acid sequences of SEQ ID NO: 3. Recombinant vectors and isolated DNA segments may therefore variously include the OIP coding regions themselves, coding regions bearing selected alterations or modifications in the basic coding region, or they may encode larger polypeptides which nevertheless include OIP-coding regions or may encode biologically functional equivalent proteins or peptides which have variant amino acids sequences.

The DNA segments of the present invention encompass biologically functional equivalent OIP proteins and peptides. Such sequences may arise as a consequence of codon redundancy and functional equivalency which are known to occur naturally within nucleic acid sequences and the proteins thus encoded. Alternatively, functionally equivalent proteins or peptides may be created via the application of recombinant DNA technology, in which changes in the protein structure may be engineered, based on considerations of the properties of the amino acids being exchanged. Changes designed by man may be introduced through the application of site-directed mutagenesis techniques, e.g., to introduce improvements to the antigenicity of the OIP protein or to test OIP mutants in order to examine activity or determine the presence of OIP peptide in various cells and tissues at the molecular level.

A preferred embodiment of the present invention is a purified composition comprising a polypeptide having an amino acid sequence in accordance with SEQ ID NO:4. The term "purified" as used herein, is intended to refer to an OIP protein composition, wherein the OIP protein is purified to any degree relative to its naturally-obtainable state, i.e., in this case, relative to its purity within a eukaryotic cell extract. A preferred cell for the isolation of OIP protein is a pancreas or intestinal villi cell, however, OIP protein may also be isolated from patient specimens, recombinant cells, tissues, isolated subpopulations of tissues, and the like, as will be known to those of skill in the art, in light of the present disclosure. A purified OIP protein composition therefore also refers to a polypeptide having the amino acid sequence of SEQ ID NO:4, free from the environment in which it may naturally occur.

If desired, one may also prepare fusion proteins and peptides, e.g., where the OIP coding regions are aligned within the same expression unit with other proteins or peptides having desired functions, such as for purification or immunodetection purposes (e.g., proteins which may be purified by affinity chromatography and enzyme label coding regions, respectively).

Turning to the expression of the oip-2 gene whether from cDNA based or genomic DNA, one may proceed to prepare an expression system for the recombinant preparation of OIP proteins. The engineering of DNA segment(s) for expression in a prokaryotic or eukaryotic system may be performed by techniques generally known to those of skill in recombinant expression. For example, one may prepare a OIP-GST (glutathione-S-transferase) fusion protein that is a convenient means of bacterial expression. However, it is believed that virtually any expression system may be employed in the expression of OIP.

OIP may be successfully expressed in eukaryotic expression systems; however, the inventors contemplate that bacterial expression systems may be used for the preparation of OIP for all purposes. The cDNA containing oip-2 gene may be separately expressed in bacterial systems, with the encoded proteins being expressed as fusions with β-galactosidase, avidin, ubiquitin, Schistosoma japonicum glutathione S-transferase, multiple histidines, epitope-tags and the like. It is believed that bacterial expression will ultimately have advantages over eukaryotic expression in terms of ease of use and quantity of materials obtained thereby.

It is proposed that transformation of host cells with DNA segments encoding OIP will provide a convenient means for obtaining an OIP protein. It is also proposed that cDNA, genomic sequences, and combinations thereof, are suitable for eukaryotic expression, as the host cell will, of course, process the genomic transcripts to yield functional mRNA for translation into protein.

Another embodiment is a method of preparing a protein composition comprising growing recombinant host cell comprising a vector that encodes a protein which includes an amino acid sequence in accordance with SEQ ID NO:4, under conditions permitting nucleic acid expression and protein production followed by recovering the protein so produced. The host cell, conditions permitting nucleic acid expression, protein production and recovery, will be known to those of skill in the art, in light of the present disclosure of the oip-2 gene.

2.4 Gene Constructs and DNA Segments

As used herein, the terms "gene" and "DNA segment" are both used to refer to a DNA molecule that has been isolated free of total genomic DNA of a particular species. Therefore, a gene or DNA segment encoding an OIP polypeptide refers to a DNA segment that contains sequences encoding an OIP protein, but is isolated away from, or purified free from, total genomic DNA of the species from which the DNA is obtained. Included within the term "DNA segment", are DNA segments and smaller fragments of such segments, and also recombinant vectors, including, for example, plasmids, cosmids, phage, retroviruses, adenoviruses, and the like.

The term "gene" is used for simplicity to refer to a functional protein or peptide encoding unit. As will be understood by those in the art, this functional term includes both genomic sequences and cDNA sequences. "Isolated substantially away from other coding sequences" means that the gene of interest, in this case, an osteoclast-inhibiting factor gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions, such as sequences encoding leader peptides or targeting sequences, later added to the segment by the hand of man.

2.5 Recombinant Vectors Expressing OIP

A particular aspect of this invention provides novel ways in which to utilize OIP-encoding DNA segments and recombinant vectors comprising oip-2 DNA segments. As is well known to those of skill in the art, many such vectors are readily available, one particular detailed example of a suitable vector for expression in mammalian cells is that described in U.S. Pat. No. 5,168,050, incorporated herein by reference. However, there is no requirement that a highly purified vector be used, so long as the coding segment employed encodes a OIP protein and does not include any coding or regulatory sequences that would have an adverse effect on cells. Therefore, it will also be understood that useful nucleic acid sequences may include additional residues, such as additional non-coding sequences flanking either of the 5' or 3' portions of the coding including, for example, promoter regions or may include various internal sequences, ie., introns, which are known to occur within genes.

After identifying an appropriate OIP-encoding gene or DNA molecule, it may be inserted into any one of the many vectors currently known in the art, so that it will direct the expression and production of the OIP protein when incorporated into a host cell. In a recombinant expression vector, the coding portion of the DNA segment is positioned under the control of a promoter. The promoter may be in the form of the promoter which is naturally associated with a OIP-encoding gene, as may be obtained by isolating the 5' non-coding sequences located upstream of the coding segment or exon, for example, using recombinant cloning and/or PCR technology, in connection with the compositions disclosed herein.

In certain embodiments, it is contemplated that particular advantages will be gained by positioning the OIP-encoding DNA segment under the control of a recombinant, or heterologous, promoter. As used herein, a recombinant or heterologous promoter is intended to refer to a promoter that is not normally associated with an oip gene in its natural environment. Such promoters may include those normally associated with other osteoclast-inhibitory polypeptide genes, and/or promoters isolated from any other bacterial, viral, eukaryotic, or mammalian cell. Naturally, it will be important to employ a promoter that effectively directs the expression of the DNA segment in the particular cell containing the vector comprising the OIP gene.

The use of recombinant promoters to achieve protein expression is generally known to those of skill in the art of molecular biology, for example, see Sambrook et al., (1989). The promoters employed may be constitutive, or inducible, and can be used under the appropriate conditions to direct high level or regulated expression of the introduced DNA segment. The currently preferred promoters are those such as CMV, RSV LTR, the SV40 promoter alone, and the SV40 promoter in combination with the SV40 enhancer.

2.6 Methods of DNA Transfection

Technology for introduction of DNA into cells is well-known to those of skill in the art. Four general methods for delivering a gene into cells have been described: (1) chemical methods (Graham and VanDerEb, 1973); (2) physical methods such as microinjection (Capecchi, 1980), electroporation (Wong and Neumann, 1982; Fromm et al., 1985) and the gene gun (Yang et al., 1990); (3) viral vectors (Clapp, 1993; Danos and Heard, 1992; Eglitis and Anderson, 1988); and (4) receptor-mediated mechanisms (Wu et al., 1991; Curiel et al., 1991; Wagner et al., 1992).

2.7 Liposomes and Nanocapsules

The formation and use of liposomes is generally known to those of skill in the art (see for example, Couvreur et al., 1991 which describes the use of liposomes and nanocapsules in the targeted antibiotic therapy of intracellular bacterial infections and diseases). Recently, liposomes were developed with improved serum stability and circulation half-times (Gabizon and Papahadjopoulos, 1988; Allen and Choun, 1987). The following is a brief description of these DNA delivery modes.

Nanocapsules can generally entrap compounds in a stable and reproducible way (Henry-Michelland et al., 1987). To avoid side effects due to intracellular polymeric overloading, such ultrafine particles (sized around 0.1 mm) should be designed using polymers able to be degraded in vivo. Biodegradable polyalkyl-cyanoacrylate nanoparticles that meet these requirements are contemplated for use in the present invention, and such particles may be are easily made, as described (Couvreur et al., 1984; 1988).

Liposomes are formed from phospholipids that are dispersed in an aqueous medium and spontaneously form multilamellar concentric bilayer vesicles (also termed multilamellar vesicles (MLVs). MLVs generally have diameters ranging from 25 nm to 4 mm. Sonication of MLVs results in the formation of small unilamellar vesicles (SUVs) with diameters in the range of 200 to 500 Å, containing an aqueous solution in the core.

In addition to the teachings of Couvreur et al. (1991), the following information may be utilized in generating liposomal formulations. Phospholipids can form a variety of structures other than liposomes when dispersed in water, depending on the molar ratio of lipid to water. At low ratios the liposome is the preferred structure. The physical characteristics of liposomes depend on pH, ionic strength and the presence of divalent cations. Liposomes can show low permeability to ionic and polar substances, but at elevated temperatures undergo a phase transition which markedly alters their permeability. The phase transition involves a change from a closely packed, ordered structure, known as the gel state, to a loosely packed, less-ordered structure, known as the fluid state. This occurs at a characteristic phase-transition temperature and results in an increase in permeability to ions, sugars and drugs.

Liposomes interact with cells via four different mechanisms: Endocytosis by phagocytic cells of the reticuloendothelial system such as macrophages and neutrophils; adsorption to the cell surface, either by nonspecific weak hydrophobic or electrostatic forces, or by specific interactions with cell-surface components; fusion with the plasma cell membrane by insertion of the lipid bilayer of the liposome into the plasma membrane, with simultaneous release of liposomal contents into the cytoplasm; and by transfer of liposomal lipids to cellular or subcellular membranes, or vice versa, without any association of the liposome contents. It often is difficult to determine which mechanism is operative and more than one may operate at the same time.

2.8 Expression of OIP

For the expression of OIP, once a suitable (full-length if desired) clone or clones have been obtained, whether they be cDNA based or genomic, one may proceed to prepare an expression system for the recombinant preparation of OIP. The engineering of DNA segment(s) for expression in a prokaryotic or eukaryotic system may be performed by techniques generally known to those of skill in recombinant expression. It is believed that virtually any expression system may be employed in the expression of OIP.

OIP may be successfully expressed in eukaryotic expression systems, however, it is also envisioned that bacterial expression systems may be preferred for the preparation of OIP for all purposes. The cDNA for OIP may be separately expressed in bacterial systems, with the encoded proteins being expressed as fusions with b-galactosidase, ubiquitin, *Schistosoma japonicum* glutathione S-transferase, green fluorescent protein and the like. It is believed that bacterial expression will ultimately have advantages over eukaryotic expression in terms of ease of use and quantity of materials obtained thereby.

It is proposed that transformation of host cells with DNA segments encoding OIP will provide a convenient means for obtaining OIP peptide. Both cDNA and genomic sequences are suitable for eukaryotic expression, as the host cell will, of course, process the genomic transcripts to yield functional mRNA for translation into protein.

It is similarly believed that almost any eukaryotic expression system may be utilized for the expression of OIP, e.g., baculovirus-based, glutamine synthase-based or dihydrofolate reductase-based systems could be employed. However, in preferred embodiments, it is contemplated that plasmid vectors incorporating an origin of replication and an efficient eukaryotic promoter, as exemplified by the eukaryotic vectors of the pCMV series, such as pCMV5, will be of most use.

For expression in this manner, one would position the coding sequences adjacent to and under the control of the promoter. It is understood in the art that to bring a coding sequence under the control of such a promoter, one positions the 5' end of the transcription initiation site of the transcriptional reading frame of the protein between about 1 and about 50 nucleotides "downstream" of (i.e., 3' of) the chosen promoter.

Where eukaryotic expression is contemplated, one will also typically desire to incorporate into the transcriptional unit which includes OIP, an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

Translational enhancers may also be incorporated as part of the vector DNA. Thus the DNA constructs of the present invention should also preferable contain one or more 5' non-translated leader sequences which may serve to enhance expression of the gene products from the resulting mRNA transcripts. Such sequences may be derived from the promoter selected to express the gene or can be specifically modified to increase translation of the RNA. Such regions may also be obtained from viral RNAs, from suitable eukaryotic genes, or from a synthetic gene sequence (Griffiths, et al, 1993).

Such "enhancer" sequences may be desirable to increase or alter the translational efficiency of the resultant mRNA. The present invention is not limited to constructs where the enhancer is derived from the native 5'-nontranslated promoter sequence, but may also include non-translated leader sequences derived from other non-related promoters such as other enhancer transcriptional activators or genes.

It is contemplated that virtually any of the commonly employed host cells can be used in connection with the expression of OIPs in accordance herewith. Examples include cell lines typically employed for eukaryotic expression such as 293, AtT-20, HepG2, VERO, HeLa, CHO, WI 38, BHK, COS-7, RIN and MDCK cell lines.

It is contemplated that OIP may be "overexpressed", i.e., expressed in increased levels relative to its natural expression in human cells, or even relative to the expression of other proteins in a recombinant host cell containing OIP-encoding DNA segments. Such overexpression may be assessed by a variety of methods, including radio-labeling and/or protein purification. However, simple and direct methods are preferred, for example, those involving SDS/PAGE and protein staining or Western blotting, followed by quantitative analyses, such as densitometric scanning of the resultant gel or blot. A specific increase in the level of the recombinant protein or peptide in comparison to the level in natural OIP-producing animal cells is indicative of overexpression, as is a relative abundance of the specific protein in relation to the other proteins produced by the host cell and, e.g., visible on a gel.

As used herein, the term "engineered" or "recombinant" cell is intended to refer to a cell into which a recombinant gene, such as a gene encoding a OIP peptide has been introduced. Therefore, engineered cells are distinguishable from naturally occurring cells which do not contain a recombinantly introduced gene. Engineered cells are thus cells having a gene or genes introduced through the hand of man. Recombinantly introduced genes will either be in the form of a cDNA gene (ie., they will not contain introns), a copy of a genomic gene, or will include genes positioned adjacent to a promoter not naturally associated with the particular introduced gene.

It will be understood that recombinant OIPs may differ from naturally produced OIP in certain ways. In particular, the degree of post-translational modifications, such as, for example, glycosylation and phosphorylation may be different between the recombinant OIP and the OIP polypeptide purified from a natural source, such as osteoblasts.

Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventors do not exclude the possibility of employing a genomic version of a particular gene where desired.

After identifying an appropriate DNA molecule by any or a combination of means as described above, the DNA may then be inserted into any one of the many vectors currently known in the art and transferred to a prokaryotic or eukaryotic host cell where it will direct the expression and production of the so-called "recombinant" version of the protein. The recombinant host cell may be selected from a group consisting of S. mutans, E. coli, S. cerevisae. Bacillus sp., Lactococci sp., Enterococci sp., or Salmonella sp. In certain preferred embodiments, the recombinant host cell will have a recA phenotype.

Where the introduction of a recombinant version of one or more of the foregoing genes is required, it will be important to introduce the gene such that it is under the control of a promoter that effectively directs the expression of the gene in the cell type chosen for engineering. In general, one will desire to employ a promoter that allows constitutive (constant) expression of the gene of interest. Commonly used constitutive promoters are generally viral in origin, and include the cytomegalovirus (CMV) promoter, the Rous sarcoma long-terminal repeat (LTR) sequence, and the SV40 early gene promoter. The use of these constitutive promoters will ensure a high, constant level of expression of the introduced genes. The level of expression from the introduced genes of interest can vary in different clones, probably as a function of the site of insertion of the recombinant gene in the chromosomal DNA. Thus, the level of expression of a particular recombinant gene can be chosen by evaluating different clones derived from each transfection experiment; once that line is chosen, the constitutive promoter ensures that the desired level of expression is permanently maintained. It may also be possible to use promoters that are specific for cell type used for engineering, such as the insulin promoter in insulinoma cell lines, or the prolactin or growth hormone promoters in anterior pituitary cell lines.

2.9 Recombinant OIP Polypeptides

Recombinant versions of a protein or polypeptide are deemed as part of the present invention. Thus one may, using techniques familiar to those skilled in the art, express a recombinant version of the polypeptide in a recombinant cell to obtain the polypeptide from such cells. The techniques are based on cloning of a DNA molecule encoding the polypeptide from a DNA library, that is, on obtaining a specific DNA molecule distinct from other DNAs. One may, for example, clone a cDNA molecule, or clone genomic DNA. Techniques such as these would also be appropriate for the production of the osteoclast inhibitory polypeptides in accordance with the present invention.

2.10 Enhanced Production of OIP

Potential problems with OIP isolated from natural sources are low yields and extensive purification processes. An aspect of the present invention is the enhanced production of OIP by recombinant methodologies in a bacterial host, employing DNA constructs to transform Gram-positive or Gram-negative bacterial cells. For example, the use of Escherichia coli expression systems is well known to those of skill in the art, as is the use of other bacterial species such as Bacillus subtilis or Streptococcus sanguis.

Further aspects of the invention include high expression vectors incorporating DNA encoding the novel OIP and its variants. It is contemplated that vectors providing enhanced expression of OIP in other systems such as *S. mutans* will also be obtainable. Where it is desirable, modifications of the physical properties of OIP may be sought to increase its solubility or expression in liquid culture. The oip-2 locus may be placed under control of a high expression promoter or the components of the expression system altered to enhance expression.

In further embodiments, the DNA encoding the OIP of the present invention allows for the large scale production and isolation of OIP polypeptides. This can be accomplished by directing the expression of the OIP polypeptide by cloning the DNA encoding the OIP polypeptide into a suitable expression vector. Such an expression vector may then be transformed into a host cell that is able to produce the OIP protein. The OIP protein may then be purified, e.g., by means provided for in this disclosure and utilized in a biologically active form. Non-biologically active recombinant OIP may also have utility, e.g., as an immunogen to prepare anti-OIP antibodies.

2.11 Gene Therapy

Adenovirus is particularly suitable for use as a gene transfer vector because of its mid-sized DNA genome, ease of manipulation, high titer, wide target-cell range, and high infectivity. The roughly 36 kB viral genome is bounded by 100–200 base pair (bp) inverted terminal repeats (ITR), in which are contained cis-acting elements necessary for viral DNA replication and packaging. The early (E) and late (L) regions of the genome that contain different transcription units are divided by the onset of viral DNA replication.

The E1 region (E1A and E1B) encodes proteins responsible for the regulation of transcription of the viral genome and a few cellular genes. The expression of the E2 region (E2A and E2B) results in the synthesis of the proteins for viral DNA replication. These proteins are involved in DNA replication, late gene expression, and host cell shut off (Renan, 1990). The products of the late genes (L1, L2, L3, L4 and L5), including the majority of the viral capsid proteins, are expressed only after significant processing of a single primary transcript issued by the major late promoter (MLP). The MLP (located at 16.8 map units) is particularly efficient during the late phase of infection, and all the mRNAs issued from this promoter possess a 5' tripartite leader (TL) sequence which makes them preferred mRNAs for translation.

In order for adenovirus to be optimized for gene therapy, it is necessary to maximize the carrying capacity so that large segments of DNA can be included. It also is very desirable to reduce the toxicity and immunologic reaction associated with certain adenoviral products.

The large displacement of DNA is possible because the cis elements required for viral DNA replication all are localized in the inverted terminal repeats (ITR) (100–200 bp) at either end of the linear viral genome. Plasmids containing ITR's can replicate in the presence of a non-defective adenovirus (Hay et al., 1984). Therefore, inclusion of these elements in an adenoviral vector should permit replication.

In addition, the packaging signal for viral encapsidation is localized between 194–385 bp (0.5–1.1 map units) at the left end of the viral genome (Hearing et al., 1987). This signal mimics the protein recognition site in bacteriophage λ DNA where a specific sequence close to the left end, but outside the cohesive end sequence, mediates the binding to proteins that are required for insertion of the DNA into the head structure. E1 substitution vectors of Ad have demonstrated that a 450 bp (0–1.25 map units) fragment at the left end of the viral genome could direct packaging in 293 cells (Levrero et al., 1991).

It has been shown that certain regions of the adenoviral genome can be incorporated into the genome of mammalian cells and the genes encoded thereby expressed. These cell lines are capable of supporting the replication of an adenoviral vector that is deficient in the adenoviral function encoded by the cell line. There also have been reports of complementation of replication deficient adenoviral vectors by "helping" vectors, e.g., wild-type virus or conditionally defective mutants.

2.12 OIP Variants

OIP-1 and OIP-2 related proteins and functional variants are also considered part of the invention. Thus it is expected that truncated and mutated versions of OIP-1 (SEQ ID NO:2) will afford more convenient and effective forms of OIP for treatment regimens. Functional variants may include modifying the sequence of SEQ ID NO:2 by replacing cysteine at positions 3,6,15, 21, 28, 51, 55, 72, 73 and 78 with glycine or alanine. Other modifications include replacement of asparagine at position 79 of SEQ ID NO:2 with glutamine or replacing leucine at position number 1 of SEQ ID NO:2 with valine. Such modifications are expected to affect the tertiary structure of OIP and the GyPI anchor portion of OIP, thus identifying important structural components necessary for the inhibitory action of OIP.

In like manner, OIP-2 related proteins and functional variants are considered part of the invention. Thus, any functional version of SEQ ID NO:4, such as truncated species or homologs, and mutated versions of OIP-2 are considered as part of the invention.

Mutagenized recombinant OIPs are expected to have increased potency and prolonged in vivo half-life, thereby offering more effective long-term treatments. Novel OIPs thus may be obtained by modifications to the OIP gene, such as by site-specific mutagenesis.

2.13 Pharmaceutical Compositions

Pharmaceutical compositions prepared in accordance with the present invention find use in preventing or ameliorating abnormal bone resorption or bone turnover in a mammal suffering from such conditions as osteoporosis, Paget's disease of bone, lytic bone metastasis and myeloma bone disease. Such methods generally involve administering a pharmaceutical composition comprising an effective amount of an OIP protein, such as SEQ ID NO:4. Other exemplary compositions may include an effective amount of either an OIP variant or an OIP-encoding nucleic acid composition. Such compositions may also be used to generate an immune response in an animal in such cases where it may be desirable to block the effect of a naturally produced OIP protein.

Also included as part of the present invention therefore are novel compositions comprising nucleic acids which encode an OIP protein. It will, of course, be understood that one or more than one gene may be used in the methods and compositions of the invention. The nucleic acid delivery methods may thus entail the administration of one, two, three, or more, homologous OIP-encoding genes. The maximum number of genes that may be applied is limited only by practical considerations, such as the effort involved in simultaneously preparing a large number of gene constructs or even the possibility of eliciting an adverse cytotoxic effect.

The particular combination of genes may be two or more distinct genes; or it may be such that an OIP gene is combined with another gene and/or another protein such as a TSA1 or Sca2 protein, cofactor or other biomolecule; a cytokine gene may even be combined with a gene encoding a cell surface receptor capable of interacting with the polypeptide product of the first gene.

In using multiple genes, they may be combined on a single genetic construct under control of one or more promoters, or they may be prepared as separate constructs of the same or different types. Thus, an almost endless combination of different genes and genetic constructs may be employed. Certain gene combinations may be designed to, or their use may otherwise result in, achieving synergistic effects on OCL inhibition and/or stimulation of an immune response. Any and all such combinations are intended to fall within the scope of the present invention. Indeed, many synergistic effects have been described in the scientific literature, so that one of ordinary skill in the art would readily be able to identify likely synergistic gene combinations, or even gene-protein combinations.

It will also be understood that, if desired, the nucleic acid segment or gene encoding an OIP protein could be administered in combination with further agents, such as, e.g., proteins or polypeptides or various pharmaceutically active agents. So long as the composition comprises an OIP gene, there is virtually no limit to other components which may also be included, given that the additional agents do not cause a significant adverse effect upon contact with the target cells or host tissues. The nucleic acids may thus be delivered along with various other agents as required in the particular instance.

2.14 Kits

Therapeutic kits comprising OIP peptides or OIP-encoding nucleic acid segments comprise another aspect of the present invention. Such kits will generally contain, in suitable container means, a pharmaceutically acceptable formulation of an OIP peptide or a OIP-encoding nucleic acid composition. The kit may have a single container means that contains the OIP composition or it may have distinct container means for the OIP composition and other reagents which may be included within such kits.

The components of the kit may be provided as liquid solution(s), or as dried powder(s). When the components are provided in a liquid solution, the liquid solution is an aqueous solution, with a sterile aqueous solution being particularly preferred. When reagents or components are provided as a dry powder, the powder can be reconstituted by the addition of a suitable solvent. It is envisioned that the solvent may also be provided in another container means.

Kits may also comprise reagents for detecting OIP polypeptides, such as required for immunoassay. The immunodetection reagent will typically comprise a label associated with the antibody or antigen, or associated with a secondary binding ligand. Exemplary ligands might include a secondary antibody directed against the first antibody or antigen or a biotin or avidin (or streptavidin) ligand having an associated label. Of course, a number of exemplary labels are known in the art and all such labels may be employed in connection with the present invention. The kits may contain antibody-label conjugates either in fully conjugated form, in the form of intermediates, or as separate moieties to be conjugated by the user of the kit.

The container means will generally include at least one vial, test tube, flask, bottle, syringe or other container means, into which the antigen or antibody may be placed, and preferably suitably aliquoted. Where a second binding ligand is provided, the kit will also generally contain a second vial or other container into which this ligand or antibody may be placed. The kits of the present invention will also typically include a means for containing the antibody, antigen, and reagent containers in close confinement for commercial sale. Such containers may include injection or blow-molded plastic containers into which the desired vials are retained.

2.15 OIP Antibodies

In another aspect, the present invention contemplates an antibody that is immunoreactive with a polypeptide of the invention. An antibody can be a polyclonal or a monoclonal antibody. In a preferred embodiment, an antibody is a monoclonal antibody. Means for preparing and characterizing antibodies are well known in the art (See, e.g., Howell and Lane, 1988).

Briefly, a polyclonal antibody is prepared by immunizing an animal with an immunogen comprising a polypeptide of the present invention and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

Antibodies, both polyclonal and monoclonal, specific for OIP polypeptides and particularly those represented by SEQ ID NO:2 and SEQ ID NO:4, variants and epitopes thereof, may be prepared using conventional immunization techniques, as will be generally known to those of skill in the art. A composition containing antigenic epitopes of OIP can be used to immunize one or more experimental animals, such as a rabbit or mouse, which will then proceed to produce specific antibodies against OIP. Polyclonal antisera may be obtained, after allowing time for antibody generation, simply by bleeding the animal and preparing serum samples from the whole blood.

To obtain monoclonal antibodies, one would also initially immunize an experimental animal, often preferably a mouse, with an OIP composition. One would then, after a period of time sufficient to allow antibody generation, obtain a population of spleen or lymph cells from the animal. The spleen or lymph cells can then be fused with cell lines, such as human or mouse myeloma strains, to produce antibody-secreting hybridomas. These hybridomas may be isolated to obtain individual clones which can then be screened for production of antibody to the desired OIP peptide.

Following immunization, spleen cells are removed and fused, using a standard fusion protocol with plasmacytoma cells to produce hybridomas secreting monoclonal antibodies against OIP. Hybridomas which produce monoclonal antibodies to the selected antigens are identified using standard techniques, such as ELISA and Western blot methods. Hybridoma clones can then be cultured in liquid media and the culture supernatants purified to provide the OIP-specific monoclonal antibodies.

It is proposed that the monoclonal antibodies of the present invention will find useful application in standard immunochemical procedures, such as ELISA and Western blot methods, as well as other procedures which may utilize antibody specific to OIP epitopes.

Additionally, it is proposed that monoclonal antibodies specific to the particular chemokine may be utilized in other useful applications. For example, their use in immunoabsorbent protocols may be useful in purifying native or recombinant OP species or variants thereof.

In general, both poly- and monoclonal antibodies against OIP may be used in a variety of embodiments. For example, they may be employed in antibody cloning protocols to obtain cDNAs or genes encoding OIP or related proteins. They may also be used in inhibition studies to analyze the effects of OIP in cells or animals. Anti-OIP antibodies will also be useful in immunolocalization studies to analyze the distribution of OIP peptides during various cellular events, for example, to determine the cellular or tissue-specific distribution of the OIP peptide under different physiological conditions. A particularly useful application of such antibodies is in purifying native or recombinant OiP, for example, using an antibody affinity column. The operation of all such immunological techniques will be known to those of skill in the art in light of the present disclosure.

3.0 BRIEF DESCRIPTION OF THE DRAWINGS

The following drawings form part of the present specification and are included to further demonstrate certain aspects of the present invention. The invention may be better-understood by reference to one or more of these drawings in combination with the detailed description of specific embodiments presented herein.

FIG. 1. Correlation of 23c6+ MNC formation and TRAP activity in human marrow cultures.

Figure 2:
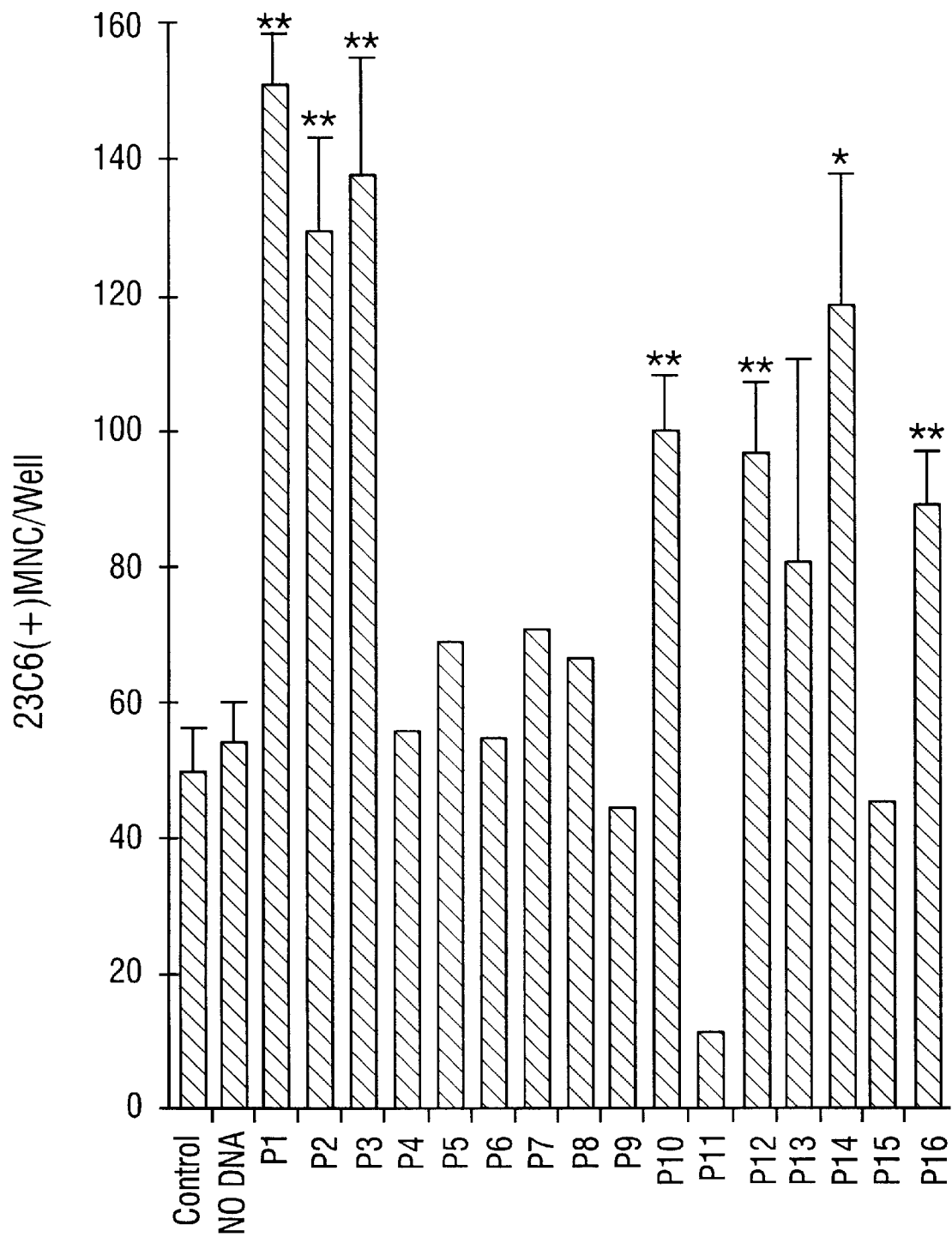

FIG. 2. MNC formation induced/inhibited by expression pools from a cDNA library derived from 23c6+ MNC.

Figure 3:
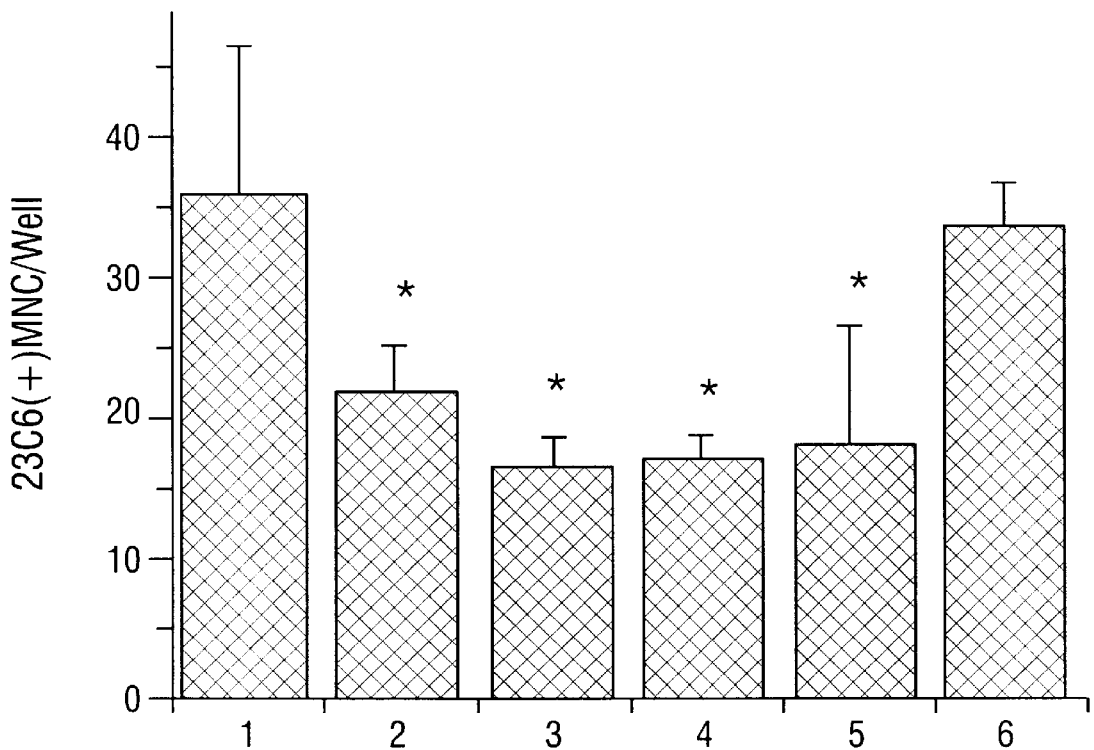

FIG. 3. The effects of conditioned media from osteoclast inhibitory peptide (OIP-1) cDNA on human bone marrow osteoclast-like multinucleated cell (MNC) formation. Various concentrations of conditioned media from 293 cells transfected with the OIP-1 cDNA were added to normal human bone marrow long-term cultures stimulated with $10^{-9}$ M $1,25\text{-}(OH)_2D_3$. After 3 weeks, the cultures were fixed and stained with the 23c6 monoclonal antibody that identified osteoclast-like multinucleated cells. Results represent the mean of four determinations for a typical study. 1: Control media; 2: Treated with 1% (v/v) conditioned media from cells transfected with the OIP-1 cDNA; 3: 5% (v/v) OIP-1 conditioned media; 4: 10% (v/v) OIP-1 conditioned media; 5: 20% (v/v) OIP-1 conditioned media; 6: 10% (v/v) conditioned media from cells transfected with the PCDNA1 vector. *$p<0.05$ compared to the control value.

Figure 4:
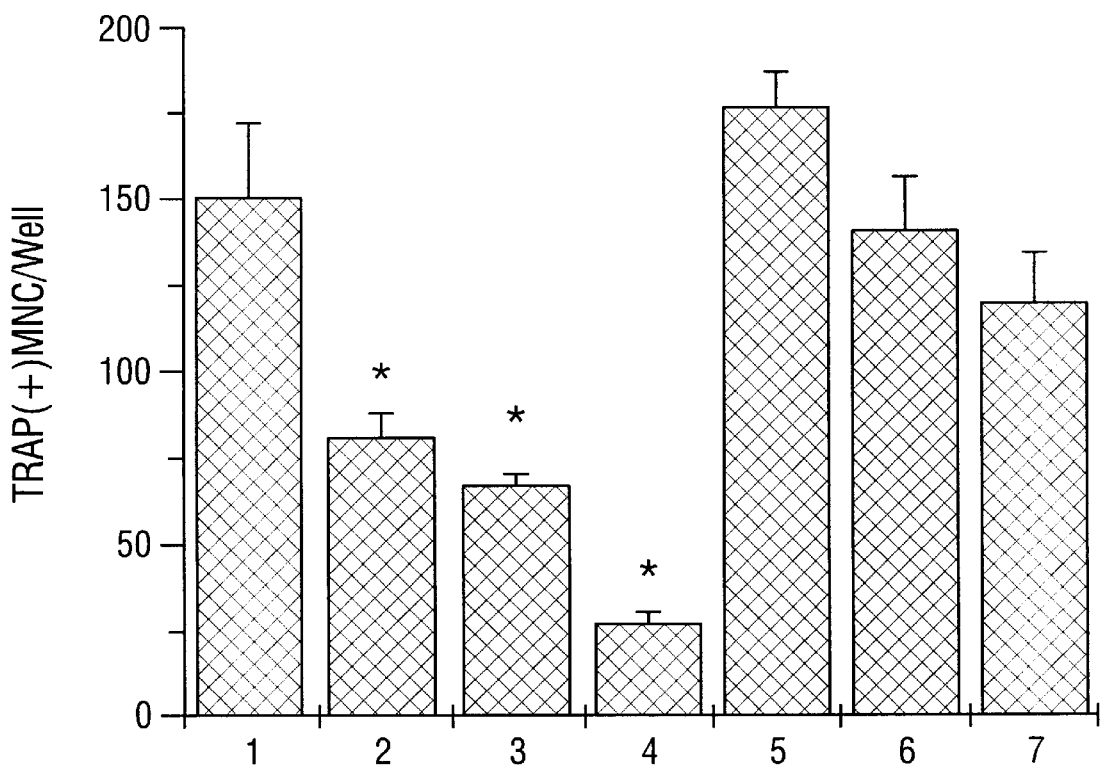

FIG. 4. The effects of conditioned media from cells transfected with the osteoclast inhibitory peptide (OIP)-1 cDNA on mouse bone marrow osteoclast-like multinucleated cell formation. Various concentrations of conditioned media from 293 cells transfected with the OIP-1 cDNA were added to normal mouse bone marrow cultures stimulated with $10^{-9}$ M $1,25\text{-}(OH)_2D_3$. After 6 days, the cultures were fixed and stained for tartrate-resistant acid phosphatase (TRAP) activity. Results represent the mean of five determinations for a typical study. 1: Control media; 2: Treated with 1% (v/v) OIP-1 containing conditioned media; 3: 5% (v/v) OIP-1 containing conditioned media; 4: 10% (v/v) OIP-1 containing conditioned media; 5: 5% (v/v) conditioned media from cells transfected with the OIP-1 cDNA in the reverse orientation; 6: 5% (v/v) conditioned media from cells transfected with the pCDNA1 vector; 7: 10% (v/v) conditioned media from cells transfected with the pCDNA1 vector *$p<0.05$ compared to the control value.

Figure 5:
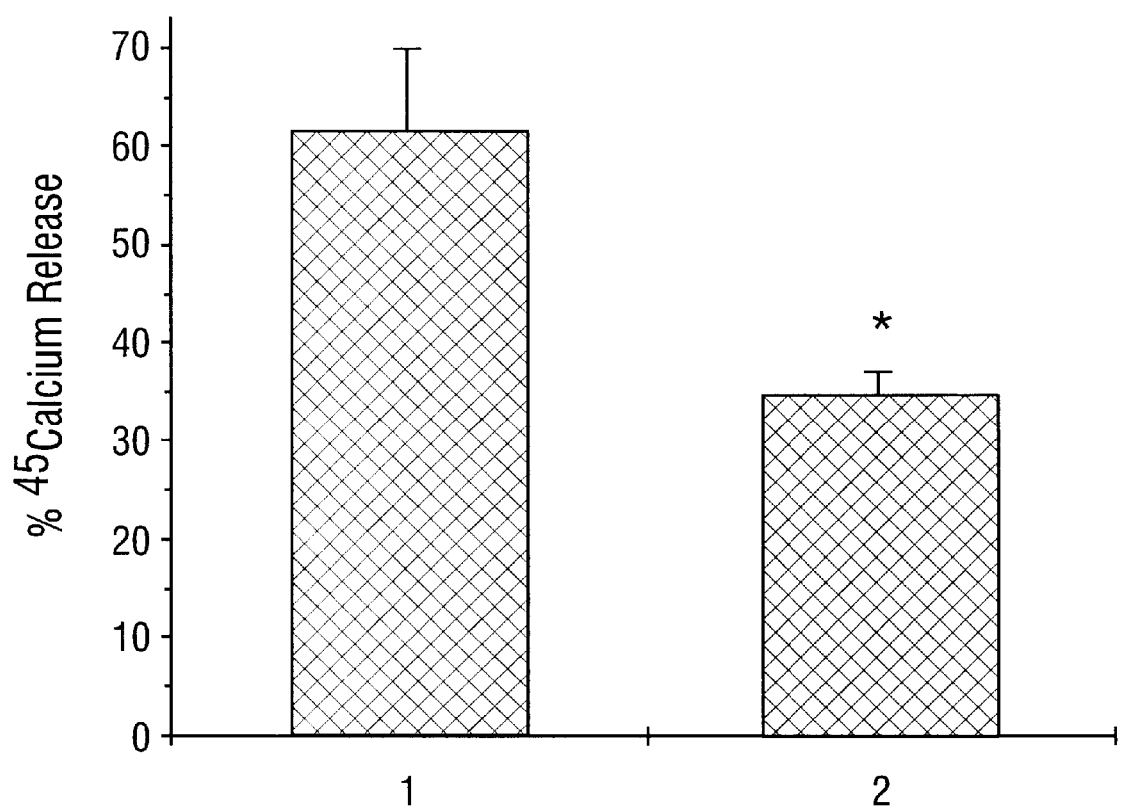

FIG. 5. The effects of conditioned media from cells transfected with osteoclast inhibitory peptide (OIP)-1 cDNA on bone resorption in the fetal rat long bone assay. Fetal rat long bones stimulated with $10^{-9}$ M $1,25\text{-}(OH)_2D_3$ were treated with conditioned media from 293 cells transfected with the OIP-1 cDNA. results represent the mean of four determinations for the typical study. 1: Treated with 32% (v/v) conditioned media from cells transfected with the pCDNA1 vector; 2: Treated with 16% (v/v) conditioned media from cells transfected with the pCDNA1 vector *$p<0.05$ compared to the control value.

FIG. 6A and FIG. 6B. DNA sequence and deduced amino acid sequence for OIP-1. The OIP-1 gene has 1095 nucleotides and 131 deduced amino acids. N-terminal 20 amino acids encode a cleavable N-terminal signal peptide and the C-terminus encodes the cytoplasmic tail.

Figure 7:
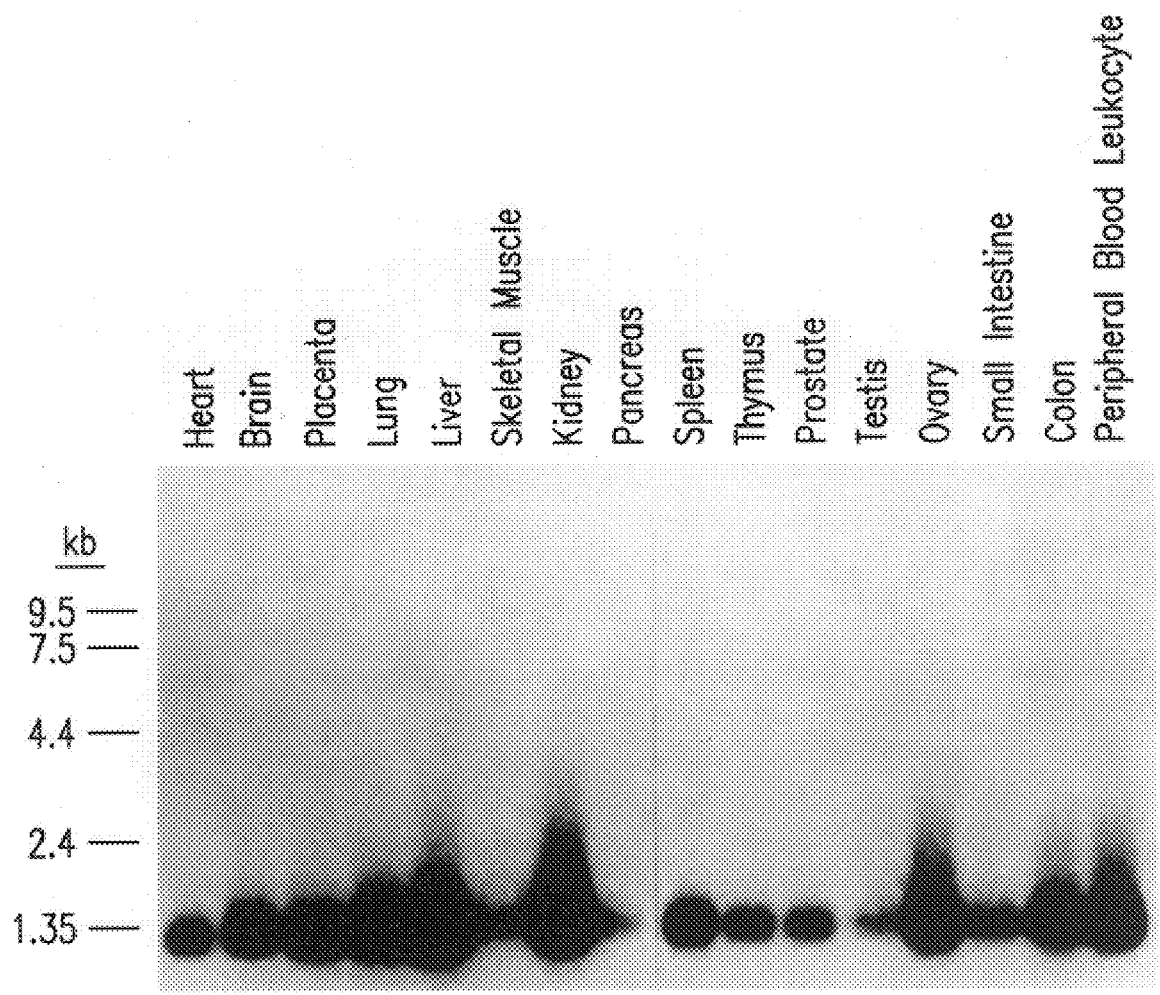

FIG. 7. Northern blot analysis of OIP-1 expression in human tissues.

Figure 8:
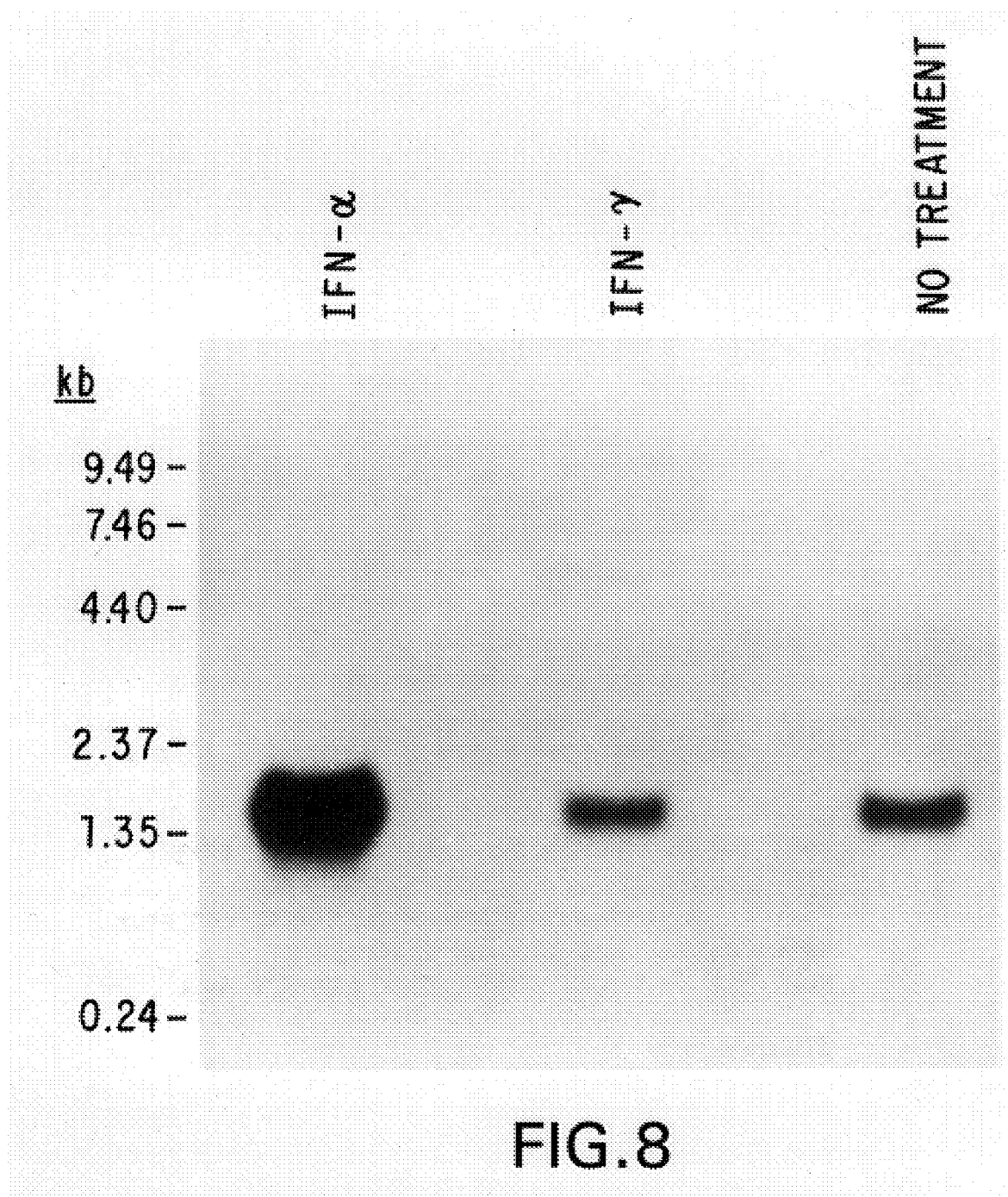

FIG. 8. Induction of OIP-1 by IFN-α.

Figure 9:
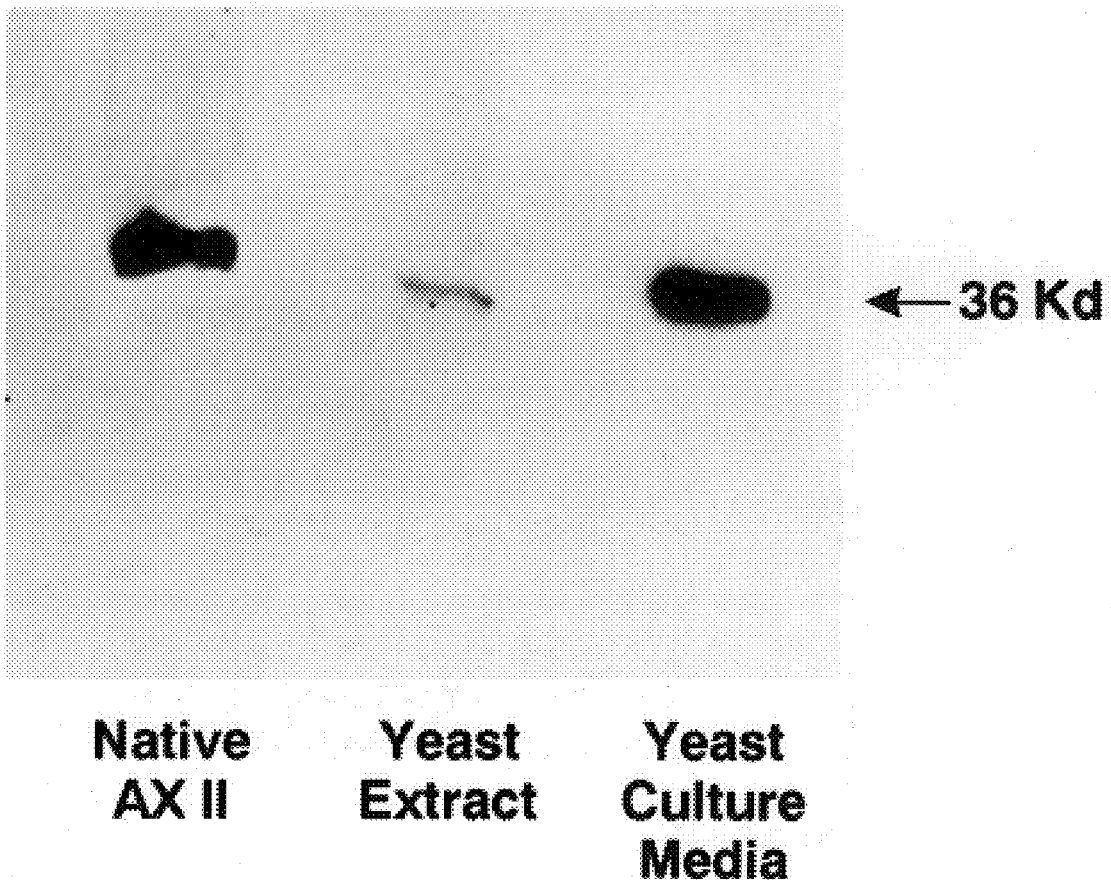

FIG. 9. Expression of recombinant AXII in yeast.

Figure 10:
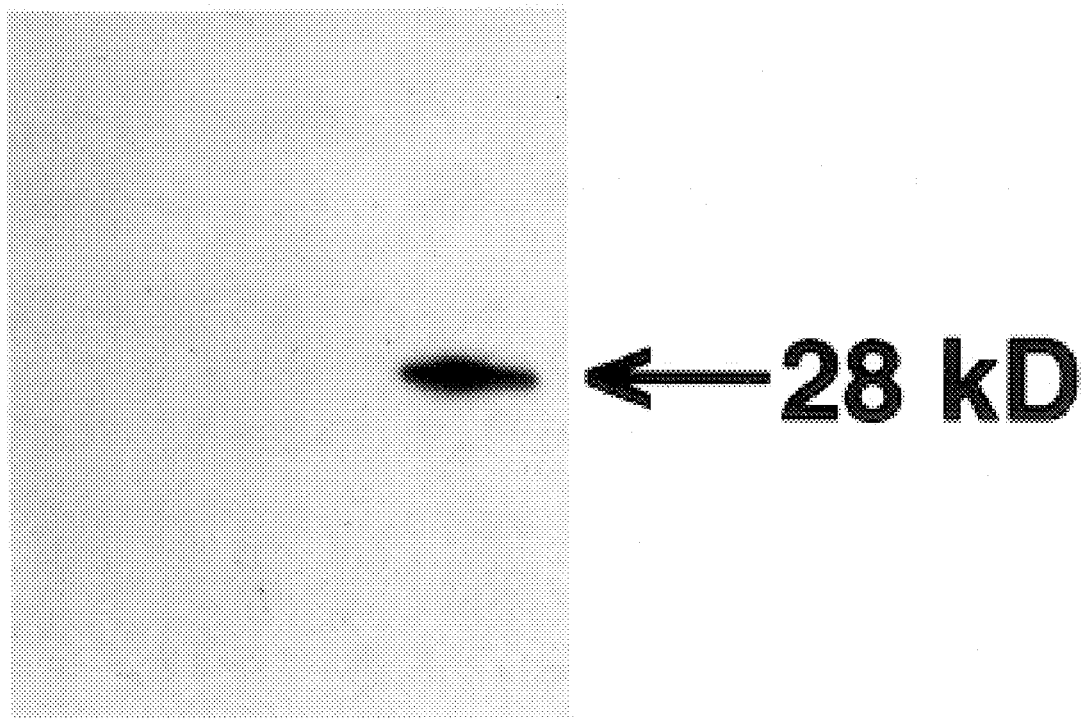

FIG. 10. Immunoblot analysis of OSF using polyclonal antisera.

Figure 11:
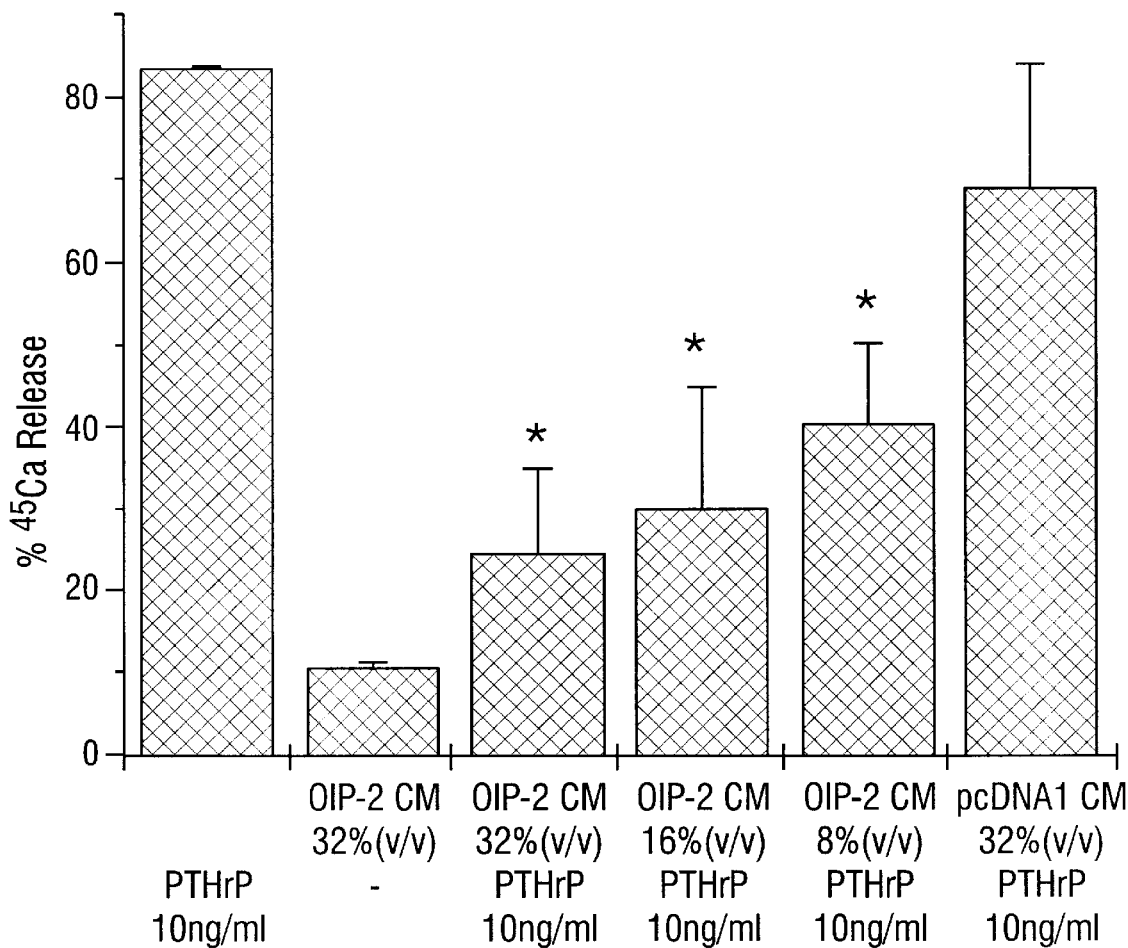

FIG. 11. Inhibitory effect of OIP-2 conditioned media on PTHrp or $1,25\ (OH)_2$ vitamin $D_3$ stimulated Bone Resorption in Fetal Rat Bone Assay.

Figure 12:
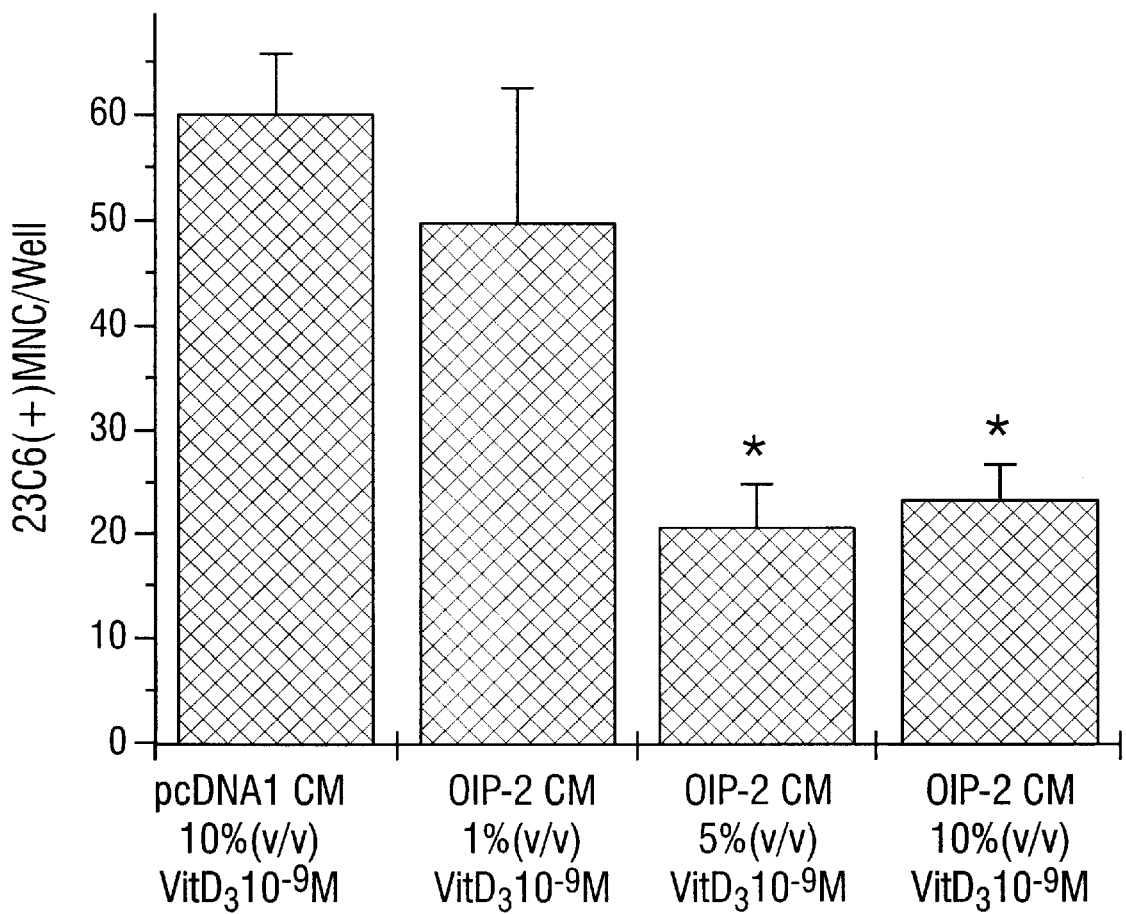

FIG. 12. Inhibition of Human Osteoclast Formation in Marrow Culture by Conditioned Media from 293 cells transfected with OIP-2 cDNA.

Figure 13:
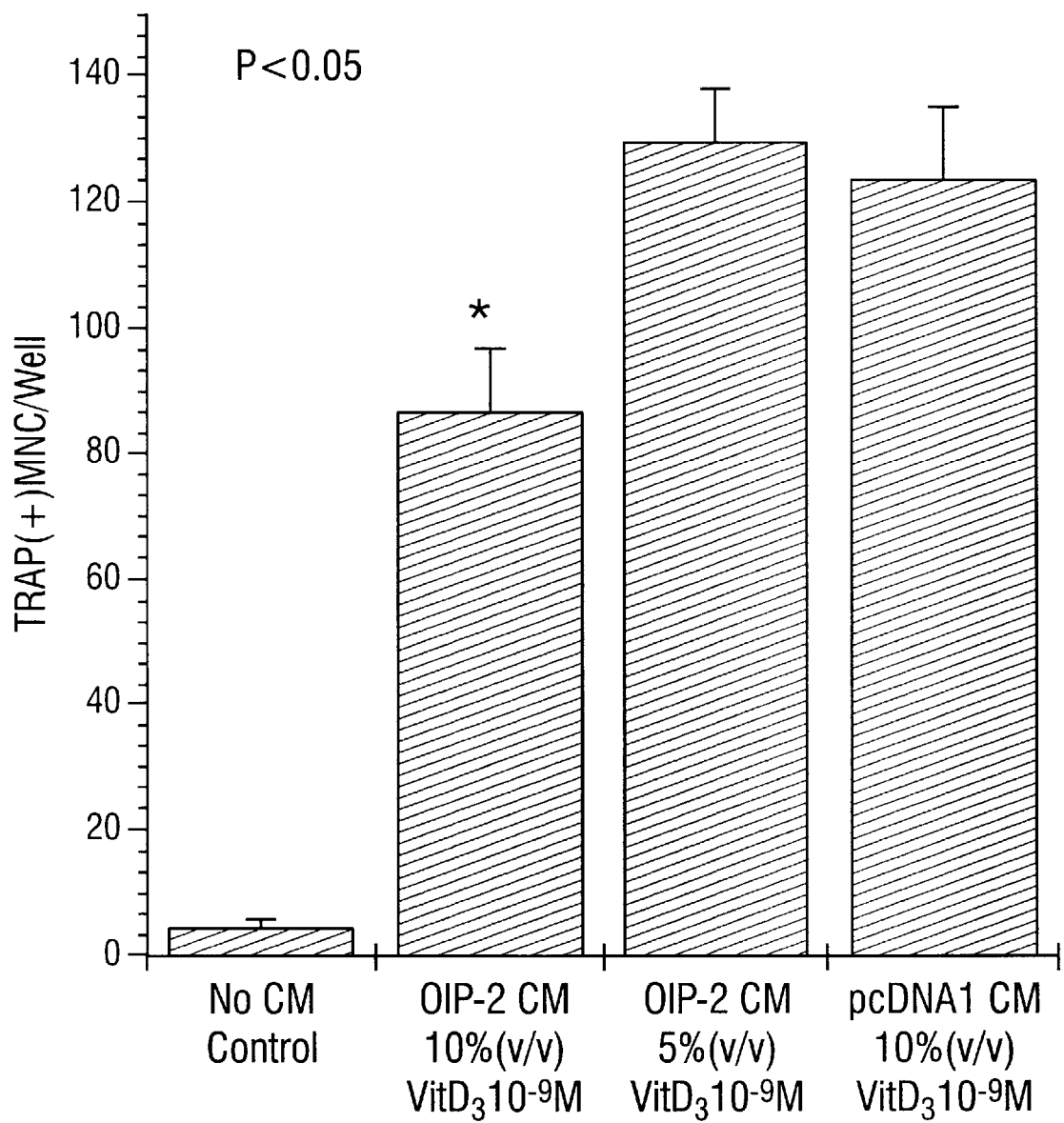

FIG. 13. Inhibition of Murine Osteoclast Formation in Marrow Culture by Conditioned Media from 293 cells transfected with OIP-2 cDNA.

Figure 14:
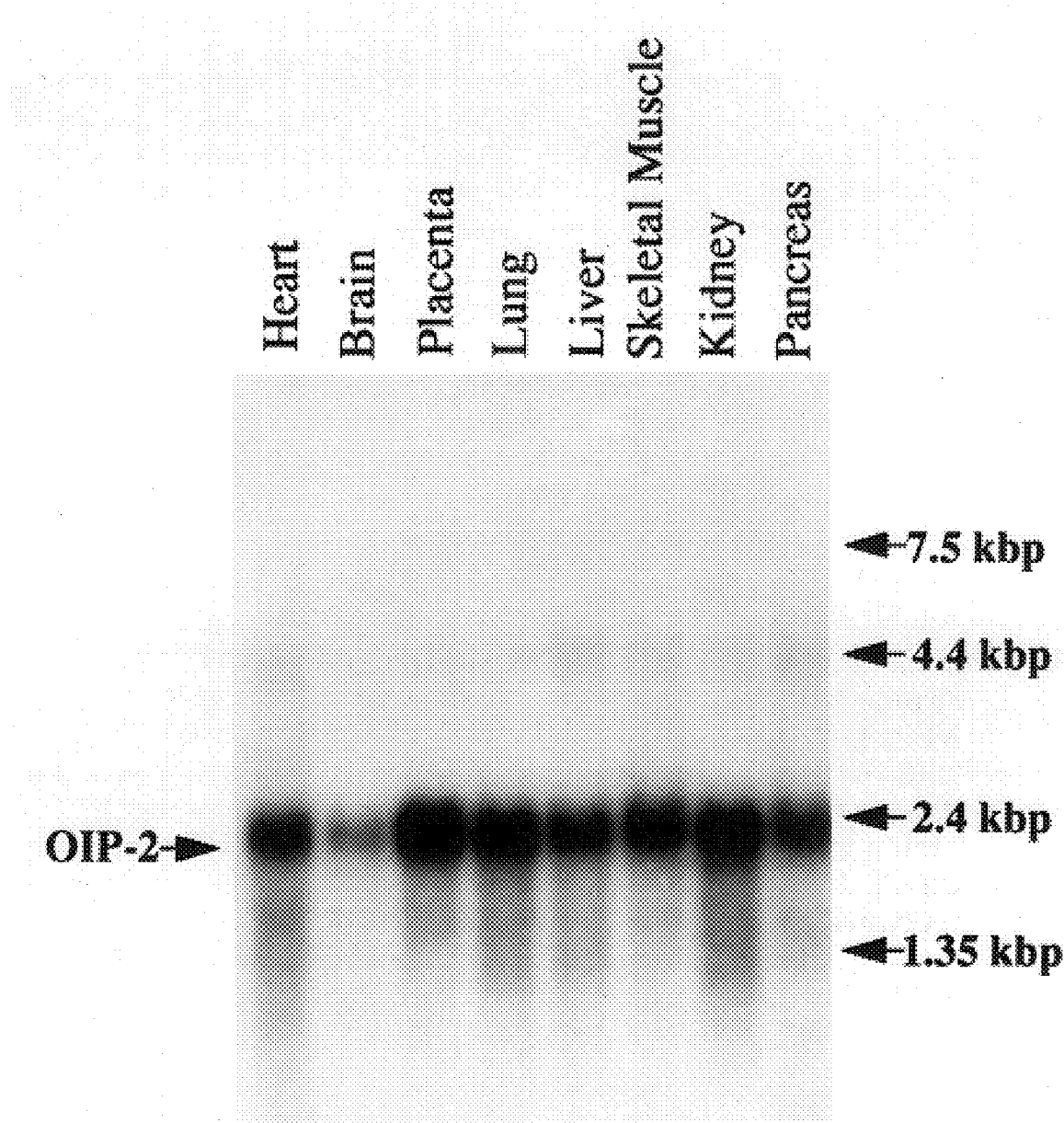

FIG. 14. Tissue distribution of OIP-2 by Northern blot analysis.

FIG. 15A, FIG. 15B and FIG. 15C. DNA sequence and deduced amino acid sequence for OIP-2. The OIP-2 gene has 1951 nucleotides and 478 deduced amino acids. The N-terminal 17 amino acids encode a cleavable N-terminal signal peptide. Localization of OIP-2 protein is outside of the cell.

4.0 DESCRIPTION OF ILLUSTRATIVE EMBODIMENTS

4.1 Advantages of the Invention

Osteoclasts function not only as bone-resorbing cells, but also as secretory cells. They express prodigious amounts of interleukin-6, in addition to lesser amounts of interleukin-1, TNF-α and transformation growth factor-β. They also appear to express other stimulators and inhibitors of bone cell function which have not yet been identified and characterized. Since these factors act locally in the bone marrow microenvironment, this suggests that autocrine/paracrine production of local estotropic factors by osteoclasts may be important in both physiological and pathological bone remodeling.

Using an expression cloning approach, the inventors have found that OCLs produce IL-6, IL-1, TGFβ and several other biologically active osteotropic molecules such as Annexin and OSF. In further studies, the inventors have identified and cloned novel inhibitory factors produced by OCL that block both OCL formation and bone resorption. One factor is the human homologue of Sca2, a member of the Ly6 family of proteins that is expressed by osteoclasts and osteoblasts, but heretofore had no known activity. Both factors represents a novel class of cell membrane-bound factors that inhibit OCL activity. The proteins have been designated osteoclast inhibitory peptide (OIP-1 and OIP-2). They have been identified by expression cloning techniques, and determination made of its production and regulation of action by other osteotropic cytokines.

Recombinant OIP-1 and OIP-2 have been prepared and its dose-response effects on OCL activity determined. Polyclonal antibodies are now available by methods well known to those skilled in the art and as described herein. Identification of important epitopic regions is now also possible and will allow the development of monoclonal antibodies.

Enhanced osteoclast (OCL) activity plays a major role in the pathogenesis of postmenopausal osteoporosis, Paget's disease of bone and hypercalcemia of malignancy. These important clinical problems are associated with significant morbidity or mortality and affect more than 10 million patients in the United States. However, only a limited number of agents that inhibit OCL formation or bone resorption are available and, for most, their mechanisms of action are unknown. Furthermore, many of these agents have significant side effects that limit their utility. Thus, the identification and characterization of novel inhibitors of osteoclast formation and bone resorption, such as OIP-1 and OIP-2, is expanded to provide major therapeutic benefits for these patients and to provide important insights into the mechanisms responsible for controlling normal osteoclast activity.

As discussed, the Ly6 gene family members are GPI-anchored proteins. GPIs serve as membrane anchors for numerous cell surface proteins, including alkaline phosphatase, decay accelerating factor, and murine MHC molecules. Importantly, GPI-anchored proteins can be cleaved from the cell surface by certain phospholipases such as phospholipase C and released as hydrophilic derivatives. These data suggest that the Ly6 gene family members may act as both soluble and membrane-bound factors.

The determination of the mechanism of action of OIP-1 and OIP-2 have provided important insights into the normal bone remodeling process. The work reported focuses on osteoclast inhibitory factors that demonstrate the therapeutic potential for patients with disordered osteoclast activity.

4.2 Regulation of OCL Formation and Activity

Antisense constructs are readily taken up by OCL and block cytokine production by OCL. Such antisense constructs are useful for dissecting the role of other OCL-derived factors in the bone resorption process.

Studies using long-term marrow cultures from patients with Paget's disease demonstrated that IL-6 was released into conditioned media from these cultures and stimulated OCL-like MNC formation in normal marrow cultures (Roodman et al., 1992). Consistent with these observations are those of Sharpe et al., (1996) who showed by in situ hybridization of bone biopsies that pagetic OCL express IL-6 and IL-6 receptor mRNA. These data suggested to the inventors that overexpression of autocrine factors produced by OCL may play an important role in some pathologic conditions associated with increased bone turnover.

The discovery that IL-6 is an autocrine factor that enhances OCL formation and activity further suggested that characterization of secretory products produced by OCLs would yield important new information on the regulation of OCL formation and activity. With this in mind, the inventors prepared cDNA libraries from highly purified human OCL-like cells to identify potentially novel factors produced by OCL and genes expressed at different stages of OCL development. These cDNA libraries were then converted to expression libraries and used to identify several novel factors produced by OCL that enhance their formation and bone-resorbing activity. Annexin II was the first factor identified. Annexin II previously was thought to be an intracellular protein that was neither secreted by cells nor stimulated OCL formation. Five other expression pools that contain clones that enhance MNC formation were also identified.

Identification of OIP-1 via expression cloning techniques revealed members of a family of physiologic regulators of osteoclast activity. The new proteins were found to be related to the Ly6 family of proteins.

4.3 Definitions

The following words and phrases have the meanings set forth below.

Expression: The combination of intracellular processes, including transcription and translation undergone by a coding DNA molecule such as a structural gene to produce a polypeptide.

Promoter: A recognition site on a DNA sequence or group of DNA sequences that provide an expression control element for a structural gene and to which RNA polymerase specifically binds and initiates RNA synthesis (transcription) of that gene.

Structural gene: A gene that is expressed to produce a polypeptide.

Transformation: A process of introducing an exogenous DNA sequence (e.g., a vector, a recombinant DNA molecule) into a cell in which that exogeneous DNA is incorporated into a chromosome or is capable of autonomous replication.

Transformed cell: A cell whose DNA has been altered by the introduction of an exogenous DNA molecule into that cell.

Vector: A DNA molecule capable of replication in a host cell and/or to which another DNA segment can be operatively linked so as to bring about replication of the attached segment. A plasmid is an exemplary vector.

Osteoclast Inhibitory Protein: A polypeptide produced by osteoclasts that inhibits the formation of osteoclasts and bone resorption. Such polypeptides may be truncated or synthetic versions of the naturally produced polypeptides.

Polypeptide: As used herein, polypeptide is used interchangeably with peptide or protein and refers to sequences of at least five amino acids.

Osteoclast: the primary bone resorbing cell.

Osteoblast: Cells that regulate osteoclastic bone resorption and secrete various cytokines that control bone remodeling. They play a key role in new bone formation.

4.4 Epitopic Core Sequences

The present invention is also directed to protein or peptide compositions, free from total cells and other peptides, which comprise a purified protein or peptide which incorporates an epitope that is immunologically cross-reactive with one or more anti-OIP protein antibodies. In particular, the invention concerns epitopic core sequences derived from OIP proteins or peptides.

As used herein, the term "incorporating an epitope(s) that is immunologically cross-reactive with one or more anti-OIP protein antibodies" is intended to refer to a peptide or protein antigen which includes a primary, secondary or tertiary structure similar to an epitope located within a OIP protein or polypeptide. The level of similarity will generally be to such a degree that monoclonal or polyclonal antibodies directed against the OIP protein or polypeptide will also bind to, react with, or otherwise recognize, the cross-reactive peptide or protein antigen. Various immunoassay methods may be employed in conjunction with such antibodies, such as, for example, Western blotting, ELISA, RIA, and the like, all of which are known to those of skill in the art.

The identification of OIP immunodominant epitopes, and/or their functional equivalents, suitable for use in vaccines is a relatively straightforward matter. For example, one may employ the methods of Hopp, as taught in U.S. Pat. No. 4,554,101, incorporated herein by reference, which teaches the identification and preparation of epitopes from amino acid sequences on the basis of hydrophilicity. The methods described in several other papers, and software programs based thereon, can also be used to identify epitopic core sequences (see, for example, Jameson and Wolf, 1988; Wolf et al., 1988; U. S. Pat. No. 4,554,101). The amino acid sequence of these "epitopic core sequences" may then be readily incorporated into peptides, either through the application of peptide synthesis or recombinant technology.

Preferred peptides for use in accordance with the present invention will generally be on the order of about 8 to about 20 amino acids in length, and more preferably about 8 to about 15 amino acids in length. It is proposed that shorter antigenic OIP protein-derived peptides will provide advantages in certain circumstances, for example, in the preparation of immunologic detection assays. Exemplary advantages include the ease of preparation and purification, the relatively low cost and improved reproducibility of production, and advantageous biodistribution.

It is proposed that particular advantages of the present invention may be realized through the preparation of synthetic peptides which include modified and/or extended epitopic/immunogenic core sequences which result in a "universal" epitopic peptide directed to OIP proteins, and in particular OIP and OIP-related sequences. These epitopic core sequences are identified herein in particular aspects as hydrophilic regions of the particular polypeptide antigen. It is proposed that these regions represent those which are most likely to promote T-cell or B-cell stimulation, and, hence, elicit specific antibody production.

An epitopic core sequence, as used herein, is a relatively short stretch of amino acids that is "complementary" to, and therefore will bind, antigen binding sites on the OIP protein-directed antibodies disclosed herein. Additionally or alternatively, an epitopic core sequence is one that will elicit antibodies that are cross-reactive with antibodies directed against the peptide compositions of the present invention. It will be understood that in the context of the present disclosure, the term "complementary" refers to amino acids or peptides that exhibit an attractive force towards each other. Thus, certain epitope core sequences of the present invention may be operationally defined in terms of their ability to compete with or perhaps displace the binding of the desired protein antigen with the corresponding protein-directed antisera.

In general, the size of the polypeptide antigen is not believed to be particularly crucial, so long as it is at least large enough to carry the identified core sequence or sequences. The smallest useful core sequence anticipated by the present disclosure would generally be on the order of about 8 amino acids in length, with sequences on the order of 10 to 20 being more preferred. Thus, this size will generally correspond to the smallest peptide antigens prepared in accordance with the invention. However, the size of the antigen may be larger where desired, so long as it contains a basic epitopic core sequence.

The identification of epitopic core sequences is known to those of skill in the art, for example, as described in U.S. Pat. No. 4,554,101, incorporated herein by reference, which teaches the identification and preparation of epitopes from amino acid sequences on the basis of hydrophilicity. Moreover, numerous computer programs are available for use in predicting antigenic portions of proteins (see e.g., Jameson and Wolf, 1988; Wolf et al., 1988). Computerized peptide sequence analysis programs (e.g., DNAStar® software, DNAStar, Inc., Madison, Wis.) may also be useful in designing synthetic peptides in accordance with the present disclosure.

Syntheses of epitopic sequences, or peptides which include an antigenic epitope within their sequence, are readily achieved using conventional synthetic techniques such as the solid phase method (e.g., through the use of commercially available peptide synthesizer such as an Applied Biosystems Model 430A Peptide Synthesizer). Peptide antigens synthesized in this manner may then be aliquoted in predetermined amounts and stored in conventional manners, such as in aqueous solutions or, even more preferably, in a powder or lyophilized state pending use.

In general, due to the relative stability of peptides, they may be readily stored in aqueous solutions for fairly long periods of time if desired, e.g., up to six months or more, in virtually any aqueous solution without appreciable degradation or loss of antigenic activity. However, where extended aqueous storage is contemplated it will generally be desirable to include agents including buffers such as Tris or phosphate buffers to maintain a pH of about 7.0 to about 7.5. Moreover, it may be desirable to include agents which will inhibit microbial growth, such as sodium azide or Merthiolate. For extended storage in an aqueous state it will be desirable to store the solutions at about 4° C., or more preferably, frozen. Of course, where the peptides are stored in a lyophilized or powdered state, they may be stored virtually indefinitely, e.g., in metered aliquots that may be rehydrated with a predetermined amount of water (preferably distilled) or buffer prior to use.

4.5 Biological Functional Equivalents

Modification and changes may be made in the structure of the peptides of the present invention and DNA segments which encode them and still obtain a functional molecule that encodes a protein or peptide with desirable characteristics. The following is a discussion based upon changing the amino acids of a protein to create an equivalent, or even an improved, second-generation molecule. In particular embodiments of the invention, mutated OIP proteins are contemplated to be useful for increasing the activity of the protein, and consequently increasing the OCL inhibiting activity and/or expression of the recombinant transgene in a mammalian cell. The amino acid changes may be achieved by changing the codons of the DNA sequence, according to the codons given in Table 3.

TABLE 3

| Amino Acids | | | Codons | | | |
|---|---|---|---|---|---|---|
| Alanine | Ala | A | GCA | GCC | GCG | GCU |
| Cysteine | Cys | C | UGC | UGU | | |
| Aspartic acid | Asp | D | GAC | GAU | | |
| Glutamic acid | Glu | E | GAA | GAG | | |
| Phenylalanine | Phe | F | UUC | UUU | | |
| Glycine | Gly | G | GGA | GGC | GGG | GGU |
| Histidine | His | H | CAC | CAU | | |
| Isoleucine | Ile | I | AUA | AUC | AUU | |
| Lysine | Lys | K | AAA | AAG | | |

TABLE 3-continued

| Amino Acids | | | Codons | | | | | |
|---|---|---|---|---|---|---|---|---|
| Leucine | Leu | L | UUA | UUG | CUA | CUC | CUG | CUU |
| Methionine | Met | M | AUG | | | | | |
| Asparagine | Asn | N | AAC | AAU | | | | |
| Proline | Pro | P | CCA | CCC | CCG | CCU | | |
| Glutamine | Gln | Q | CAA | CAG | | | | |
| Arginine | Arg | R | AGA | AGG | CGA | CGC | CGG | CGU |
| Serine | Ser | S | AGC | AGU | UCA | UCC | UCG | UCU |
| Threonine | Thr | T | ACA | ACC | ACG | ACU | | |
| Valine | Val | V | GUA | GUC | GUG | GUU | | |
| Tryptophan | Trp | W | UGG | | | | | |
| Tyrosine | Tyr | Y | UAC | UAU | | | | |

For example, certain amino acids may be substituted for other amino acids in a protein structure without appreciable loss of interactive binding capacity with structures such as, for example, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the peptide sequences of the disclosed compositions, or corresponding DNA sequences which encode said peptides without appreciable loss of their biological utility or activity.

In making such changes, the hydropathic index of amino acids may be considered. The importance of the hydropathic amino acid index in conferring interactive biologic function on a protein is generally understood in the art (Kyte and Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte and Doolittle, 1982), these are: isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outlined above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine.

4.6 Site Specific Mutagenesis

Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

In general, the technique of site-specific mutagenesis is well known in the art, as exemplified by various publications. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart of two strands of a double stranded vector which includes within its sequence a DNA sequence which encodes the desired peptide. An oligonucleotide primer bearing the desired mutated sequence is prepared, generally synthetically. This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement.

The preparation of sequence variants of the selected peptide-encoding DNA segments using site-directed mutagenesis is provided as a means of producing potentially useful species and is not meant to be limiting as there are other ways in which sequence variants of peptides and the DNA sequences encoding them may be obtained. For example, recombinant vectors encoding the desired peptide sequence may be treated with mutagenic agents, such as hydroxylamine, to obtain sequence variants.

4.7 Monoclonal Antibodies

Means for preparing and characterizing antibodies are well known in the art (See, e.g., Harlow and Lane, 1988; incorporated herein by reference).

The methods for generating monoclonal antibodies (mAbs) generally begin along the same lines as those for preparing polyclonal antibodies. Briefly, a polyclonal antibody is prepared by immunizing an animal with an immunogenic composition in accordance with the present invention and collecting antisera from that immunized animal. A wide range of animal species can be used for the production of antisera. Typically the animal used for production of anti-antisera is a rabbit, a mouse, a rat, a hamster, a guinea pig or a goat. Because of the relatively large blood volume of rabbits, a rabbit is a preferred choice for production of polyclonal antibodies.

As is well known in the art, a given composition may vary in its immunogenicity. It is often necessary therefore to boost the host immune system, as may be achieved by coupling a peptide or polypeptide immunogen to a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers. Means for conjugating a polypeptide to a carrier protein are well known in the art and include glutaraldehyde, m-maleimidobencoyf-N-hydroxysuccinimide ester, carbodiimide and bis-diazotized benzidine.

As is also well known in the art, the immunogenicity of a particular immunogen composition can be enhanced by the use of non-specific stimulators of the immune response, known as adjuvants. Exemplary and preferred adjuvants include complete Freund's adjuvant (a non-specific stimulator of the immune response containing killed *Mycoboacterium tuberculosis*), incomplete Freund's adjuvants and aluminum hydroxide adjuvant.

The amount of immunogen composition used in the production of polyclonal antibodies varies upon the nature of the immunogen as well as the animal used for immunization. A variety of routes can be used to administer the immunogen (subcutaneous, intramuscular, intradermal, intravenous and intraperitoneal). The production of polyclonal antibodies may be monitored by sampling blood of the immunized animal at various points following immunization. A second, booster, injection may also be given. The process of boosting and titering is repeated until a suitable titer is achieved. When a desired level of immunogenicity is obtained, the immunized animal can be bled and the serum isolated and stored, and/or the animal can be used to generate mAbs.

mAbs may be readily prepared through use of well-known techniques, such as those exemplified in U.S. Pat. No. 4,196,265, incorporated herein by reference. Typically, this technique involves immunizing a suitable animal with a selected immunogen composition, e.g., a purified or partially purified OIP-1γ protein, polypeptide or peptide. The immunizing composition is administered in a manner effective to stimulate antibody producing cells. Rodents such as mice and rats are preferred animals, however, the use of rabbit, sheep frog cells is also possible. The use of rats may provide certain advantages (Goding, 1986), but mice are preferred, with the BALB/c mouse being most preferred as this is most routinely used and generally gives a higher percentage of stable fusions.

Following immunization, somatic cells with the potential for producing antibodies, specifically B-lymphocytes (B-cells), are selected for use in the mAb generating protocol. These cells may be obtained from biopsied spleens, tonsils or lymph nodes, or from a peripheral blood sample. Spleen cells and peripheral blood cells are preferred, the former because they are a rich source of antibody-producing cells that are in the dividing plasmablast stage, and the latter because peripheral blood is easily accessible. Often, a panel of animals will have been immunized and the spleen of animal with the highest antibody titer will be removed and the spleen lymphocytes obtained by homogenizing the spleen with a syringe. Typically, a spleen from an immunized mouse contains approximately $5 \times 10^7$ to $2 \times 10^8$ lymphocytes.

The antibody-producing B lymphocytes from the immunized animal are then fused with cells of an immortal myeloma cell, generally one of the same species as the animal that was immunized. Myeloma cell lines suited for use in hybridoma-producing fusion procedures preferably are non-antibody-producing, have high fusion efficiency, and enzyme deficiencies that render then incapable of growing in certain selective media which support the growth of only the desired fused cells (hybridomas).

Any one of a number of myeloma cells may be used, as are known to those of skill in the art (Goding, 1986; Campbell, 1984). For example, where the immunized animal is a mouse, one may use P3-X63/Ag8, X63-Ag8.653, NS1/1.Ag 4 1, Sp210-Ag14, FO, NSO/U, MPC-11, MPC11-X45-GTG 1.7 and S194/5XX0 Bul; for rats, one may use R210.RCY3, Y3-Ag 1.2.3, IR983F and 4B210; and U-266, GM1500-GRG2, LICR-LON-HMy2 and UC729-6 are all useful in connection with human cell fusions.

One preferred murine myeloma cell is the NS-1 myeloma cell line (also termed P3-NS-1-Ag4-1), which is readily available from the NIGMS Human Genetic Mutant Cell Repository by requesting cell line repository number GM3573. Another mouse myeloma cell line that may be used is the 8-azaguanine-resistant mouse murine myeloma SP2/0 non-producer cell line.

Methods for generating hybrids of antibody-producing spleen or lymph node cells and myeloma cells usually comprise mixing somatic cells with myeloma cells in a 2:1 ratio, though the ratio may vary from about 20:1 to about 1:1, respectively, in the presence of an agent or agents (chemical or electrical) that promote the fusion of cell membranes. Fusion methods using Sendai virus have been described (Kohler and Milstein, 1975; 1976), and those using polyethylene glycol (PEG), such as 37% (v/v) PEG, by Gefter et al, (1977). The use of electrically induced fusion methods is also appropriate (Goding, 1986).

Fusion procedures usually produce viable hybrids at low frequencies, about $1 \times 10^{-6}$ to $1 \times 10^{-8}$. However, this does not pose a problem, as the viable, fused hybrids are differentiated from the parental, unfused cells (particularly the unfused myeloma cells that would normally continue to divide indefinitely) by culturing in a selective medium. The selective medium is generally one that contains an agent that blocks the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides (HAT medium). Where azaserine is used, the media is supplemented with hypoxanthine.

The preferred selection medium is HAT. Only cells capable of operating nucleotide salvage pathways are able to survive in HAT medium. The myeloma cells are defective in key enzymes of the salvage pathway, e.g., hypoxanthine phosphoribosyl transferase (HPRT), and they cannot survive. The B-cells can operate this pathway, but they have a limited life span in culture and generally die within about two weeks. Therefore, the only cells that can survive in the selective media are those hybrids formed from myeloma and B-cells.

This culturing provides a population of hybridomas from which specific hybridomas are selected. Typically, selection of hybridomas is performed by culturing the cells by single-clone dilution in microtiter plates, followed by testing the individual clonal supernatants (after about two to three weeks) for the desired reactivity. The assay should be sensitive, simple and rapid, such as radioimmunoassays, enzyme immunoassays, cytotoxicity assays, plaque assays, dot immunobinding assays, and the like.

The selected hybridomas would then be serially diluted and cloned into individual antibody-producing cell lines, which clones can then be propagated indefinitely to provide mAbs. The cell lines may be exploited for mAb production in two basic ways. A sample of the hybridoma can be injected (often into the peritoneal cavity) into a histocompatible animal of the type that was used to provide the somatic and myeloma cells for the original fusion. The injected animal develops tumors secreting the specific monoclonal antibody produced by the fused cell hybrid. The body fluids of the animal, such as serum or ascites fluid, can then be tapped to provide mAbs in high concentration. The individual cell lines could also be cultured in vitro, where the mAbs are naturally secreted into the culture medium from which they can be readily obtained in high concentrations. mAbs produced by either means may be further purified, if desired, using filtration, centrifugation and various chromatographic methods such as HPLC or affinity chromatography.

4.8 Pharmaceutical Compositions

The pharmaceutical compositions disclosed herein may be orally administered, for example, with an inert diluent or with an assimilable edible carrier, or they may be enclosed in hard or soft shell gelatin capsule, or they may be compressed into tablets, or they may be incorporated directly with the food of the diet. For oral therapeutic administration, the active compounds may be incorporated with excipients and used in the form of ingestible tablets, buccal tables, troches, capsules, elixirs, suspensions, syrups, wafers, and the like. Such compositions and preparations should contain at least 0.1% of active compound. The percentage of the compositions and preparations may, of course, be varied and may conveniently be between about 2 to about 60% of the weight of the unit. The amount of active compounds in such therapeutically useful compositions is such that a suitable dosage will be obtained.

The tablets, troches, pills, capsules and the like may also contain the following: a binder, as gum tragacanth, acacia, cornstarch, or gelatin; excipients, such as dicalcium phosphate; a disintegrating agent, such as corn starch, potato starch, alginic acid and the like; a lubricant, such as magnesium stearate; and a sweetening agent, such as sucrose, lactose or saccharin may be added or a flavoring agent, such as peppermint, oil of wintergreen, or cherry flavoring. When the dosage unit form is a capsule, it may contain, in addition to materials of the above type, a liquid carrier. Various other materials may be present as coatings or to otherwise modify the physical form of the dosage unit. For instance, tablets, pills, or capsules may be coated with shellac, sugar or both. A syrup of elixir may contain the active compounds sucrose as a sweetening agent methyl and propylparabens as preservatives, a dye and flavoring, such as cherry or orange flavor. Of course, any material used in preparing any dosage unit form should be pharmaceutically pure and substantially non-toxic in the amounts employed. In addition, the active compounds may be incorporated into sustained-release preparation and formulations.

The active compounds may also be administered parenterally or intraperitoneally. Solutions of the active compounds as free base or pharmacologically acceptable salts can be prepared in water suitably mixed with a surfactant, such as hydroxypropylcellulose. Dispersions can also be prepared in glycerol, liquid polyethylene glycols, and mixtures thereof and in oils. Under ordinary conditions of storage and use, these preparations contain a preservative to prevent the growth of microorganisms.

The pharmaceutical forms suitable for injectable use include sterile aqueous solutions or dispersions and sterile powders for the extemporaneous preparation of sterile injectable solutions or dispersions. In all cases the form must be sterile and must be fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (for example, glycerol, propylene glycol, and liquid polyethylene glycol, and the like), suitable mixtures thereof, and vegetable oils. The proper fluidity can be maintained, for example, by the use of a coating, such as lecithin, by the maintenance of the required particle size in the case of dispersion and by the use of surfactants. The prevention of the action of microorganisms can be brought about by various antibacterial ad antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

Sterile injectable solutions are prepared by incorporating the active compounds in the required amount in the appropriate solvent with various of the other ingredients enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

As used herein, "pharmaceutically acceptable carrier" includes any and all solvents, dispersion media, coatings, antibacterial and antifungal agents, isotonic and absorption delaying agents and the like. The use of such media and agents for pharmaceutical active substances is well known in the art. Except insofar as any conventional media or agent is incompatible with the active ingredient, its use in the therapeutic compositions is contemplated. Supplementary active ingredients can also be incorporated into the compositions.

For oral prophylaxis the polypeptide may be incorporated with excipients and used in the form of non-ingestible mouthwashes and dentifrices. A mouthwash may be prepared incorporating the active ingredient in the required amount in an appropriate solvent, such as a sodium borate solution (Dobell's Solution). Alternatively, the active ingredient may be incorporated into an antiseptic wash containing sodium borate, glycerin and potassium bicarbonate. The active ingredient may also be dispersed in dentifrices, including: gels, pastes, powders and slurries. The active ingredient may be added in a therapeutically effective amount to a paste dentifrice that may include water, binders, abrasives, flavoring agents, foaming agents, and humectants.

The phrase "pharmaceutically acceptable" refers to molecular entities and compositions that do not produce an allergic or similar untoward reaction when administered to a human. The preparation of an aqueous composition that contains a protein as an active ingredient is well understood in the art. Typically, such compositions are prepared as injectables, either as liquid solutions or suspensions; solid forms suitable for solution in, or suspension in, liquid prior to injection can also be prepared. The preparation can also be emulsified.

The composition can be formulated in a neutral or salt form. Pharmaceutically acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like.

Upon formulation, solutions will be administered in a manner compatible with the dosage formulation and in such amount as is therapeutically effective. The formulations are easily administered in a variety of dosage forms such as injectable solutions, drug release capsules and the like.

For parenteral administration in an aqueous solution, for example, the solution should be suitably buffered if necessary and the liquid diluent first rendered isotonic with sufficient saline or glucose. These particular aqueous solutions are especially suitable for intravenous, intramuscular, subcutaneous and intraperitoneal administration. In this connection, sterile aqueous media which can be employed will be known to those of skill in the art in light of the present disclosure. For example, one dosage could be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035–1038 and 1570–1580). Some variation in dosage will necessarily occur depending on the condition of the subject being treated. The person responsible for administration will, in any event, determine the appropriate dose for the individual subject. Moreover, for human administration, preparations should meet sterility, pyrogenicity, general safety and purity standards as required by FDA Office of Biologics standards.

4.9 Expression Vectors

The present invention contemplates an expression vector comprising a polynucleotide encoding polypeptides that inhibit osteoclast formation. Thus, in one embodiment an expression vector is an isolated and purified DNA molecule comprising a promoter operatively linked to an coding region that encodes a polypeptide of the present invention, which coding region is operatively linked to a transcription-terminating region, whereby the promoter drives the transcription of the coding region.

As used herein, the term "operatively linked" means that a promoter is connected to a coding region in such a way that the transcription of that coding region is controlled and regulated by that promoter. Means for operatively linking a promoter to a coding region are well known in the art.

Where an expression vector of the present invention is to be used to transform a cell, a promoter is selected that has the ability to drive expression in that type of cell. Promoters that function in eukaryotic cells are also well known in the art. Useful in expressing the polypeptide in such cells are promoters that are inducible, viral, synthetic, constitutive as described (Poszkowski et al., 1989; Odell et al., 1985), and temporally regulated, spatially regulated, and spatio-temporally regulated (Chau et al., 1989).

A promoter is also selected for its ability to direct the transformed cell's transcriptional activity to the coding region. Structural genes can be driven by a variety of promoters in human tissues. Promoters can be near-constitutive, such as the CMV promoter, or tissue-specific or developmentally specific promoters such as the tartrate resistance acid phosphatase or osteocalcin promoters.

Where the promoter is a near-constitutive promoter such as a CMV promoter, increases in polypeptide expression are found in a variety of human tissues (e.g., muscle or bone). Alternatively, the effects of transformation can be directed to specific human tissues by using human integrating vectors containing a tissue-specific promoter.

The choice of which expression vector and ultimately to which promoter a polypeptide coding region is operatively linked depends directly on the functional properties desired, e.g., the location and timing of protein expression, and the host cell to be transformed. These are well known limitations inherent in the art of constructing recombinant DNA molecules. However, a vector useful in practicing the present invention is capable of directing the expression of the polypeptide coding region to which it is operatively linked.

Typical vectors useful for expression of genes in higher mammals are well known in the art and include vectors derived from the CMV promoter or LTRs from retroviral constructs.

RNA polymerase transcribes a coding DNA sequence through a site where polyadenylation occurs. Typically, DNA sequences located a few hundred base pairs downstream of the polyadenylation site serve to terminate transcription. Those DNA sequences are referred to herein as transcription-termination regions. Those regions are required for efficient polyadenylation of transcribed messenger RNA (mRNA).

Means for preparing expression vectors are well known in the art. Expression (transformation vectors) used to transform cells and methods of making those vectors are described in U.S. Pat. Nos. 4,971,908, 4,940,835, 4,769,061 and 4,757,011, the disclosures of which are incorporated herein by reference. Those vectors can be modified to include a coding sequence in accordance with the present invention.

A variety of methods has been developed to operatively link DNA to vectors via complementary cohesive termini or blunt ends. For instance, complementary homopolymer tracts can be added to the DNA segment to be inserted and to the vector DNA. The vector and DNA segment are then joined by hydrogen bonding between the complementary homopolymeric tails to form recombinant DNA molecules.

A coding region that encodes a polypeptide having the ability to confer OIP activity to a cell is preferably a chimeric, or a functional equivalent of one or more of this or related sequences.

4.10 Gene Transfer

Several methods are available for introducing a gene encoding a desired protein into a cell. Techniques include electroporation, microprojectile bombardment and, as previously discussed, transfection with viral-adapted vectors.

4.10.1 Electroporation

The application of brief, high-voltage electric pulses to a variety of animal and plant cells leads to the formation of nanometer-sized pores in the plasma membrane. DNA is taken directly into the cell cytoplasm either through these pores or as a consequence of the redistribution of membrane components that accompanies closure of the pores. Electroporation can be extremely efficient and can be used both for transient expression of clones genes and for establishment of cell lines that carry integrated copies of the gene of interest. Electroporation, in contrast to calcium phosphate-mediated transfection and protoplast fusion, frequently gives rise to cell lines that carry one, or at most a few, integrated copies of the foreign DNA.

The introduction of DNA by means of electroporation, is well-known to those of skill in the art. In this method, certain cell wall-degrading enzymes, such as pectin-degrading enzymes, are employed to render the target recipient cells more susceptible to transformation by electroporation than untreated cells. Alternatively, recipient cells are made more susceptible to transformation, by mechanical wounding. One would partially degrade the cell walls of the chosen cells by exposing them to pectin-degrading enzymes (pectolyases) or mechanically wounding in a controlled manner. Such cells would then be recipient to DNA transfer by electroporation, which may be carried out at this stage, and transformed cells then identified by a suitable selection or screening protocol dependent on the nature of the newly incorporated DNA.

4.10.2 Microprojectile Bombardment

A further advantageous method for delivering transforming DNA segments to plant cells is microprojectile bombardment. In this method, particles may be coated with nucleic acids and delivered into cells by a propelling force. Exemplary particles include those comprised of tungsten, gold, platinum, and the like.

For the bombardment, cells in suspension are preferably concentrated on filters or solid culture medium. Alternatively, immature embryos or other target cells may be arranged on solid culture medium. The cells to be bombarded are positioned at an appropriate distance below the macroprojectile stopping plate. If desired, one or more screens are also positioned between the acceleration device and the cells to be bombarded. Through the use of techniques set forth herein one may obtain up to 1000 or more foci of cells transiently expressing a marker gene. The number of cells in a focus which express the exogenous gene product 48 hours post-bombardment often range from 1 to 10 and average 1 to 3.

In bombardment transformation, one may optimize the prebombardment culturing conditions and the bombardment parameters to yield the maximum numbers of stable transformants. Both the physical and biological parameters for bombardment are important in this technology. Physical factors are those that involve manipulating the DNA/microprojectile precipitate or those that affect the flight and velocity of either the macro- or microprojectiles. Biological factors include all steps involved in manipulation of cells before and immediately after bombardment, the osmotic adjustment of target cells to help alleviate the trauma associated with bombardment, and also the nature of the transforming DNA, such as linearized DNA or intact supercoiled plasmids.

Accordingly, it is contemplated that one may wish to adjust various of the bombardment parameters in small scale studies to fully optimize the conditions. One may particularly wish to adjust physical parameters such as gap distance, flight distance, tissue distance, and helium pressure. One may also minimize the trauma reduction factors (TRFs) by modifying conditions which influence the physiological state of the recipient cells and which may therefore influence transformation and integration efficiencies. For example, the osmotic state, tissue hydration and the subculture stage or cell cycle of the recipient cells may be adjusted for optimum transformation. The execution of other routine adjustments will be known to those of skill in the art in light of the present disclosure.

The methods of particle-mediated transformation is well-known to those of skill in the art. U.S. Pat. No. 5,015,580 (specifically incorporated herein by reference) describes the transformation of soybeans using such a technique.

4.11 Immunoprecipitation

The antibodies of the present invention are particularly useful for the isolation of antigens by immunoprecipitation. Immunoprecipitation involves the separation of the target antigen component from a complex mixture, and is used to discriminate or isolate minute amounts of protein. For the isolation of membrane proteins, cells must be solubilized into detergent micelles. Nonionic salts are preferred, since other agents such as bile salts, precipitate at acid pH or in the presence of bivalent cations.

In an alternative embodiment, the antibodies of the present invention are useful for the close juxtaposition of two antigens. This is particularly useful for increasing the localized concentration of antigens, e.g., enzyme-substrate pairs.

4.12 Western Blots

The compositions of the present invention will find great use in immunoblot or Western blot analysis. The anti-OIP antibodies may be used as high-affinity primary reagents for the identification of proteins immobilized onto a solid support matrix, such as nitrocellulose, nylon or combinations thereof. In conjunction with immunoprecipitation, followed by gel electrophoresis, these may be used as a single step reagent for use in detecting antigens against which secondary reagents used in the detection of the antigen cause an adverse background. This is especially useful when the antigens studied are immunoglobulins (precluding the use of immunoglobulins binding bacterial cell wall components), the antigens studied cross-react with the detecting agent, or they migrate at the same relative molecular weight as a cross-reacting signal.

Immunologically-based detection methods for use in conjunction with Western blotting include enzymatically-, radiolabel-, or fluorescently-tagged secondary antibodies against the toxin moiety are considered to be of particular use in this regard.

4.13 Vaccines

The present invention contemplates vaccines for use in both active and passive immunization embodiments. Immunogenic compositions, proposed to be suitable for use as a vaccine, may be prepared most readily directly from immunogenic OIP peptides prepared in a manner disclosed herein. Preferably the antigenic material is extensively dialyzed to remove undesired small molecular weight molecules and/or lyophilized for more ready formulation into a desired vehicle.

The preparation of vaccines which contain OIP peptide sequences as active ingredients is generally well understood in the art, as exemplified by U.S. Pat. Nos. 4,608,251; 4,601,903; 4,599,231; 4,599,230; 4,596,792; and 4,578,770, all incorporated herein by reference. Typically, such vaccines are prepared as injectables. Either as liquid solutions or suspensions: solid forms suitable for solution in, or suspension in, liquid prior to injection may also be prepared. The preparation may also be emulsified. The active immunogenic ingredient is often mixed with excipients which are pharmaceutically acceptable and compatible with the active ingredient. Suitable excipients are, for example, water, saline, dextrose, glycerol, ethanol, or the like and combinations thereof. In addition, if desired, the vaccine may contain minor amounts of auxiliary substances such as wetting or emulsifying agents, pH buffering agents, or adjuvants which enhance the effectiveness of the vaccines.

Vaccines may be conventionally administered parenterally, by injection, for example, either subcutaneously or intramuscularly. Additional formulations which are suitable for other modes of administration include suppositories and, in some cases, oral formulations. For suppositories, traditional binders and carriers may include, for example, polyalkalene glycols or triglycerides: such suppositories may be formed from mixtures containing the active ingredient in the range of about 0.5% to about 10%, preferably about 1 to about 2%. Oral formulations include such normally employed excipients as, for example, pharmaceutical grades of mannitol, lactose, starch, magnesium stearate, sodium saccharine, cellulose, magnesium carbonate and the like. These compositions take the form of solutions, suspensions, tablets, pills, capsules, sustained release formulations or powders and contain about 10 to about 95% of active ingredient, preferably about 25 to about 70%.

The OIP-derived peptides of the present invention may be formulated into the vaccine as neutral or salt forms. Pharmaceutically-acceptable salts, include the acid addition salts (formed with the free amino groups of the peptide) and those which are formed with inorganic acids such as, for example, hydrochloric or phosphoric acids, or such organic acids as acetic, oxalic, tartaric, mandelic, and the like. Salts formed with the free carboxyl groups may also be derived from inorganic bases such as, for example, sodium, potassium, ammonium, calcium, or ferric hydroxides, and such organic bases as isopropylamine, trimethylamine, 2-ethylamino ethanol, histidine, procaine, and the like.

The vaccines are administered in a manner compatible with the dosage formulation, and in such amount as will be therapeutically effective and immunogenic. The quantity to be administered depends on the subject to be treated, including, e.g., the capacity of the individual's immune system to synthesize antibodies, and the degree of protection desired. Precise amounts of active ingredient required to be administered depend on the judgment of the practitioner. However, suitable dosage ranges are of the order of several hundred micrograms active ingredient per vaccination. Suitable regimes for initial administration and booster shots are also variable, but are typified by an initial administration followed by subsequent inoculations or other administrations.

The manner of application may be varied widely. Any of the conventional methods for administration of a vaccine are applicable. These are believed to include oral application on a solid physiologically acceptable base or in a physiologically acceptable dispersion, parenterally, by injection or the like. The dosage of the vaccine will depend on the route of administration and will vary according to the size of the host.

Various methods of achieving adjuvant effect for the vaccine includes use of agents such as aluminum hydroxide or phosphate (alum), commonly used as about 0.05 to about 0.1% solution in phosphate buffered saline, admixture with synthetic polymers of sugars (Carbopol®) used as an about 0.25% solution, aggregation of the protein in the vaccine by heat treatment with temperatures ranging between about 70° to about 101° C. for a 30-second to 2-minute period, respectively. Aggregation by reactivating with pepsin treated (Fab) antibodies to albumin, mixture with bacterial cells such as *C. parvum* or endotoxins or lipopolysaccharide components of Gram-negative bacteria, emulsion in physiologically acceptable oil vehicles such as mannide monooleate (Aracel A) or emulsion with a 20% solution of a perfluordcarbon (Fluosol-DA®) used as a block substitute may also be employed.

In many instances, it will be desirable to have multiple administrations of the vaccine, usually not exceeding six vaccinations, more usually not exceeding four vaccinations and preferably one or more, usually at least about three vaccinations. The vaccinations will normally be at from two to twelve week intervals, more usually from three to five week intervals. Periodic boosters at intervals of 1–5 years, usually three years, will be desirable to maintain protective levels of the antibodies. The course of the immunization may be followed by assays for antibodies for the supernatant antigens. The assays may be performed by labeling with conventional labels, such as radionuclides, enzymes, fluorescents, and the like. These techniques are well known and may be found in a wide variety of patents, such as U.S. Pat. Nos. 3,791,932; 4,174,384 and 3,949,064, as illustrative of these types of assays.

4.14 DNA Segments

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a DNA segment encoding an OIP peptide in its natural environment. Such promoters may include promoters normally associated with other genes, and/or promoters isolated from any viral, prokaryotic (e.g., bacterial), eukaryotic (e.g., fungal, yeast, plant, or animal)

cell, and particularly those of mammalian cells. Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al., 1989. The promoters employed may be constitutive, or inducible, and can be used under the appropriate conditions to direct high level expression of the introduced DNA segment, such as is advantageous in the large-scale production of recombinant proteins or peptides. Appropriate promoter/expression systems contemplated for use in high-level expression include, but are not limited to, the Pichia expression vector system (Pharmacia LKB Biotechnology), a baculovirus system for expression in insect cells, or any suitable yeast or bacterial expression system.

In connection with expression embodiments to prepare recombinant proteins and peptides, it is contemplated that longer DNA segments will most often be used, with DNA segments encoding the entire peptide sequence being most preferred. However, it will be appreciated that the use of shorter DNA segments to direct the expression of OIP peptides or epitopic core regions, such as may be used to generate anti-OIP antibodies, also falls within the scope of the invention. DNA segments that encode OIP peptide antigens from about 10 to about 100 amino acids in length, or more preferably, from about 20 to about 80 amino acids in length, or even more preferably, from about 30 to about 70 amino acids in length are contemplated to be particularly useful.

In addition to their use in directing the expression of OIP peptides of the present invention, the nucleic acid sequences contemplated herein also have a variety of other uses. For example, they also have utility as probes or primers in nucleic acid hybridization embodiments. As such, it is contemplated that nucleic acid segments that comprise a sequence region that consists of at least an about 14-nucleotide long contiguous sequence that has the same sequence as, or is complementary to, an about 14-nucleotide long contiguous DNA segment of SEQ ID NO:3 will find particular utility. Longer contiguous identical or complementary sequences, e.g., those of about 20, 30, 40, 50, 100, 200, (including all intermediate lengths) and even those up to and including about 1950-bp (full-length) sequences will also be of use in certain embodiments.

The ability of such nucleic acid probes to specifically hybridize to OIP-encoding sequences will enable them to be of use in detecting the presence of complementary sequences in a given sample. However, other uses are envisioned, including the use of the sequence information for the preparation of mutant species primers, or primers for use in preparing other genetic constructions.

Nucleic acid molecules having sequence regions consisting of contiguous nucleotide stretches of about 14, 15–20, 30, 40, 50, 100, 200, 500, 800 or even of about 1000 to about 2000 nucleotides or so, identical or complementary to the DNA sequence of SEQ ID NO:3, are particularly contemplated as hybridization probes for use in, e.g., Southern and Northern blotting. Smaller fragments will generally find use in hybridization embodiments, wherein the length of the contiguous complementary region may be varied, such as between about 10–14 and up to about 100 nucleotides, but larger contiguous complementarity stretches may be used, according to the length complementary sequences one wishes to detect.

The use of a hybridization probe of about 14 nucleotides in length allows the formation of a duplex molecule that is both stable and selective. Molecules having contiguous complementary sequences over stretches greater than 14 bases in length are generally preferred, though, in order to increase stability and selectivity of the hybrid, and thereby improve the quality and degree of specific hybrid molecules obtained. One will generally prefer to design nucleic acid molecules having gene-complementary stretches of about 15 to about 20 contiguous nucleotides, or even longer where desired.

Of course, fragments may also be obtained by other techniques such as, e.g., by mechanical shearing or by restriction enzyme digestion. Small nucleic acid segments or fragments may be readily prepared by, for example, directly synthesizing the fragment by chemical means, as is commonly practiced using an automated oligonucleotide synthesizer. Also, fragments may be obtained by application of nucleic acid reproduction technology, such as PCR, by introducing selected sequences into recombinant vectors for recombinant production, and by other recombinant DNA techniques generally known to those of skill in the art of molecular biology.

Accordingly, the nucleotide sequences of the invention may be used for their ability to selectively form duplex molecules with complementary stretches of DNA fragments. Depending on the application envisioned, one will desire to employ varying conditions of hybridization to achieve varying degrees of selectivity of probe towards target sequence. For applications requiring high selectivity, one will typically desire to employ relatively stringent conditions to form the hybrids, e.g., one will select relatively low salt and/or high temperature conditions, such as provided by about 0.02 M to about 0.15 M NaCl at temperatures of about 50° C. to about 70° C. Such selective conditions of high stringency tolerate little, if any, mismatch between the probe and the template or target strand, and would be particularly suitable for isolating OIP-encoding DNA segments. Detection of DNA segments via hybridization is well-known to those of skill in the art, and the teachings of U.S. Pat. Nos. 4,965,188 and 5,176,995 (each incorporated herein by reference) are exemplary of the methods of hybridization analyses. Teachings such as those found in the texts of Maloy et al, 1994; Segal, 1976; Prokop, 1991; and Kuby, 1994, are particularly relevant.

Of course, for some applications, for example, where one desires to prepare mutants employing a mutant primer strand hybridized to an underlying template or where one seeks to isolate OIP-encoding sequences from related species, functional equivalents, or the like, less stringent hybridization conditions will typically be needed in order to allow formation of the heteroduplex. In these circumstances, one may desire to employ conditions such as about 0.15 M to about 0.9 M salt, at temperatures ranging from about 20° C. to about 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it will be advantageous to employ nucleic acid sequences of the present invention in combination with an appropriate means, such as a label, for determining hybridization. A wide variety of appropriate indicator means are known in the art, including fluorescent, radioactive, enzymatic or other ligands, such as avidin/ biotin, which are capable of giving a detectable signal. In preferred embodiments, one will likely desire to employ a fluorescent label or an enzyme tag, such as urease, alkaline phosphatase or peroxidase, instead of radioactive or other environmental undesirable reagents. In the case of enzyme tags, calorimetric indicator substrates are known that can be employed to provide a means visible to the human eye or spectrophotometrically, to identify specific hybridization with complementary nucleic acid-containing samples.

In general, it is envisioned that the hybridization probes described herein will be useful both as reagents in solution hybridization as well as in embodiments employing a solid phase. In embodiments involving a solid phase, the test DNA (or RNA) is adsorbed or otherwise affixed to a selected matrix or surface. This fixed, single-stranded nucleic acid is then subjected to specific hybridization with selected probes under desired conditions. The selected conditions will depend on the particular circumstances based on the particular criteria required (depending, for example, on the G+C content, type of target nucleic acid, source of nucleic acid, size of hybridization probe, etc.). Following washing of the hybridized surface so as to remove nonspecifically bound probe molecules, specific hybridization is detected, or even quantitated, by means of the label.

4.15 ELISAs

ELISAs may be used in conjunction with the invention. In an ELISA assay, proteins or peptides incorporating OIP antigenic sequences are immobilized onto a selected surface, preferably a surface exhibiting a protein affinity such as the wells of a polystyrene microtiter plate. After washing to remove incompletely adsorbed material, it is desirable to bind or coat the assay plate wells with a nonspecific protein that is known to be antigenically neutral with regard to the test antisera such as bovine serum albumin (BSA), casein or solutions of powdered milk. This allows for blocking of nonspecific adsorption sites on the immobilizing surface and thus reduces the background caused by nonspecific binding of antisera onto the surface.

After binding of antigenic material to the well, coating with a non-reactive material to reduce background, and washing to remove unbound material, the immobilizing surface is contacted with the antisera or clinical or biological extract to be tested in a manner conducive to immune complex (antigen/antibody) formation. Such conditions preferably include diluting the antisera with diluents such as BSA, bovine gamma globulin (BGG) and phosphate buffered saline (PBS)/Tween®. These added agents also tend to assist in the reduction of nonspecific background. The layered antisera is then allowed to incubate for from about 2 to about 4 hr, at temperatures preferably on the order of about 25° to about 27° C. Following incubation, the antisera-contacted surface is washed so as to remove non-immunocomplexed material. A preferred washing procedure includes washing with a solution such as PBS/Tween®, or borate buffer.

Following formation of specific immunocomplexes between the test sample and the bound antigen, and subsequent washing, the occurrence and even amount of immunocomplex formation may be determined by subjecting same to a second antibody having specificity for the first. To provide a detecting means, the second antibody will preferably have an associated enzyme that will generate a color development upon incubating with an appropriate chromogenic substrate. Thus, for example, one will desire to contact and incubate the antisera-bound surface with a urease, alkaline phosphatase or peroxidase-conjugated anti-human IgG for a period of time and under conditions which favor the development of immunocomplex formation (e.g., incubation for 2 hr at room temperature in a PBS-containing solution such as PBS/Tween®).

After incubation with the second enzyme-tagged antibody, and subsequent to washing to remove unbound material, the amount of label is quantified by incubation with a chromogenic substrate such as urea and bromocresol purple or 2,2'-azino-di-(3-ethyl-benzthiazoline)-6-sulfonic acid (ABTS) and $H_2O_2$, in the case of peroxidase as the enzyme label. Quantitation is then achieved by measuring the degree of color generation, e.g., using a visible spectrum spectrophotometer.

5.0 EXAMPLES

The following examples are included to demonstrate preferred embodiments of the invention. It should be appreciated by those of skill in the art that the techniques disclosed in the examples which follow represent techniques discovered by the inventor to function well in the practice of the invention, and thus can be considered to constitute preferred modes for its practice. However, those of skill in the art should, in light of the present disclosure, appreciate that many changes can be made in the specific embodiments which are disclosed and still obtain a like or similar result without departing from the spirit and scope of the invention.

5.1 Example 1—Preparation of an OCL Library

The availability of OCL-like multinucleated cells (MNC) formed in human marrow cultures allowed determination of OCLs that produce factors that increase or decrease OCL formation and activity. cDNA expression libraries were prepared from highly purified human OCL-like MNC from normals, rather than trying to identify these factors in OCL conditioned media. MNC represent a readily available source of large numbers of normal cells that fulfill the function al criteria of OCL, i.e., express calcitonin receptors, contract in response to calcitonin and form resorption lacunae in calcified materials.

Approximately 750 ml of normal marrow from 25 donors was cultured with 1,25-$(OH)_2D_3$ for 3 weeks and then the OCL-like MNC were purified by immunomagnetic bead techniques with the 23c6 monoclonal antibody that identifies OCL-like MNC. RNA was prepared and cDNAs were reverse transcribed and approximately $10^6$ clones isolated. Southern blot analysis of the cDNAs prepared from this library showed the presence of both cDNAs for tartrate-resistant acid phosphatase (TRAP) and calcitonin receptor (CTR), demonstrating the osteoclastic nature of this library. The library was converted to a cDNA expression library using the pCDNAI expression vector. The library was divided into 200 pools containing 2000 clones each. The plasmid DNA prepared from each pool was then transiently transfected into the 293 cells, which overexpress recombinant protein to a 10-fold greater extent than COS cells, because of the presence of the E1A gene.

5.2 Example 2—Screening the Osteoclast Expression Library

Serum-free conditioned media from these 200 pools described in Example 1 were screened for activities that stimulated or inhibited OCL-like MNC formation in long-term human and murine marrow cultures with or without 1,25-$(OH)_2D_3$. Pools with stimulatory activity were screened by PCR™ for IL-1, IL-6, TGF-α and lymphotoxin, cytokines known to enhance or inhibit MNC formation. Those that were positive were not further characterized. An assay for TRAP activity in these cultures was developed to screen large numbers of pools repeatedly. This assay has been used successfully to identify the effects of 5 LO metabolites on-OCL activity (Gallwitz et al. 1993). As shown in FIG. 1, TRAP activity was directly proportional to the number of 23c6-positive MNC present in long-term marrow cultures treated with either 1,25-$(OH)_2D_3$, IL-1 or media.

Contaminating TRAP-positive mononuclear cells were removed by gently treating the cultures with trypsin, since mononuclear cells are lightly adherent to the plates and are easily released compared to the tightly adherent MNC. It was confirmed that the TRAP assay identifies all the pools in this library that increased 23c6 MNC formation. At least 5 pools were identified which contained clones that enhance OCL-like MNC formation in long-term human marrow cultures but do not contain IL-1, IL-6, etc., several of which are shown in FIG. 2, as well as 3 pools that inhibit MNC formation (e.g., pool 11).

5.3 Example 3—Identification of Novel Factors (OIPs) That Inhibit Osteoclast Formation and Bone Resorption The most active inhibitory pools were fractionated to a single clone identified as a novel gene product which inhibits MNC formation. As seen in FIG. 3 and FIG. 4, conditioned media obtained from 293 cells transfected with the OIP-1 cDNA expression clone significantly decreased OCL formation in both long-term human and murine marrow cultures in the presence of 1,25-$(OH)_2D_3$.

OIP-1 containing conditioned media also inhibited $^{45}$Ca release from fetal rat long bones stimulated by 1,25-$(OH)_2D_3$. A 45% inhibition of $^{45}$Ca release was observed in the presence of $10^{-9}$ M 1,25-$(OH)_2D_3$ compared to the mock transfected conditioned media (FIG. 5). This gene was sequenced (FIG. 6A and FIG. 6B, SEQ ID NO:1) and was found to be identical to a newly described Ly6 gene family protein (U.S. Pat. No. 5,468,612). Northern blot analysis showed that the OIP-1 protein is encoded by a 1.3 kb transcript which is expressed in most human tissues except pancreas (FIG. 7, SEQ ID NO:2).

The expression of Ly6A MRNA was transcriptionally induced in U937 cells upon treatment with IFN-α in contrast to IFN-γ (FIG. 8). These data demonstrated that OIP-1 is a potent inhibitor of OCL formation and bone resorption and that it is present in human tissues. The characterization of this factor provides important insights into the regulation of normal OCL. The finding that IFN enhanced OIP-1 expression suggested its role as a mediator of the inhibitory effects of IFN on the OCL.

5.4 Example 4—Synthesis of Recombinant OIP-1 Protein

In order to obtain sufficient quantities of OIP-1 protein for further characterization, the cloned cDNA in *E. coli* using the pET vector system was expressed, as previously done for OSF-1 (Reddy et al., 1995). These vectors permit expression and purification of a cloned protein by tagging the protein with $His_6$ residues which can be removed upon thrombin cleavage. Purification of the $His_6$-tagged OIP protein was accomplished by passing the *E. coli* extract through a nickel column and elution with imidazole.

*P. pastoris* yeast expression system using a pPIC 9 vector was employed which provides the advantages of eukaryotic expression including protein processing, folding and post-translational modifications (Romanos et al., 1992). This vector has a $His_6$ tag and a thrombin cleavage site added. The yeast system vector has been used successfully to express recombinant Annexin (FIG. 9). Once the active recombinant protein was obtained, careful multipoint dose-response curves were performed, using human and murine marrow cultures stimulated with $10^{-9}$ M 1,25-$(OH)_2D_3$ to assay recombinant OIP.

In addition, the effects of OIP-1 on PTH, IL-1 and TNF-α stimulated murine and human marrow cultures will be tested in a similar fashion. Polyclonal antibodies to OIP-1 will be produced by standard techniques in a manner similar to those used for the osteoclast stimulatory factor (OSF-1), as illustrated in FIG. 10. Specificity and titer will be confirmed by Western blot analysis. Any inhibition of the antibody on the effects of OIP-1 on OCL formation in 1,25-$(OH)_2D_3$ stimulated human marrow cultures will be determined. Controls for these studies will utilize preimmune serum from these rabbits. Immunocytochemical studies of the antibody will also be tested (Kurihara et al., 1990). Recombinant OIP-1 will be tested for its effects on the growth of erythroid progenitors (BFU-E), multipotent hematopoietic progenitors, MC3T3 fibroblasts, MG63 osteoblast-like cells, and the human marrow stromal cell line (Saka) which has recently been reported (Takahashi et al., 1995).

Briefly, hematopoietic progenitors will be assayed in methylcellulose cultures at $10^5$ cells/ml, in the presence of 1.0 μ/ml erythropoietin, 10 μg/ml GM-CSF and 10 ng/ml SCF, and varying concentrations of OIP. Fibroblasts, stromal cells and MG63 cells will be plated at $10^5$ cells/ml in a αMEM-10% fetal calf serum in the presence of varying concentrations of OIP-1, and the number of cells present after 72 hours will be determined.

5.5 Example 5—Mapping of the Functional Domain of the OIP-1 Protein and Structurally Significant Domains In order to map the functional domain of the OIP-1 protein, the OIP cDNA cloned into the Bluescript vector (pSK) will be subjected to deletion mutagenesis either by partial or complete appropriate restriction enzyme digestions or unidirectional Bal 31 exonuclease deletions (Misra, 1985). Initially, the C-terminal hydrophobic amino acid encoding sequences that serve as a signal sequence for attachment of the GPI anchor will be deleted. This will be done to assess the effects of the GPI anchor on OIP-1 activity.

Other deletions will be prepared based on the restriction map. The truncated cDNA ends will be filled using the Klenow large fragment of DNA Polymerase I and ligated with BamHI linkers providing termination codons in all three reading frames. The cDNA fragments can be ligated to the pET 14b vector in frame, and the deletion mutant proteins will be purified from the *E. coli* or *P. pastoris* extracts using a nickel column as previously described. The mutant forms of OIP-1 protein will be assayed for OCL suppressor activity using multipoint dose-response curves in long-term human and murine marrow culture assays to assess their ability and potency to inhibit 1,25-$(OH)_2D_3$ stimulated OCL formation and activity (Takahashi et al., 1988; MacDonald et al., 1987). The effects of varying concentrations of the truncated OIP constructs on bone resorption will be assessed in the fetal rat long bone assay as previously described (Raisz, 1965).

5.6 Example 6—In Vitro Site-Directed Mutagenesis

Once the functional domain in the OIP-1 and OIP-2 proteins are mapped, site-directed mutagenesis will be used to identify the specific amino acid residues required for activity. Mutagenesis of the OIPs cDNA will be performed using the Altered Site Mutagenesis System (Promega Corporation, Madison, Wis.) (Hutchinson et al., 1978). In brief, OIP cDNA will be ligated into the pALTER1 vector. Point mutations, which change specific amino acid residues, will be introduced into the insert with complementary mutagenic oligonucleotides according to the manufacturer's instructions.

In addition, the tertiary structural requirements for OIP activity will be examined. The tertiary protein structure of the Ly6 family proteins is highly conserved and contains 10 cysteine residues that form three loop structures connected by four disulfide bridges (Mao et al., 1996). Therefore, these cysteine residues at positions 23, 26, 35, 41, 48, 71, 75, 92, 93 and 98 individualy or in combination can be replaced with glycine or alanine are not expected to permit disulfide bond formation, resulting in a modified tertiary structure for OIP.

Other highly conserved amino acids such as asparagine at position 59 of SEQ ID NO:2, which is the putative GPI (glycosylphosphatidylinositol) linkage site and the 27 or 50 position leucine residue of SEQ ID NO:2 can also be mutagenized. After confirming the DNA sequences by dideoxynucleotide sequencing, mutant OIP-1 cDNA subcloned into recombinant protein synthesis vectors (pET or pPIC9) as described above may be used to generate the mutant OIP-1 proteins. The activities of the mutant OIP-1 proteins can be tested as described.

5.7 Example 7—Characterization of OIP Effects on Osteoclast Development

The results disclosed herein show that OIPs and suppress OCL formation in murine as well as human bone marrow cultures in the presence of 1,25-(OH)$_2$D$_3$. Suppressor activity associated with the OIPs at the level of OCL precursor proliferation or the effect of OIP on precursor fusion or maturational events can be determined, as well as effects of recombinant OIP in long-term human marrow cultures and more committed MNC precursors as described previously (Kurihara et al., 1990).

Particularly, the effect of OIP-1 and OIP-2 in suppressing the growth of proliferating MNC precursors by adding OIP-1 to long-term marrow cultures at time zero, adding $^3$H-thymidine (1 µci/ml), and incubating the cultures for 48 hours at 37° C. can be determined. The $^3$H-thymidine will be removed and excess unlabelled thymidine added, and the cultures continued for 3 weeks. At the end of the three-week culture period, the number of labeled nuclei per MNC formed will be determined. A decrease in the number of labeled nuclei/MNC and the total number of labeled nuclei will indicate that OIP inhibits proliferation of immature MNC precursors. These techniques have been used to demonstrate that colony-stimulating factors and TGF-α stimulate proliferation of MNC precursors (Mao et al., 1996).

The effect of OIP in suppressing the fusion of MNC precursors by determining the average number of nuclei per MNC can be assessed. These studies will provide information on the mechanisms responsible for OIP activity on MNC development but are not designed to determine its effects on bone resorption.

Decreased bone resorption occurs as a result of suppression of the bone-resorbing capacity of preformed OCL or inhibiting the formation of OCL. To determine the effects of OIP-1 on preformed OCL, purified populations of murine OCL (Akatsu et al., 1992) will be prepared and plated 100 OCL per dentine slice. Recombinant OIP will be added at varying concentrations to OCL in the presence of 1,25-(OH)$_2$D$_3$ (10$^{-9}$ M), and the number area of resorption lacunae formed and the number of OCL per dentine slice at the end of 24 h will be determined by image analysis techniques.

No new OCL formation occurs over the 24-hour culture period because the culture conditions do not support osteoclast formation during this time period. It is important to count the number of OCL per slice in these assays to determine if the number and area of pits/OCL decreases or if only a lower number of OCL are adherent to the dentine slice with OIP treatment compared to control cultures since decreased OCL number would result in decreased bone resorption. One must differentiate between decreased OCL production and inhibition of OCL activity causing decreased absorption. These studies will delineate the cellular effects of the OIP activity.

To determine the physiologic role of the OIP in vivo, the effects of OIP in the presence or absence of IL-1 in an in vivo system for OCL formation (Uy et al., 1995) will be determined. Briefly, OIP (1–100 µg/mouse) will be injected over the calvaria of mice treated with or without 1 ng 1,25-(OH)$_2$D$_3$ for 3 days, analogous to studies with IL-1. At the end of the study, the number of CFU-GM, more committed OCL precursors (assessed by MNC formation in long-term marrow cultures), and mature OCL (assessed by histomorphometry) will be determined (Boyce et al., 1995).

In situ hybridization studies with appropriate antisense oligoribonucleotides or oligonucleotides to determine if the factor produced is derived from OCL-like MNC or from mononuclear cells in these marrow cultures will be undertaken using methods previously described for IL-6 (Ohsaki et al., 1992). To further confirm that OIPs produced by activated human OCL, cells from giant cell tumors of bone by in situ hybridization for OIP-IRNA expression will be examined.

5.8 Example 8—OIP-2 Protein

A novel OIP-encoding gene was isolated from an OCL library as described in Examples 1 and 2. The 1.9 Kb cDNA (SEQ ID NO:3) encoded a protein of 46 kda having the amino acid sequence of SEQ ID NO:4. Northern Blot analysis of mRNA from several human tissues demonstrated that the gene was expressed ubiquitously with lower levels in brain and heart (FIG. 14).

The OIP-2 protein (SEQ ID NO:4) was detected in conditioned media from cos 293 cells transfected with OIP-2 cDNA as determined by PAGE, confirming that it was secreted.

The OIP-2 protein inhibited human and murine osteoclast formation in vitro (FIGS. 12 and 13) as well as bone resorption induced by PTHrp or 1,25(OH)$_2$ vitamin D$_3$ in fetal long bone assays (FIG. 11).

Synthesis of recombinant OIP-2 protein mapping the functional domain of OIP-2 proteins, in vitro site-directed mutagenesis and characterization of OIP-2's effect on osteoclast development may be carried out in a manner described in Examples 4–7.

5.9 Example 9—Source of Human Bone Marrow Samples

Normal adult subjects aged 25–65 years will be used in these studies. Approximately 20 normal aspirates will be used per year. No minors, pregnant females, institutionalized mentally disabled, or prisoners will be used. It is planned to use equal number of men and women, and the ethnic and racial composition of the normal donors will reflect that of the local population. Marrow donors will be anesthetized with 2% xylocaine, the marrow drawn aseptically and pressure dresses applied to the marrow site to prevent bleeding.

Animal Studies

Approximately 100 CB57 mice will be used in these studies. Animals will be between 4 to 6 weeks of age at the start of the study. Blood will be collected from mice by retroorbital bleeding, and the mice will be administered metofane for these procedures. In all cases, attempts will be made to sacrifice these animals before any of them become ill. Euthanasia will be provided by cervical dislocation.

All of the compositions and methods disclosed and claimed herein can be made and executed without undue experimentation in light of the present disclosure. While the compositions and methods of this invention have been described in terms of preferred embodiments, it will be apparent to those of skill in the art that variations may be applied to such compositions and methods and in the steps or in the sequence of steps of the methods described herein without departing from the concept, spirit and scope of the invention. More specifically, it will be apparent that certain agents which are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

6.0 REFERENCES

The following references, to the extent that they provide exemplary procedural or other details supplementary to those set forth herein, are specifically incorporated herein by reference.

Akatsu T, Tamura T, Takahashi N, Udagawa N, Tanaka S, Sasaki T, Yamaguchi A, Nagata N, Suda T, "Preparation and characterization of a mouse osteoclast-like multinucleated cell population," *J Bone Miner Res*, 7:1297–1306, 1992.

Al-Humidan A, Ralston S H, Hughes D E, Chapman K, Aarden L, Graham R, Russell G, Gowen M, "Interleukin-6 does not stimulate bone resorption in neonatal mouse calvariae," *J Bone Miner Res*, 6:3–8, 1991.

Alcantara O, Reddy S V, Roodman G D, Boldt D H, "Transcriptional regulation of the tartrate resistant acid phosphatase (TRAP) gene by iron," *Biochem J*, 289(2):421–425, 1994.

Bartkiewicz M, Hernando N, Reddy S V, Roodman G D, Baron R, "Characterization of the osteoclast vacuolar $H^+$-ATPase B-subunit," *Gene*, 160:157–164, 1995.

Boyce B F, Wright K, Reddy S V, Koop B A, Story B, Devlin R D, Leach R J, Roodman G D, Windle J J, "Targeting Simian virus 40 T antigen to the osteoclast in transgenic mice causes osteoclast tumors and transformation and apoptosis of osteoclasts," *Endocrinology*, 136:5751–5759, 1995.

Brackenhoff R H, Gerretsen M, Knippels E M, Dijk V M, Essen V H, Weghuis D O, Sinke R J, Snow G B, Dougen G A V, "The human E48 antigen, highly homologous to the murine Ly6 antigen ThB, is a GPI-anchored molecule apparently involved in keratinocyte cell-cell adhesion," *J Cell Biol*, 129:1677–1689, 1995.

Brandi M L, Hukkanen M, Umeda T, Moradi-Bidhendi N, Bianchi S, Gross S S, Polak J M, Macintyre I, "Bidirectional regulation of osteoclast function by nitric oxide synthase isoforms," *Proc Natl Acad Sci USA*, 92:2954–2958, 1995.

Chenu C, Kurihara N, Mundy G R, Roodman G D, "Prostaglandin E2 inhibits formation of osteoclast-like cells in long-term human marrow cultures but is not a mediator of the inhibitory effects of transforming growth factor-$\beta$," *J Bone Miner Res*, 5:677–681, 1990.

Chenu C, Pfeilschifter J, Mundy G R, Roodman G D, "Transforming growth factor beta inhibits formation of osteoclast-like cells in long-term human marrow cultures," *Proc Natl Acad Sci USA*, 85:5683–5687, 1996.

Coleman R E, Purohit O P, "Osteoclast inhibition for the treatment of bone metastasis," *Cancer Treatment Rev*, 19:79–103, 1993.

Davies J, Warwick J, Totty N, Philip R, Helfrich M, Horton M, "The osteoclast functional antigen, implicated in the regulation of bone resorption, is biochemically related to the vitronectin receptor," *J Cell Biol*, 109:1817–1826, 1989.

Devlin R D, Reddy S V, Roodman G D, "Annexin II increases osteoclast formation by stimulating the proliferation of osteoclast precursors in human marrow cultures," *J Bone Miner Res*, 1996.

Fisher J E, Caulfield M P, Sato M, Quartuccio H A, Gould R J, Garsky V M, Rodan G A, Rosenblatt M, "Inhibition of osteoclastic bone resorption in vivo by echistatin, an "Arginyl-Glycyl-Aspartyl" (RGD)-containing protein," *Endocrinology*, 132:1411–1413, 1993.

Friedman J, Raisz L G, "Thyrocalcitonin: Inhibitor of bone resorption in tissue culture," *Science*, 150:1465–1467, 1965.

Gallwitz W E, Mundy G R, Lee C H, Qiao M, Roodman G D, Raftery M, Gaskell S J, Bonewald L F, "5-Lipoxygenase metabolites of arachidonic acid stimulate isolated osteoclasts to resorb calcified matrices," *J Biol Chem*, 268:10087–10094, 1993.

Goldring S R, Schiller A L, Mankin H J, Dayer J M, Krane S M, "Characterization of cells from giant cell tumors of bone," *Clin Orthop*, 204:59–75, 1986.

Hall T J, Schaueblin J M, "Taxol inhibits osteoclastic bone resorption," *Calcif Tiss Intl*, 57:463–465, 1995.

Hentunen T A, Lakkakorpi P T, Rautiala T, Vaananen H K, "Inhibition of bone resorption by a monoclonal antibody that reacts with a 150 kD membrane protein in chicken osteoclasts," *J Bone Miner Res*, 6:1091–1097, 1991.

Horowitz M C, Fields A, DeMeo D, Qian H Y, Bothwell A L, Trepman E, "Expression and regulation of Ly6 differentiation antigens by murine osteoblasts," *Endocrinology*, 135(3):1032–43, 1994.

Hoyland J A, Freemont A J, Sharpe P T, "Interleukin-6, IL-6 receptor, and IL-6 nuclear factor gene expression in Paget's disease," *J Bone Miner Res*, 9:75–80, 1996.

Hutchinson C A, Phillips S, Edgell M H, "Mutagenesis at a specific position in a DNA sequence," *Biol Chem*, 253:6551–6560, 1978.

Jilka R L, Hangoc G, Girasole G, Passeri G, Williams D C, Abrams J S, Boyce B, Broxmeyer H, Manolagas S C, "Increased osteoclast development after estrogen loss: mediation by interleukin-6," *Science*, 257:88–91, 1992.

Kurihara N, Bertolini D, Suda T, Akiyama Y, Roodman G D, "IL-6 stimulates osteoclast-like multinucleated cell formation in long-term human marrow cultures by inducing IL-1 release," *J Immunol*, 144:4226–4230, 1990.

Kurihara N, Chenu C, Miller M, Civin C, Roodman G D, "Identification of committed mononuclear precursors for osteoclast-like cells formed in long-term human marrow cultures," *Endocrinology*, 126:2733–2741, 1990.

MacDonald B R, Takahashi N, McManus L M, Holahan J, Mundy G R, Roodman G D, "Formation of multinucleated cells that respond to osteotropic hormones in long-term human bone marrow cultures," *Endocrinology*, 120:2326–2333, 1987.

Mao M, Yu M, Tong J H, Ye J, Zhu J, Hung Q H, Fu G, Yu L, Zhao S Y, Waxman S, Lanotte M, Wang Z Y, Tan J Z, Chan S J, Chen Z, "RIG-E, a human homolog of the murine Ly6 family, is induced by retinoic acid during the differentiation of acute promyelocytic leukemia cell," *Proc Natl Acad Sci USA*, 93:5910–5914, 1996.

Misra T K, "A new strategy to create ordered deletions for rapid nucleotide sequencing," *Gene*, 34:263–268, 1985.

Mundy G R, Roodman G D, "Ontogeny and function of the osteoclast," *J Bone Miner Res*, 5:209–30 281, 1987.

O'Neill R P J, Jones S J, Boyde A, Taylor M L, Arnett T R, "Effect of retinoic acid on the resorptive activity of chick osteoclasts in vitro," *Bone*, 13:23–27, 1992.

Ohsaki Y, Takahashi S, Scarcez T, Demulder A, Nishimura T, Williams R, Roodman G D, "Evidence for an autocrine/paracrine role for IL-6 in bone resorption by giant cell tumors of bone," *Endocrinology*, 131:2229–2234, 1992.

Ousler M J, "Osteoclast synthesis, secretion and activation of latent transforming growth factor beta," *J Bone Miner Res*, 9:443–452, 1994.

Pfeilschifter J, Mundy G R, "Modulation of transforming growth factor β in bone cultures by osteotropic hormones," *Proc Natl Acad Sci USA*, 84:2024–2028, 1987.

Raisz L G, "Bone resorption in tissue culture. Factors influencing the response to parathyroid hormone," *J Clin Invest*, 44:103–116, 1965.

Reddy S V, Alcantara O, Roodman G D, Boldt D H, "Inhibition of Tartrate-resistant acid phosphatase (TRAP) gene expression by hemin. Identification of a hemin responsive inhibitor of transcription," *Blood*, 88:2288–2297, 1996.

Reddy S V, Devlin R, Roodman G D, "Cloning and characterization of a novel autocrine osteoclast (OCL) stimulating factor (OSF)," *J Bone Miner Res*, 10:s325, 1995 (Abstract).

Reddy S V, Hundley J E, Windle J J, Alcantara O, Linn R, Leach R J, Boldt D H, Roodman G D, "Characterization of the mouse tartrate-resistant acid phosphatase (TRAP) gene promoter," *J Bone Miner Res*, 10(4):601–606, 1995.

Reddy S V, Kuzhandaivelu N, Acosta L, Roodman G D, "Characterization of the 5'-flanking region of the human tartrate-resistant acid phosphatase (TRAP) gene," *Bone*, 16(5):587–593, 1995.

Reddy S V, Singer F R, Mallette L, Roodman G D, "Detection of measles virus nucleocapsid transcripts in circulating blood cells and hematopoietic progenitors from patients with Paget's disease," *J Bone Miner Res*, 1996.

Reddy S V, Singer F R, Roodman G D, "Bone Marrow Mononuclear cells from patients with Paget's disease contain measles virus nucleocapsid mRNA that have mutations in a specific region of the sequence," *J Clin Endocrin Metab*, 80(7):2108–2111, 1995.

Reddy S V, Takahashi S, Dallas M, Williams R E, Neckers L, Roodman G D, "IL-6 Antisense Deoxyoligonucleotides inhibit bone resorption by giant cells from human giant cell tumors of bone," *J Bone Miner Res*, 9(5):753–757, 1994.

Reddy S V, Takahashi S, Roberts R M, Haipek C, Chirgwin J M, Roodman G D, "Tartrate-Resistant Acid Phosphatase Gene Expression as a Facile Reporter Gene for Screening Transfection Efficiency in Mammalian Cell Cultures," *Bio Techniques*, 15(3):444–447, 1993.

Romanos M A, Scorer C A, Clare J J, "Foreign gene expression in yeast: A review," *Yeast*, 8:423–88, 1992.

Roodman G D, Kurihara N, Ohsaki Y, Kukita A, Hosking D, Demulder A, Singer F R, "Interleukin-6: a potential autocrine/paracrine factor in Paget's disease of bone," *J Clin Invest*, 89:46–52, 1992.

Takahashi N, MacDonald B R, Hon J, Winkler M E, Derynck R, Mundy G R, Roodman G D, "Recombinant human transforming growth factor alpha stimulates the formation of osteoclast-like cells in long-term human marrow cultures," *J Clin Invest*, 78:894–898, 1986.

Takahashi N, Yamana H, Yoshiki S, Roodman G D, Mundy G R, Jones S J, Boyde A, Suda T, "Osteoclast-like cell formation and its regulation by osteotropic hormones in mouse bone marrow cultures," *Endocrinology*, 122:1373–1382, 1988.

Takahashi S, Goldring S, Katz M, Hilsenbeck S, Williams R, Roodman G D, "Downregulation of calcitonin receptor mRNA expression by calcitonin during human osteoclast-like cell differentiation," *J Clin Invest*, 95:167–171, 1995.

Takahashi S, Reddy S V, Chirgwin, J M, Devlin R, Haipek C, Anderson J, Roodman G D, "Cloning and identification of Annexin II as an autocrinelparacrine factor that increases osteoclast formation and bone resorption," *J Biol Chem*, 269(46):28696–28701, 1994.

Takahashi S, Reddy S V, Dallas M, Devlin R D, Chou J Y, Roodman G D, "Development and characterization of a human marrow stromal cell line that enhances osteoclast-like cell formation," *Endocrinology*, 136(4):1441–1449, 1995.

Uy H L, Dallas M, Calland J W, Boyce B F, Mundy G R, Roodman G D, "Use of an in vivo model to determine the effects of interleukin-1 on cells at different stages in the osteoclast lineage," *J. Bone Miner Res*, 10:295–301, 1995.

Weber D, Osdoby P, Hauschka P, Krukowski M, "Correlation of an osteoclast antigen and ruffled border on giant cells formed in response to resorbable substrates," *J Bone Miner Res*, 5:401–410, 1990.

Yoneda T, Williams P, Rhine C, Boyce B F, Dunstan C, Mundy G R, "Suramine suppresses hypercalcemia and osteoclastic bone resorption in nude mice bearing a human squamous cancer," *Cancer Res*, 55:1989–1993, 1995.

What is claimed is:

1. A method of inhibiting osteoclastogenesis, comprising administering an osteoclast inhibitor protein (OIP) to a cell wherein said OIP is effective to inhibit the production of osteoclasts, said OIP having the following characteristics:
   a. Produced from an osteoclast (OCL) cell;
   b. Inhibits bone resorption;
   c. Has the amino acid sequence of SEQ ID NO:2 or SEQ ID NO:4; and,
   d. Suppresses the growth of proliferating OCL-like multi-nucleated cells (MNC) formed in human marrow cultures.

2. The method of claim 1 wherein the cell is a bone marrow cell.

3. The method of claim 2 wherein the cell is in a mammal.

4. The method of claim 3 wherein the cell is human.

5. The method of claim 1 wherein the OIP composition comprises a protein that has the amino acid sequence of SEQ ID No:2 or SEQ ID No:4.

6. The method of claim 1 wherein the OIP composition comprises a protein having the amino acid sequence of SEQ ID NO:2 modified by replacement of asparagine at position 79 with glutamine.

7. The method of claim 1 wherein the OIP is administered in a physiologically acceptable vehicle.

* * * * *

UNITED STATES PATENT AND TRADEMARK OFFICE
CERTIFICATE OF CORRECTION

PATENT NO.    : 5,985,832
DATED         : Nov. 16, 1999
INVENTOR(S)   : G. David Roodman; Sakamuri V. Reddy; Sun-Jin Choi It is certified that error appears in the above-identified patent and that said Letters Patent is hereby corrected as shown below:

Title page,
In the title, at [54], please delete "INHIBITOR" and insert therefor -- INHIBITORY --. and col. 1 line 2.

In claim 5, column 60, line 32, delete "The method of claim 1," and insert therefor -- A method of inhibiting osteoclastogenesis comprising administering an osteoclast inhibitor protein (OIP) to a cell wherein said OIP --.

In claim 5, column 60, line 34, delete "wherein the OIP composition comprises a protein that".

In claim 6, column 60, line 36, delete "The method of claim 1," and insert therefor -- A method of inhibiting osteoclastogenesis comprising administering an osteoclast inhibitor protein (OIP) to a cell wherein said OIP -- .

In claim 6, column 60, line 36, delete "wherein the OIP composition comprises a protein having" and insert therefor -- has -- .

In claim 7, column 60, line 41, after "1", insert -- , 5 or 6 --.

Signed and Sealed this

Twenty-fourth Day of October, 2000

*Attest:*

Q. TODD DICKINSON

*Attesting Officer*            *Director of Patents and Trademarks*